US008110187B2

(12) United States Patent
Gately et al.

(10) Patent No.: US 8,110,187 B2
(45) Date of Patent: Feb. 7, 2012

(54) PURIFICATION AND CHARACTERIZATION OF CYTOTOXIC LYMPHOCYTE MATURATION FACTOR AND MONOCLONAL ANTIBODIES THERETO

(75) Inventors: Maurice Kent Gately, Montville, NJ (US); Ulrich Andreas Gubler, Glen Ridge, NJ (US); Jeffrey David Hulmes, Ringwood, NJ (US); Frank John Podlaski, New City, NY (US); Alvin Seth Stern, Passaic Park, NJ (US); Richard Anthony Chizzonite, South Kent, CT (US); Yu-Ching Eugene Pan, Pine Brook, NJ (US)

(73) Assignee: Hoffman-La Roche Inc., Nutley, NJ (US)

( * ) Notice: Subject to any disclaimer, the term of this patent is extended or adjusted under 35 U.S.C. 154(b) by 665 days.

(21) Appl. No.: 10/267,565

(22) Filed: Oct. 8, 2002

(65) Prior Publication Data

US 2003/0204059 A1    Oct. 30, 2003

Related U.S. Application Data

(60) Continuation of application No. 09/401,839, filed on Sep. 22, 1999, which is a division of application No. 08/459,151, filed on Jun. 2, 1995, now Pat. No. 6,683,046, which is a division of application No. 08/205,011, filed on Mar. 2, 1994, now abandoned, which is a division of application No. 07/857,023, filed on Mar. 24, 1992, now abandoned, which is a continuation-in-part of application No. 07/572,284, filed on Aug. 27, 1990, now abandoned, which is a continuation-in-part of application No. 07/520,935, filed on May 9, 1990, now abandoned, which is a continuation-in-part of application No. 07/455,708, filed on Dec. 22, 1989, now abandoned.

(51) Int. Cl.
*A61K 39/395* (2006.01)
*C07K 16/24* (2006.01)

(52) U.S. Cl. ............... 424/130.1; 424/158.1; 530/388.1; 530/388.23

(58) Field of Classification Search ................ 530/387.1
See application file for complete search history.

(56) References Cited

U.S. PATENT DOCUMENTS

| | | | |
|---|---|---|---|
| 4,473,555 A | 9/1984 | Nestor, Jr. et al. |
| 4,569,794 A | 2/1986 | Smith et al. |
| 5,457,038 A | 10/1995 | Trinchieri et al. |
| 5,569,454 A | 10/1996 | Trinchieri et al. |
| 5,648,072 A | 7/1997 | Trinchieri et al. |
| 5,648,467 A | 7/1997 | Trinchieri et al. |
| 5,650,492 A | 7/1997 | Gately et al. |
| 5,780,597 A | 7/1998 | Gately et al. |
| 5,811,523 A | 9/1998 | Trinchieri et al. |
| 5,853,697 A | 12/1998 | Strober et al. |
| 5,853,721 A | 12/1998 | Gately et al. |

FOREIGN PATENT DOCUMENTS

| | | |
|---|---|---|
| EP | 0 357 067 | 3/1990 |
| EP | 0 433 827 | 6/1991 |
| WO | WO 90/05147 | 5/1990 |
| WO | WO 95/05256 | 4/1992 |
| WO | WO 95/24918 | 9/1995 |
| WO | WO 98/34635 | 8/1998 |

OTHER PUBLICATIONS

Campbell, Monoclonal Antibody Technology, 1984, 1-32.*
Ruscetti et al. Blood, 1981, vol. 57, No. 3 p. 379-394.*
Aggarwal, 1987, in: *Protein Purification: Micro to Macro*, Richard Burgess, ed., Alan R. Liss, Inc., p. 22.
Bowie et al., 1990, "Deciphering the Message in Protein Sequences: Tolerance to Amino Acid Substitutions", Science 247:1306-1310.
Carter et al., 1997, "Production and Characterization of Monoclonal Antibodies to Human Interleukin-12", Hybridoma 16:363-369.
Casagli et al., 1987, "Purification of Recombinant Human Interleukin 1β Produced from Yeast", in: *Protein Purification: Micro to Macro*, Richard Burgess, ed., Alan R. Liss, Inc., pp. 421-427.
Chan et al., 1992, "Mechanisms of IFN-γ Induction by Natural Killer Cell Stimulatory Factor (NKSF/IL-12). Role of Transcription and mRNA Stability in the Synergistic Interaction between NKSF and IL-2", J. Immunol. 148:92-98.
Chan et al., 1991, "Induction of Interferon-γ Production by Natural Killer Cell Simulatory Factor: Characterization of the Responder Cells and Synergy with Other Inducers", J. Exp. Med. 173:869-879.
Chan et al., 1991, "Induction of Interferon-γ Production by Natural Killer Cell Simulatory Factor: Characterization of the Responder Cells and Synergy with Other Inducers", J. Exp. Med. 173:869-879.
Chehimi et al., 1992, "Natural Killer (NK) Cell Stimulatory Factor Increases the Cytotoxic Activity of NK Cells from both Healthy Donors and Human Immunodeficiency Virus-Infected Patients", J. Exp. Med. 175:789-796.
Chizzonite et al., 1994, "High and Low Affinity Receptors for Interleukin-12 (IL-12) on Human T-Cells: Evidence for a Two Subunit Receptor by IL-12 and Anti-Receptor Antibody Binding", 2$^{nd}$ International Cytokine Conference, Banff, Alberta, Canada, Oct. 1-5, 1994, vol. 6:A82 (abstract).
Chizzonite et al., 1991, "Cytotoxic Lymphocyte Maturation Factor (CLMF): Receptor on PHA-Activated Peripheral Blood Lymphoblasts (PHA-PBL) Mediates Binding and Biological Activity", FASEB J. 5:5568.
Chizzonite et al., 1991, "IL-12: Monoclonal Antibodies Specific for the 40-kDa Subunit Block Receptor Binding and Biologic Activity on Activated Human Lymphoblasts", J. Immunol. 147:1548-1556.

(Continued)

*Primary Examiner* — Yunsoo Kim
(74) *Attorney, Agent, or Firm* — Yankwich & Associates, P.C.; Leon R. Yankwich; Thomas R. Berka

(57) ABSTRACT

The present invention is a novel cytokine protein called IL-12 or Cytotoxic Lymphocyte Maturation Factor (CLMF) which is produced and synthesized by human NC-37 B lymphoblastoid cells (American Type Culture Collection, Rockville, Md.). CLMF synergistically induces with low concentrations of IL-2 the cytolytic activity of Lymphokine Activated Killer (LAK) cells, and CLMF is capable of stimulating T-cell growth.
Also claimed are the cloned gene for CLMF, its recombination in a suitable vector, the transformed cells containing said vector, the recombinant protein produced by the transformed cells and antibodies to CLMF.

5 Claims, 44 Drawing Sheets

OTHER PUBLICATIONS

Cohen, 1995, "IL-12 Deaths: Explanation and a Puzzle", Science 270:908.

Cytokine Bulletin, Spring 1996, "Technical Notes—Quantitation of Human IL-12 (p70) Using R&D Systems' Quantikine ELISA", pp. 1-2 and Cytokine Catalog, 1996, "Quantikine—Human IL-12 Immunoassay", pp. 1-13, both from R&D Systems; Genzyme Catalog, Interleukin 12 Reagents, p. 1.

D'Andrea et al., 1992, "Production of Natural Killer Cell Stimulatory Factor (Interleukin 12) by Peripheral Blood Mononuclear Cells", J. Exp. Med. 176:1387-1398.

Desai et al., 1991, "Regulation of Human Lymphocyte Proliferation by Cytotoxic Lymphocyte Maturation Factor (CLMF)", FASEB J. 5:2069.

Devos et al., 1983, "Molecular Cloning of Human Interleukin 2 cDNA and Its Expression in *E. coli*", Nucl. Acids. Res. 11:4307-4323.

Gately et al., 1995, "Measurement of Human and Mouse Interleukin 12", Cliff. Protocols in Immunology, vol. 1, pp. 6.16.1-6.16.8, John Wiley & Sons.

Gately et al., 1991, "Interleukin 12: A Novel Heterodimeric Cytokine with Potential Antitumor Applications", Neuroimmunol. Res. 4:20-32.

Gately et al., 1991, "Regulation of Human Lymphocyte Proliferation by a Heterodimeric Cytokine, IL-12 (Cytotoxic Lymphocyte Maturation Factor)", J. Immunol. 147:874-882.

Gately et al., 1990, "Isolation and Characterization of a Novel Lymphokine which Synergizes with IL-2 in the Generation of Activated NK/LAK Cells", Lymphokine Res. 9:566.

Gately et al., 1986, "Synergy between Recombinant Interleukin 2 (rIL 2) and IL 2-Depleted Lymphokine-Containing Supernatants in Facilitating Allogeneic Human Cytolytic T Lymphocyte Responses in vitro", J. Immunol. 136:1274-1282.

Gately et al., 1982, "In vitro Studies on the Cell-Mediated Immune Response to Human Brain Tumors. I. Requirement for Third-Party Stimulator Lymphocytes in the Induction of Cell-Mediated Cytotoxic Responses to Allogeneic Cultured Gliomas", J. Natl. Cancer Inst. 69:1245-1254.

Gearing and Cosman, 1991, "Homology of the p40 Subunit of Natural Killer Cell Stimulatory Factor (NKSF) with the Extracellular Domain of the Interleukin-6 Receptor", Cell 66:9-10.

Gillessen et al., 1995, "Mouse Interleukin-12 (IL-12) p40 Homodimer: A Potent IL-12 Antagonist", Eur. J. Immunol. 25:200-206.

Gubler et al., 1991, "Cloning and Expression of Cytotoxic Lymphocyte Maturation Factor (CLMF), a Heterodimeric Lymphokine that Potentiates NK, LAK and T-Cell Responses", Abs. J. Cellular Biochem. Suppl. 15F:70.

Gubler et al., 1991, "Coexpression of Two Distinct Genes is Required to Generate Secreted Bioactive Cytotoxic Lymphocyte Maturation Factor", Proc. Natl. Acad. Sci. USA. 88:4143-4147.

Herberman and Ortaldo, 1981, "Natural Killer Cells: Their Roles in Defenses against Disease", Science 214:24-30.

Ichimura et al., 1984, "Characterization of Mouse Natural Killer Cell Activating Factor (NKAF) Induced by OK-432: Evidence for Interferon- and Interleukin 2-Independent NK Cell Activation", Br. J. Cancer 50:97-108.

Katayama et al., 1979, "Comparison of Amino Acid Sequence of Bovine Coagulation Factor IX (Christmas Factor) with That of Other Vitamin K-Dependent Plasma Proteins", Proc. Natl. Acad. Sci. USA 7A:4990-4994.

Kobayashi et al., 1989, "Identification and Purification of Natural Killer Cell Stimulatory Factor (NKSF), a Cytokine with Multiple Biologic Effects on Human Lymphocytes", J. Exp. Med. ,120:827-845.

Lanier et al., 1988, "Interleukin 2 Activation of Natural Killer Cells Rapidly Induces the Expression and Phosphorylation of the Leu-23 Activation Antigen", J. Exp. Med. 167:1572-1585.

Lerner, 1982, "Tapping the Immunological Repertoire to Produce Antibodies of Predetermined Specificity", Nature 299:592-596.

Lieberman et al., 1991, "Natural Killer Cell Stimulatory Factor (NKSF) Augments Natural Killer Cell and Antibody-Dependent Tumoricidal Response against Colon Carcinoma Cell Lines", J. Surg. Res. 50:410-415.

Ling et al., 1995, "Human IL-12 p40 Homodimer Binds to the IL-12 Receptor but Does Not Mediate Biologic Activity", J. Immunol. 154:116-127.

Magram et al., 1996, "IL-12-Deficient Mice Are Defective in IFNγ Production and Type 1 Cytokine Responses", Immunity 4:471-481.

Marston, 1986, "The Purification of Eukaryotic Polypeptides Synthesized in *Escherichia coli*", Biochem. J. 240:1-12.

Mattner et al., 1993, "The Interleukin-12 Subunit p40 Specifically Inhibits Effects of the Interleukin-12 Heterodimer", Eur. J. Immunol. 23:2202-2208.

Mattner et al., 1996, "Genetically Resistant Mice Lacking Interleukin-12 Are Susceptible to Infection with *Leishmania major* and Mount a Polarized Th2 Cell Response", Eur. J. Immunol. 26:1553-1559.

Merberg et al., 1992, "Sequence Similarity between NKSF and the IL-6/G-CSF Family", Immunol. Today 13:77-78.

Ngo et al., 1994, "The Protein Folding Problem and Tertiary Structure Prediction", Menz et al., eds., Birkhüser, Boston, MA, pp. 433 and 492-495.

Petranyi et al., 1983, "Natural Killer Cells in Man: Genetic and Other Factors Regulating Their Activity", in: *Progress in Immunology*, vol. 5, Yamamura and Tada, eds., Academic Press Japan, Inc., pp. 1169, 1174-1175, 1178-1180.

Podlaski et al., 1992, "Molecular Characterization of Interleukin 12", Arch. Biochem. Biophys. 294:230-237.

Podlaski et al., 1991, "Molecular Characterization of a Novel Cytokine: Cytotoxic Lymphocyte Maturation Factor", Abs. J. Cell. Biochem. Suppl. 15F:78.

Presky et al., 1996, "Evidence for Multiple Sites of Interaction between IL-12 and Its Receptor", Ann. NY Acad. Sci 795:390-393.

Richard et al., 1987, "Cytokines Involved in the Augmentation of Murine Natural Killer Cell Activity by Pyrimidinones in vivo", J. Biol. Response Mod. 6:647-663.

Robertson et al., 1992, "Response of Human Natural Killer (NK) Cells to NK Cell Stimulatory Factor (NKSF): Cytolytic Activity and Proliferation of NK Cells are Differentially Regulated by NKSF", J. Exp. Med. 175:779-788.

Sieling et al., 1994, "IL-12 Regulates T Helper Type 1 Cytokine Responses in Human Infectious Disease", J. Immunol. 153:3639-3647.

Sinosich et al., 1987, "Affinity Immunoelectrophoresis and Chromatography for Isolation and Characterization of a Placental Granulocyte Elastase Inhibitor", in: *Protein Purification*, Burgess, ed., Alan R. Liss, pp. 225-238.

Smith et al., 1983, "Production and Characterization of Monoclonal Antibodies to Human Interleukin 2: Strategy and Tactics", J. Immunol. 131:1808-1815.

Stern and Podlaski, 1993, "Increasing the Antigen Binding Capacity of Immobilized Antibodies", in: *Techniques in Protein Chemistry IV*, Academic Press, Inc., pp. 353-360.

Stern et al., 1990, "Purification to Homogeneity and Partial Characterization of Cytotoxic Lymphocyte Maturation Factor from Human B-Lymphoblastoid Cells", Proc. Natl. Acad. Sci. USA 87:6808-6812.

Talmadge, 1985, "Immunoregulation and Immunostimulation of Murine Lymphocytes by Recombinant Human Interleukin-2", J. Biol. Response Modifiers 4:18-34.

Thiele et al., 1983, "Phenotype of the Accessory Cell Necessary for Mitogen-Stimulated T and B Cell Responses in Human Peripheral Blood: Delineation by Its Sensitivity to the Lysosomotropic Agent, L-Leucine Methyl Ester", J. Immunol. 131:2282-2290.

Trinchieri, 1993, "Interleukin-12 and Its Role in the Generation of TH1 Cells", Immunol. Today 14:335-338.

Truitt et al., 1991, "Initial Characterization of the Receptor for Cytotoxic Lymphocyte Maturation Factor (CLMF) on PHA-Activated Human Peripheral Blood Lymphoblasts (PHA-PBL)", Abs. J. Cell. Biochem. Suppl. 15F:120.

Wasserman et al., 1987, "Purification and Characterization of Recombinant Hyman Malaria Vaccine Candidates from *E. coli*", in: *Protein Purification: Micro to Macro*, Richard Burgess, ed., Alan R. Liss, Inc., pp. 337-354.

Wei and Joys, 1985, "Covalent Structure of Three Phase-1 Flagellar Filament Proteins of Salmonella", J. Mol. Biol. 186:791-803.

Wolf et al., 1991, "Cloning of cDNA for Natural Killer Cell Stimulatory Factor, a Heterodimeric Cytokine with Multiple Biologic Effects on T and Natural Killer Cells", J. Immunol. 146:3074-3081.

Wong and Clark, 1988. "Multiple Actions of Interleukin 6 within a Cytokine Network", Immunol. Today 9:137-139.

Wong et al., 1988, "Characterization of a Factor(s) which Synergizes with Recombinant Interleukin 2 in Promoting Allogeneic Human Cytolytic T-Lymphocyte Responses in vitro", Cell. Immunol. 111:39-54.

Wong et al., 1986, "Characterization of a Human CTL Maturation Factor", Abst., 6th Int'l. Congress of Immunol. 311.

Zhang et al., 1994, "Interleukin 12 at the Site of Disease in Tuberculosis", J. Clin. Invest. 93:1733-1739.

Zou et al., 1995, "Structure-Function Analysis of the p35 Subunit of Mouse Interleukin 12", J. Biol. Chem. 270:5864-5871.

* cited by examiner

```
          10         20         30         40        49         58
                                                     >
GTTTCAGGGC CATTGGACTC TCCGTCCTGC CCAGAGCAAG ATG TGT CAC CAG CAG TTG GTC
                                                 MET Cys His Gln Gln Leu Val 67         76         85         94         103        112
ATC TCT TGG TTT TCC CTG GTT TTT CTG GCA TCT CCC CTC GTG GCC ATA TGG GAA
Ile Ser Trp Phe Ser Leu Val Phe Leu Ala Ser Pro Leu Val Ala Ile Trp Glu 121        130        139        148        157        166
CTG AAG AAA GAT GTT TAT GTC GTA GAA TTG GAT TGG TAT CCG GAT GCC CCT GGA
Leu Lys Lys Asp Val Tyr Val Val Glu Leu Asp Trp Tyr Pro Asp Ala Pro Gly 175        184        193        202        211        220
GAA ATG GTG GTC CTC ACC TGT GAC ACC CCT GAA GAA GAT GGT ATC ACC TGG ACC
Glu MET Val Val Leu Thr Cys Asp Thr Pro Glu Glu Asp Gly Ile Thr Trp Thr 229        238        247        256        265        274
TTG GAC CAG AGC AGT GAG GTC TTA GGC TCT GGC AAA ACC CTG ACC ATC CAA GTC
Leu Asp Gln Ser Ser Glu Val Leu Gly Ser Gly Lys Thr Leu Thr Ile Gln Val 283        292        301        310        319        328
AAA GAG TTT GGA GAT GCT GGC CAG TAC ACC TGT CAC AAA GGA GGC GAG GTT CTA
Lys Glu Phe Gly Asp Ala Gly Gln Tyr Thr Cys His Lys Gly Gly Glu Val Leu
```

FIG. 25a

```
337                 346                 355                 364                 373                 382
AGC CAT TCG         CTC CTG CTT         CAC AAA AAG         GAT GGA ATT         TGG TCC ACT         GAT
Ser His Ser         Leu Leu Leu         His Lys Lys         Asp Gly Ile         Trp Ser Thr         Asp 391                 400                 409                 418                 427                 436
ATT TTA AAG         GAC CAG AAA         GAA CCC AAA         AAT TTT ACC         AAG TGG ATT         TCC ACT GCC
Ile Leu Lys         Asp Gln Lys         Glu Pro Lys         Asn Phe Thr         Lys Trp Ile         Ser Thr Ala 445                 454                 463                 472                 481                 490
AAG AAT TAT         TCT GGA CGT         TTC ACC TGC         TGG CTG ACG         ACA ATC AGT         ACT GAT
Lys Asn Tyr         Ser Gly Arg         Phe Thr Cys         Trp Leu Thr         Thr Ile Ser         Thr Asp 499                 508                 517                 526                 535                 544
TTG ACA TTC         AGT GTC AAA         AGC AGA GGC         TCT TCT GAC         CCC CAA GGG         GTG ACG
Leu Thr Phe         Ser Val Lys         Ser Arg Gly         Ser Ser Asp         Pro Gln Gly         Val Thr 553                 562                 571                 580                 589                 598
TGC GGA GCT         GCT ACA CTC         TCT GCA GAG         AGA GTC AGA         GAC AAC AAG         GAG TAT
Cys Gly Ala         Ala Thr Leu         Ser Ala Glu         Arg Val Arg         Asp Asn Lys         Glu Tyr 607                 616                 625                 634                 643                 652
GAG TAC TCA         GTG GAG TGC         CAG GAG GAC         AGT GCC TGC         CCA GCT GCT         GAG GAG AGT
Glu Tyr Ser         Val Glu Cys         Gln Glu Asp         Ser Ala Cys         Pro Ala Ala         Glu Glu Ser
```

FIG. 25b

| 661 | | | | | | | | | |
|---|---|---|---|---|---|---|---|---|---|
| CTG | CCC | ATT | GAG | GTC | ATG | GTG | GCC | GTT | CAC | AAG | CTC | TAT | GAA | AAC | TAC |
| Leu | Pro | Ile | Glu | Val | MET | Val | Ala | Val | His | Lys | Leu | Tyr | Glu | Asn | Tyr |

715 ... 760

| ACC | AGC | TTC | ATC | AGG | GAC | ATC | AAA | CCT | GAC | CCA | CCC | AAG | AAC | TTG |
|---|---|---|---|---|---|---|---|---|---|---|---|---|---|---|
| Thr | Ser | Ser | Phe | Ile | Arg | Asp | Ile | Lys | Pro | Asp | Pro | Pro | Lys | Asn | Leu |

769 ... 814

| CAG | AAG | CCA | TTA | AAG | AAT | TCT | CGG | CAG | GTG | GAG | GTC | TGG | GAG | TAC | CCT |
|---|---|---|---|---|---|---|---|---|---|---|---|---|---|---|---|
| Gln | Lys | Pro | Leu | Lys | Asn | Ser | Arg | Gln | Val | Glu | Val | Trp | Glu | Tyr | Pro |

823 ... 868

| GAC | ACC | TGG | AGT | ACT | CCA | CAT | TCC | CTG | ACA | TTC | TGC | GTT | CAG | GTC |
|---|---|---|---|---|---|---|---|---|---|---|---|---|---|---|
| Asp | Thr | Trp | Ser | Thr | Pro | His | Ser | Leu | Thr | Phe | Cys | Val | Gln | Val |

877 ... 922

| CAG | GGC | AAG | AGC | AAG | AGA | GAA | AAG | GAT | AGA | GTC | TTC | GAC | AAG | ACC | TCA |
|---|---|---|---|---|---|---|---|---|---|---|---|---|---|---|---|
| Gln | Gly | Lys | Ser | Lys | Arg | Glu | Lys | Asp | Arg | Val | Phe | Asp | Lys | Thr | Ser |

931 ... 976

| GCC | ACG | GTC | ATC | TGC | CGC | AAA | AAT | GCC | AGC | GTG | ATT | AGC | GTG | CGG | GCC | CAG | GAC | CGC |
|---|---|---|---|---|---|---|---|---|---|---|---|---|---|---|---|---|---|---|
| Ala | Thr | Val | Ile | Cys | Arg | Lys | Asn | Ala | Ser | Val | Ile | Ser | Val | Arg | Ala | Gln | Asp | Arg |

FIG. 25c

```
     985       994      1003      1012      1021            1034
TAC  TAT  AGC  TCA  TCT  TGG  AGC  GAA  TGG  GCA  TCT  GTG  CCC  TGC  AGT  TAGGTTCTGA
Tyr  Tyr  Ser  Ser  Ser  Trp  Ser  Glu  Trp  Ala  Ser  Val  Pro  Cys  Ser
                                                                    >

1044           1054           1064           1074           1084           1094           1104
TCCAGGATGA     AAATTGGAGA     GAAAAGTGGA     AGATATTAAG     CAAAATGTTT     AAAGACACAA     CGGAATAGAC 1114           1124           1134           1144           1154           1164           1174
CCAAAAAGAT     AATTTCTATC     TGATTTGCTT     TAAAACGTTT     TTTTAGGATC     ACAATGATAT     CTTTGCTGTA 1184           1194           1204           1214           1224           1234           1244
TTTGTATAGT     TAGATGCTAA     ATGCTCATTG     AAACAATCAG     CTAATTTATG     TATAGATTTT     CCAGCTCTCA 1254           1264           1274           1284           1294           1304           1314
AGTTGCCATG     GGCCTTCATG     CTATTTAAAT     ATTTAAGTAA     TTTATGTATT     TATTAGTATA     TTACTGTTAT 1324           1334           1344           1354           1364           1374           1384           1394
TTAACGTTTG     TCTGCCAGGA     TGTATGGAAT     GTTTCATACT     CTTATGACCT     GATCCATCAG     GATCAGTCCC     TATTATGCAA     AAT
```

FIG. 25d

```
         10         20         30         40         50         60         70
GAATTCCCAG AAAGCAAGAG ACCAGAGTCC CGGGAAAGTC CTGCCGCGCC TCGGGACAAT TATAAAAATG 80         90        100        110        120        130        140
TGGCCCCCTG GGTCAGCCTC CCAGCCACCG CCCTCACCTG CCGCGGCCAC AGGTCTGCAT CCAGCGGCTC 150        160        169        178        187        196
                                 >
GCCCTGTGTC CCTGCAGTGC CGGCTCAGC ATG TGT CCA GCG CGC AGC CTC CTC CTT GTG
                                   MET Cys Pro Ala Arg Ser Leu Leu Leu Val 205        214        223        232        241        250
GCT ACC CTG GTC CTC CTG GAC CAC CTC AGT TTG GCC AGA AAC CTC CCC GTG GCC
Ala Thr Leu Val Leu Leu Asp His Leu Ser Leu Ala Arg Asn Leu Pro Val Ala 259        268        277        286        295        304
ACT CCA GAC CCA GGA ATG TTC CCA TGC CTT CAC CAC TCC CAA AAC CTG CTG AGG
Thr Pro Asp Pro Gly MET Phe Pro Cys Leu His His Ser Gln Asn Leu Leu Arg 313        322        331        340        349        358
GCC GTC AGC AAC ATG CTC CAG AAG GCC AGA CAA ACT CTA GAA TTT TAC CCT TGC
Ala Val Ser Asn MET Leu Gln Lys Ala Arg Gln Thr Leu Glu Phe Tyr Pro Cys 367        376        385        394        403        412
ACT TCT GAA GAG ATT GAT CAT GAA GAT ATC ACA AAA GAT AAA ACC AGC ACA GTG
Thr Ser Glu Glu Ile Asp His Glu Asp Ile Thr Lys Asp Lys Thr Ser Thr Val
```

FIG. 26a

```
421              430              439              448              457              466
GAG GCC TGT TTA CCA TTG GAA TTA ACC AAG AAT GAG AGT TGC CTA AAT TCC AGA    100
Glu Ala Cys Leu Pro Leu Glu Leu Thr Lys Asn Glu Ser Cys Leu Asn Ser Arg 475              484              493              502              511              520
                                                                                      96  118
GAG ACC TCT TTC ATA ACT AAT GGG AGT TGC CTG GCC TCC AGA AAG ACC TCT TTT    118
Glu Thr Ser Phe Ile Thr Asn Gly Ser Cys Leu Ala Ser Arg Lys Thr Ser Phe
                        108

529              538              547              556              565              574
                                           108                                         114
ATG ATG GCC CTG TGC CTT AGT AGT ATT TAT GAA GAC TTG AAG ATG TAC CAG GTG    136
MET MET Ala Leu Cys Leu Ser Ser Ile Tyr Glu Asp Leu Lys MET Tyr Gln Val 583              592              601              610              619              628
GAG TTC AAG ACC ATG AAT GCA AAG CTT CTG ATG GAT CCT AAG AGG CAG ATC TTT    154
Glu Phe Lys Thr MET Asn Ala Lys Leu Leu MET Asp Pro Lys Arg Gln Ile Phe 637              646              655              664              673              682
                                                                                         172
CTA GAT CAA AAC ATG CTG GCA GTT ATT GAT GAG CTG ATG CAG GCC CTG AAT TTC
Leu Asp Gln Asn MET Leu Ala Val Ile Asp Glu Leu MET Gln Ala Leu Asn Phe 691              700              709              718              727              736
AAC AGT GAG ACT GTG CCA CAA AAA TCC TCC CTT GAA GAA CCG GAT TTT TAT AAA    190
Asn Ser Glu Thr Val Pro Gln Lys Ser Ser Leu Glu Glu Pro Asp Phe Tyr Lys 745              754              763              772              781              790
ACT AAA ATC AAG CTC TGC ATA CTT CTT CAT GCT TTC AGA ATT CGG GCA GTG ACT   208
Thr Lys Ile Lys Leu Cys Ile Leu Leu His Ala Phe Arg Ile Arg Ala Val Thr
                                                                      #208
```

FIG. 26b

```
      799           808           817           826
                                                 ‾‾‾>
ATT  GAC  AGA  GTG  ACG  AGC  TAT  CTG  AAT  GCT  TCC
Ile  Asp  Arg  Val  Thr  Ser  Tyr  Leu  Asn  Ala  Ser
                    *213
```

```
         836           846           856
TAAAAAGCGA  GGTCCCTCCA  AACCGTTGTC
```

FIG. 26c

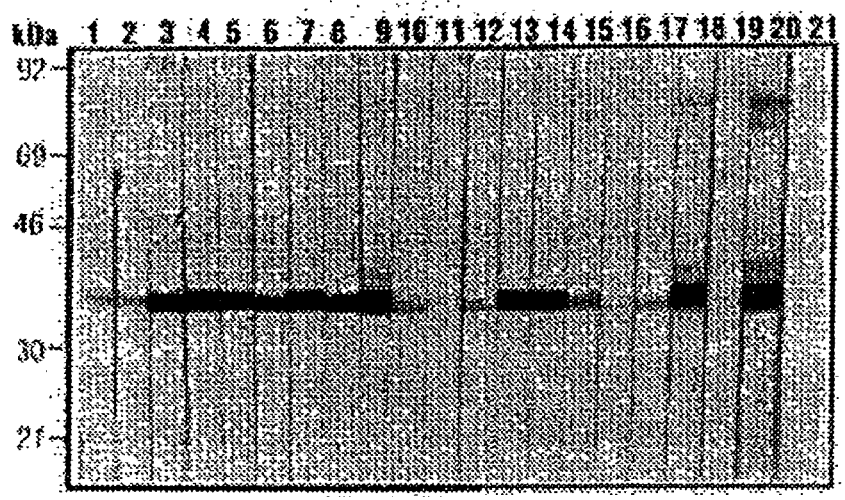
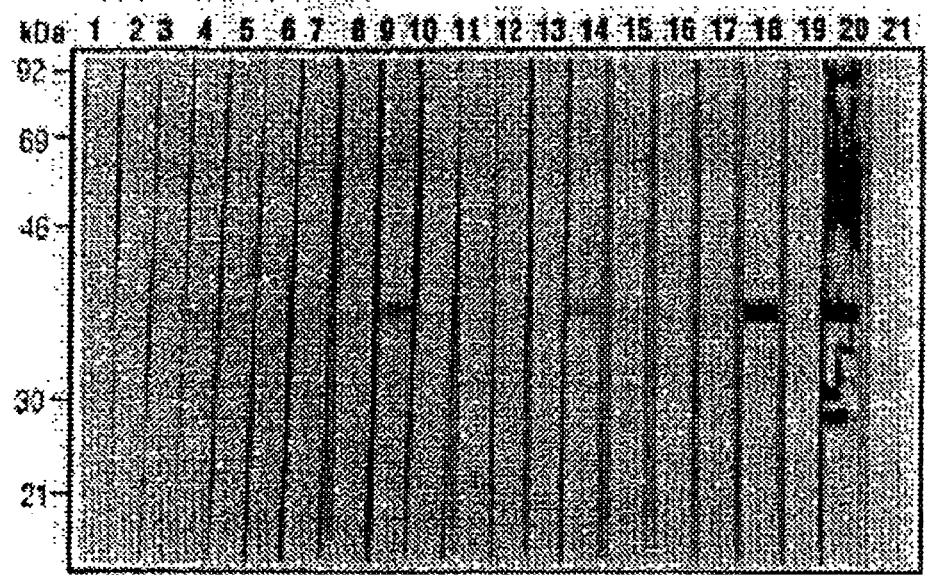
FIG. 32

SEQUENCE LISTING

```
<160> NUMBER OF SEQ ID NOS: 43

<210> SEQ ID NO 1
<211> LENGTH: 306
<212> TYPE: PRT
<213> ORGANISM: Homo sapiens

<400> SEQUENCE: 1

Ile Trp Glu Leu Lys Lys Asp Val Tyr Val Val Glu Leu Asp Trp Tyr
1               5                   10                  15

Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
        35                  40                  45

Ser Gly Lys Thr Leu Thr Ile Gln Val Lys Glu Phe Gly Asp Ala Gly
    50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asp Pro Gln
    130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
        195                 200                 205
```

-continued

```
Asp Ile Ile Lys Pro Asp Pro Pro Lys Asn Leu Gln Leu Lys Pro Leu
    210             215                 220
Lys Asn Ser Arg Gln Val Glu Val Ser Trp Glu Tyr Pro Asp Thr Trp
225                 230                 235                 240
Ser Thr Pro His Ser Tyr Phe Ser Leu Thr Phe Cys Val Gln Val Gln
                245                 250                 255
Gly Lys Ser Lys Arg Glu Lys Lys Asp Arg Val Phe Thr Asp Lys Thr
                260                 265                 270
Ser Ala Thr Val Ile Cys Arg Lys Asn Ala Ser Ile Ser Val Arg Ala
                275                 280                 285
Gln Asp Arg Tyr Tyr Ser Ser Trp Ser Glu Trp Ala Ser Val Pro
    290                 295                 300
Cys Ser
305

<210> SEQ ID NO 2
<211> LENGTH: 1397
<212> TYPE: DNA
<213> ORGANISM: Homo sapiens
<220> FEATURE:
<221> NAME/KEY: CDS
<222> LOCATION: (41)...(1024)

<400> SEQUENCE: 2
gtttcagggc cattggactc tccgtcctgc ccagagcaag atg tgt cac cag cag         55
                                           Met Cys His Gln Gln
                                             1               5 ttg gtc atc tct tgg ttt tcc ctg gtt ttt ctg gca tct ccc ctc gtg        103
Leu Val Ile Ser Trp Phe Ser Leu Val Phe Leu Ala Ser Pro Leu Val
             10                  15                  20 gcc ata tgg gaa ctg aag aaa gat gtt tat gtc gta gaa ttg gat tgg        151
Ala Ile Trp Glu Leu Lys Lys Asp Val Tyr Val Val Glu Leu Asp Trp
             25                  30                  35 tat ccg gat gcc cct gga gaa atg gtg gtc ctc acc tgt gac acc cct        199
Tyr Pro Asp Ala Pro Gly Glu Met Val Val Leu Thr Cys Asp Thr Pro
         40                  45                  50 gaa gaa gat ggt atc acc tgg acc ttg gac cag agc agt gag gtc tta        247
Glu Glu Asp Gly Ile Thr Trp Thr Leu Asp Gln Ser Ser Glu Val Leu
         55                  60                  65 ggc tct ggc aaa acc ctg acc atc caa gtc aaa gag ttt gga gat gct        295
Gly Ser Gly Lys Thr Leu Thr Ile Gln Val Lys Glu Phe Gly Asp Ala
 70                  75                  80                  85 ggc cag tac acc tgt cac aaa gga ggc gag gtt cta agc cat tcg ctc        343
Gly Gln Tyr Thr Cys His Lys Gly Gly Glu Val Leu Ser His Ser Leu
                 90                  95                 100 ctg ctg ctt cac aaa aag gaa gat gga att tgg tcc act gat att tta        391
Leu Leu Leu His Lys Lys Glu Asp Gly Ile Trp Ser Thr Asp Ile Leu
            105                 110                 115 aag gac cag aaa gaa ccc aaa aat aag acc ttt cta aga tgc gag gcc        439
Lys Asp Gln Lys Glu Pro Lys Asn Lys Thr Phe Leu Arg Cys Glu Ala
        120                 125                 130 aag aat tat tct gga cgt ttc acc tgc tgg tgg ctg acg aca atc agt        487
Lys Asn Tyr Ser Gly Arg Phe Thr Cys Trp Trp Leu Thr Thr Ile Ser
        135                 140                 145 act gat ttg aca ttc agt gtc aaa agc agc aga ggc tct tct gac ccc        535
Thr Asp Leu Thr Phe Ser Val Lys Ser Ser Arg Gly Ser Ser Asp Pro
150                 155                 160                 165 caa ggg gtg acg tgc gga gct gct aca ctc tct gca gag aga gtc aga        583
Gln Gly Val Thr Cys Gly Ala Ala Thr Leu Ser Ala Glu Arg Val Arg
                170                 175                 180
```

```
ggg gac aaa caa gga tat gag tac tca gtg gag tgc cag gag gac agt    631
Gly Asp Lys Gln Gly Tyr Glu Tyr Ser Val Glu Cys Gln Glu Asp Ser
            185                 190                 195 gcc tgc cca gct gct gag gag agt ctg ccc att gag gtc atg gtg gat    679
Ala Cys Pro Ala Ala Glu Glu Ser Leu Pro Ile Glu Val Met Val Asp
200                 205                 210 gcc gtt cac aag ctc aag tat gaa aac tac acc agc agc ttc ttc atc    727
Ala Val His Lys Leu Lys Tyr Glu Asn Tyr Thr Ser Ser Phe Phe Ile
        215                 220                 225 agg gac atc atc aaa cct gac cca ccc aag aac ttg cag ctg aag cca    775
Arg Asp Ile Ile Lys Pro Asp Pro Pro Lys Asn Leu Gln Leu Lys Pro
230                 235                 240                 245 tta aag aat tct cgg cag gtg gag gtc agc tgg gag tac cct gac acc    823
Leu Lys Asn Ser Arg Gln Val Glu Val Ser Trp Glu Tyr Pro Asp Thr
                250                 255                 260 tgg agt act cca cat tcc tac ttc tcc ctg aca ttc tgc gtt cag gtc    871
Trp Ser Thr Pro His Ser Tyr Phe Ser Leu Thr Phe Cys Val Gln Val
            265                 270                 275 cag ggc aag agc aag aga gaa aag aaa gat aga gtc ttc acg gac aag    919
Gln Gly Lys Ser Lys Arg Glu Lys Lys Asp Arg Val Phe Thr Asp Lys
        280                 285                 290 acc tca gcc acg gtc atc tgc cgc aaa aat gcc agc att agc gtg cgg    967
Thr Ser Ala Thr Val Ile Cys Arg Lys Asn Ala Ser Ile Ser Val Arg
295                 300                 305 gcc cag gac cgc tac tat agc tca tct tgg agc gaa tgg gca tct gtg    1015
Ala Gln Asp Arg Tyr Tyr Ser Ser Ser Trp Ser Glu Trp Ala Ser Val
310                 315                 320                 325 ccc tgc agt taggttctga tccaggatga aaatttggag gaaaagtgga             1064
Pro Cys Ser agatattaag caaatgtttt aaagacacaa cggaatagac ccaaaaagat aatttctatc   1124
tgatttgctt taaaacgttt ttttaggatc acaatgatat ctttgctgta tttgtatagt   1184
tagatgctaa atgctcattg aaacaatcag ctaatttatg tatagatttt ccagctctca   1244
agttgccatg ggccttcatg ctatttaaat atttaagtaa tttatgtatt tattagtata   1304
ttactgttat ttaacgtttg tctgccagga tgtatggaat gtttcatact cttatgacct   1364
gatccatcag gatcagtccc tattatgcaa aat                                1397

<210> SEQ ID NO 3
<211> LENGTH: 328
<212> TYPE: PRT
<213> ORGANISM: Homo sapiens

<400> SEQUENCE: 3

Met Cys His Gln Gln Leu Val Ile Ser Trp Phe Ser Leu Val Phe Leu
1               5                   10                  15

Ala Ser Pro Leu Val Ala Ile Trp Glu Leu Lys Lys Asp Val Tyr Val
            20                  25                  30

Val Glu Leu Asp Trp Tyr Pro Asp Ala Pro Gly Glu Met Val Val Leu
        35                  40                  45

Thr Cys Asp Thr Pro Glu Glu Asp Gly Ile Thr Trp Thr Leu Asp Gln
    50                  55                  60

Ser Ser Glu Val Leu Gly Ser Gly Lys Thr Leu Thr Ile Gln Val Lys
65                  70                  75                  80

Glu Phe Gly Asp Ala Gly Gln Tyr Thr Cys His Lys Gly Gly Glu Val
                85                  90                  95

Leu Ser His Ser Leu Leu Leu Leu His Lys Lys Glu Asp Gly Ile Trp
            100                 105                 110
```

```
Ser Thr Asp Ile Leu Lys Asp Gln Lys Glu Pro Lys Asn Lys Thr Phe
        115                 120                 125
Leu Arg Cys Glu Ala Lys Asn Tyr Ser Gly Arg Phe Thr Cys Trp Trp
130                 135                 140
Leu Thr Thr Ile Ser Thr Asp Leu Thr Phe Ser Val Lys Ser Ser Arg
145                 150                 155                 160
Gly Ser Ser Asp Pro Gln Gly Val Thr Cys Gly Ala Ala Thr Leu Ser
                165                 170                 175
Ala Glu Arg Val Arg Gly Asp Lys Gln Gly Tyr Glu Tyr Ser Val Glu
                180                 185                 190
Cys Gln Glu Asp Ser Ala Cys Pro Ala Ala Glu Glu Ser Leu Pro Ile
                195                 200                 205
Glu Val Met Val Asp Ala Val His Lys Leu Lys Tyr Glu Asn Tyr Thr
    210                 215                 220
Ser Ser Phe Phe Ile Arg Asp Ile Ile Lys Pro Asp Pro Pro Lys Asn
225                 230                 235                 240
Leu Gln Leu Lys Pro Leu Lys Asn Ser Arg Gln Val Glu Val Ser Trp
                245                 250                 255
Glu Tyr Pro Asp Thr Trp Ser Thr Pro His Ser Tyr Phe Ser Leu Thr
                260                 265                 270
Phe Cys Val Gln Val Gln Gly Lys Ser Lys Arg Glu Lys Lys Asp Arg
    275                 280                 285
Val Phe Thr Asp Lys Thr Ser Ala Thr Val Ile Cys Arg Lys Asn Ala
    290                 295                 300
Ser Ile Ser Val Arg Ala Gln Asp Arg Tyr Tyr Ser Ser Ser Trp Ser
305                 310                 315                 320
Glu Trp Ala Ser Val Pro Cys Ser
                325

<210> SEQ ID NO 4
<211> LENGTH: 856
<212> TYPE: DNA
<213> ORGANISM: Homo sapiens
<220> FEATURE:
<221> NAME/KEY: CDS
<222> LOCATION: (170)...(826)

<400> SEQUENCE: 4
gaattcccag aaagcaagag accagagtcc cgggaaagtc ctgccgcgcc tcgggacaat      60 tataaaatg tggcccctg gtcagcctc cagccaccg ccctcacctg ccgcggccac        120
aggtctgcat ccagcggctc gccctgtgtc cctgcagtgc cggctcagc atg tgt cca     178
                                                     Met Cys Pro
                                                       1 gcg cgc agc ctc ctc ctt gtg gct acc ctg gtc ctg gac cac ctc          226
Ala Arg Ser Leu Leu Leu Val Ala Thr Leu Val Leu Asp His Leu
    5                  10                 15 agt ttg gcc aga aac ctc ccc gtg gcc act cca gac cca gga atg ttc      274
Ser Leu Ala Arg Asn Leu Pro Val Ala Thr Pro Asp Pro Gly Met Phe
 20                  25                  30                  35 cca tgc ctt cac cac tcc caa aac ctg ctg agg gcc gtc agc aac atg      322
Pro Cys Leu His His Ser Gln Asn Leu Leu Arg Ala Val Ser Asn Met
                 40                  45                  50 ctc cag aag gcc aga caa act cta gaa ttt tac cct tgc act tct gaa      370
Leu Gln Lys Ala Arg Gln Thr Leu Glu Phe Tyr Pro Cys Thr Ser Glu
             55                  60                  65 gag att gat cat gaa gat atc aca aaa gat aaa acc agc aca gtg gag      418
Glu Ile Asp His Glu Asp Ile Thr Lys Asp Lys Thr Ser Thr Val Glu
         70                  75                  80
```

-continued

```
gcc tgt tta cca ttg gaa tta acc aag aat gag agt tgc cta aat tcc      466
Ala Cys Leu Pro Leu Glu Leu Thr Lys Asn Glu Ser Cys Leu Asn Ser
    85                  90                  95 aga gag acc tct ttc ata act aat ggg agt tgc ctg gcc tcc aga aag      514
Arg Glu Thr Ser Phe Ile Thr Asn Gly Ser Cys Leu Ala Ser Arg Lys
100                 105                 110                 115 acc tct ttt atg atg gcc ctg tgc ctt agt agt att tat gaa gac ttg      562
Thr Ser Phe Met Met Ala Leu Cys Leu Ser Ser Ile Tyr Glu Asp Leu
                120                 125                 130 aag atg tac cag gtg gag ttc aag acc atg aat gca aag ctt ctg atg      610
Lys Met Tyr Gln Val Glu Phe Lys Thr Met Asn Ala Lys Leu Leu Met
        135                 140                 145 gat cct aag agg cag atc ttt cta gat caa aac atg ctg gca gtt att      658
Asp Pro Lys Arg Gln Ile Phe Leu Asp Gln Asn Met Leu Ala Val Ile
    150                 155                 160 gat gag ctg atg cag gcc ctg aat ttc aac agt gag act gtg cca caa      706
Asp Glu Leu Met Gln Ala Leu Asn Phe Asn Ser Glu Thr Val Pro Gln
165                 170                 175 aaa tcc tcc ctt gaa gaa ccg gat ttt tat aaa act aaa atc aag ctc      754
Lys Ser Ser Leu Glu Glu Pro Asp Phe Tyr Lys Thr Lys Ile Lys Leu
180                 185                 190                 195 tgc ata ctt ctt cat gct ttc aga att cgg gca gtg act att gac aga      802
Cys Ile Leu Leu His Ala Phe Arg Ile Arg Ala Val Thr Ile Asp Arg
                200                 205                 210 gtg acg agc tat ctg aat gct tcc taaaaagcga ggtccctcca aaccgttgtc     856
Val Thr Ser Tyr Leu Asn Ala Ser
                215

<210> SEQ ID NO 5
<211> LENGTH: 219
<212> TYPE: PRT
<213> ORGANISM: Homo sapiens

<400> SEQUENCE: 5

Met Cys Pro Ala Arg Ser Leu Leu Leu Val Ala Thr Leu Val Leu Leu
  1               5                  10                  15

Asp His Leu Ser Leu Ala Arg Asn Leu Pro Val Ala Thr Pro Asp Pro
                20                  25                  30

Gly Met Phe Pro Cys Leu His His Ser Gln Asn Leu Leu Arg Ala Val
            35                  40                  45

Ser Asn Met Leu Gln Lys Ala Arg Gln Thr Leu Glu Phe Tyr Pro Cys
        50                  55                  60

Thr Ser Glu Glu Ile Asp His Glu Asp Ile Thr Lys Asp Lys Thr Ser
 65                 70                  75                  80

Thr Val Glu Ala Cys Leu Pro Leu Glu Leu Thr Lys Asn Glu Ser Cys
                85                  90                  95

Leu Asn Ser Arg Glu Thr Ser Phe Ile Thr Asn Gly Ser Cys Leu Ala
            100                 105                 110

Ser Arg Lys Thr Ser Phe Met Met Ala Leu Cys Leu Ser Ser Ile Tyr
        115                 120                 125

Glu Asp Leu Lys Met Tyr Gln Val Glu Phe Lys Thr Met Asn Ala Lys
130                 135                 140

Leu Leu Met Asp Pro Lys Arg Gln Ile Phe Leu Asp Gln Asn Met Leu
145                 150                 155                 160

Ala Val Ile Asp Glu Leu Met Gln Ala Leu Asn Phe Asn Ser Glu Thr
                165                 170                 175

Val Pro Gln Lys Ser Ser Leu Glu Glu Pro Asp Phe Tyr Lys Thr Lys
            180                 185                 190
```

Ile Lys Leu Cys Ile Leu Leu His Ala Phe Arg Ile Arg Ala Val Thr
               195                 200                 205

Ile Asp Arg Val Thr Ser Tyr Leu Asn Ala Ser
               210                 215

<210> SEQ ID NO 6
<211> LENGTH: 20
<212> TYPE: PRT
<213> ORGANISM: Homo sapiens
<220> FEATURE:
<221> NAME/KEY: SITE
<222> LOCATION: (1)...(2)
<223> OTHER INFORMATION: Xaa=undetermined residue
<220> FEATURE:
<221> NAME/KEY: SITE
<222> LOCATION: (7)...(7)
<223> OTHER INFORMATION: Thr residue was determined to be the most
     likely or "best-guess" at this position
<220> FEATURE:
<221> NAME/KEY: SITE
<222> LOCATION: (15)...(15)
<223> OTHER INFORMATION: Xaa=undetermined residue
<220> FEATURE:
<221> NAME/KEY: SITE
<222> LOCATION: (19)...(19)
<223> OTHER INFORMATION: Xaa=Ser residue was determined to be the most
     likely or "best-guess" at this position

<400> SEQUENCE: 6

Xaa Xaa Leu Pro Val Ala Thr Pro Asp Pro Gly Met Phe Pro Xaa Leu
1               5                 10                15

His His Ser Gln
          20

<210> SEQ ID NO 7
<211> LENGTH: 23
<212> TYPE: PRT
<213> ORGANISM: Homo sapiens

<400> SEQUENCE: 7

Ile Trp Glu Leu Lys Lys Asp Val Tyr Val Val Glu Leu Asp Trp Tyr
1               5                 10                15

Pro Asp Ala Pro Gly Glu Met
          20

<210> SEQ ID NO 8
<211> LENGTH: 6
<212> TYPE: PRT
<213> ORGANISM: Homo sapiens

<400> SEQUENCE: 8

Asn Lys Thr Phe Leu Arg
1               5

<210> SEQ ID NO 9
<211> LENGTH: 19
<212> TYPE: PRT
<213> ORGANISM: Homo sapiens
<220> FEATURE:
<221> NAME/KEY: SITE
<222> LOCATION: (10)...(10)
<223> OTHER INFORMATION: Xaa=undetermined residue

<400> SEQUENCE: 9

Gly Ser Ser Asp Pro Gln Gly Val Thr Xaa Gly Ala Ala Thr Leu Ser
1               5                 10                15

Ala Glu Arg

```
<210> SEQ ID NO 10
<211> LENGTH: 13
<212> TYPE: PRT
<213> ORGANISM: Homo sapiens
<220> FEATURE:
<221> NAME/KEY: SITE
<222> LOCATION: (12)...(12)
<223> OTHER INFORMATION: Xaa=undetermined residue

<400> SEQUENCE: 10

Val Phe Thr Asp Lys Thr Ser Ala Thr Val Ile Xaa Arg
1               5                   10

<210> SEQ ID NO 11
<211> LENGTH: 7
<212> TYPE: PRT
<213> ORGANISM: Homo sapiens

<400> SEQUENCE: 11

Thr Leu Thr Ile Gln Val Lys
1               5

<210> SEQ ID NO 12
<211> LENGTH: 11
<212> TYPE: PRT
<213> ORGANISM: Homo sapiens

<400> SEQUENCE: 12

Asn Leu Gln Leu Lys Pro Leu Lys Asn Ser Arg
1               5                   10

<210> SEQ ID NO 13
<211> LENGTH: 6
<212> TYPE: PRT
<213> ORGANISM: Homo sapiens

<400> SEQUENCE: 13

Ile Trp Glu Leu Lys Lys
1               5

<210> SEQ ID NO 14
<211> LENGTH: 8
<212> TYPE: PRT
<213> ORGANISM: Homo sapiens

<400> SEQUENCE: 14

Ala Gln Asp Arg Tyr Tyr Ser Ser
1               5

<210> SEQ ID NO 15
<211> LENGTH: 17
<212> TYPE: PRT
<213> ORGANISM: Homo sapiens

<400> SEQUENCE: 15

Lys Glu Asp Gly Ile Trp Ser Thr Asp Ile Leu Lys Asp Gln Lys Glu
1               5                   10                  15

Pro

<210> SEQ ID NO 16
<211> LENGTH: 13
<212> TYPE: PRT
<213> ORGANISM: Homo sapiens
<220> FEATURE:
<221> NAME/KEY: SITE
```

<222> LOCATION: (5)...(5)
<223> OTHER INFORMATION: Xaa=undetermined residue
<220> FEATURE:
<221> NAME/KEY: SITE
<222> LOCATION: (13)...(13)
<223> OTHER INFORMATION: Xaa=Arg residue was determined to be the most
      likely or "best-guess" at this position

<400> SEQUENCE: 16

Leu Lys Tyr Glu Xaa Tyr Thr Ser Ser Phe Phe Ile Arg
1               5                   10

<210> SEQ ID NO 17
<211> LENGTH: 12
<212> TYPE: PRT
<213> ORGANISM: Homo sapiens
<220> FEATURE:
<221> NAME/KEY: SITE
<222> LOCATION: (6)...(6)
<223> OTHER INFORMATION: Xaa=undetermined residue

<400> SEQUENCE: 17

Lys Glu Asp Gly Ile Xaa Ser Thr Asp Ile Leu Lys
1               5                   10

<210> SEQ ID NO 18
<211> LENGTH: 18
<212> TYPE: PRT
<213> ORGANISM: Homo sapiens
<220> FEATURE:
<221> NAME/KEY: SITE
<222> LOCATION: (12)...(12)
<223> OTHER INFORMATION: Xaa=undetermined residue
<220> FEATURE:
<221> NAME/KEY: SITE
<222> LOCATION: (17)...(18)
<223> OTHER INFORMATION: Xaa=undetermined residue

<400> SEQUENCE: 18

Ala Gln Asp Arg Tyr Tyr Ser Ser Ser Trp Glu Xaa Ala Ser Val Pro
1               5                   10                  15

Xaa Xaa

<210> SEQ ID NO 19
<211> LENGTH: 15
<212> TYPE: PRT
<213> ORGANISM: Homo sapiens
<220> FEATURE:
<221> NAME/KEY: SITE
<222> LOCATION: (1)...(1)
<223> OTHER INFORMATION: Xaa=Gly residue was determined to be the most
      likely or "best-guess" at this position
<220> FEATURE:
<221> NAME/KEY: SITE
<222> LOCATION: (12)...(12)
<223> OTHER INFORMATION: Xaa=Leu residue was determined to be the most
      likely or "best-guess" at this position

<400> SEQUENCE: 19

Gly Gly Glu Val Leu Ser His Ser Leu Leu Leu Leu His Lys Lys
1               5                   10                  15

<210> SEQ ID NO 20
<211> LENGTH: 9
<212> TYPE: PRT
<213> ORGANISM: Homo sapiens

<400> SEQUENCE: 20

Leu Lys Lys Asp Val Tyr Val Val Glu
1               5

<210> SEQ ID NO 21
<211> LENGTH: 10
<212> TYPE: PRT
<213> ORGANISM: Homo sapiens

<400> SEQUENCE: 21

Leu Asp Trp Tyr Pro Asp Ala Pro Gly Glu
 1               5                  10

<210> SEQ ID NO 22
<211> LENGTH: 14
<212> TYPE: PRT
<213> ORGANISM: Homo sapiens
<220> FEATURE:
<221> NAME/KEY: SITE
<222> LOCATION: (14)...(14)
<223> OTHER INFORMATION: Xaa=Glu residue was determined to be the most
      likely or "best-guess" at this position

<400> SEQUENCE: 22

Val Leu Gly Ser Gly Lys Thr Leu Thr Ile Gln Val Lys Glu
 1               5                  10

<210> SEQ ID NO 23
<211> LENGTH: 26
<212> TYPE: PRT
<213> ORGANISM: Homo sapiens
<220> FEATURE:
<221> NAME/KEY: SITE
<222> LOCATION: (1)...(1)
<223> OTHER INFORMATION: Xaa=undetermined residue
<220> FEATURE:
<221> NAME/KEY: SITE
<222> LOCATION: (15)...(15)
<223> OTHER INFORMATION: Xaa=undetermined residue

<400> SEQUENCE: 23

Xaa Asn Leu Pro Val Ala Thr Pro Asp Pro Gly Met Phe Pro Xaa Leu
 1               5                  10                  15

His His Ser Gln Asn Leu Leu Arg Ala Val
            20                  25

<210> SEQ ID NO 24
<211> LENGTH: 9
<212> TYPE: PRT
<213> ORGANISM: Homo sapiens

<400> SEQUENCE: 24

Asp Ile Ile Lys Pro Asp Pro Pro Lys
 1               5

<210> SEQ ID NO 25
<211> LENGTH: 24
<212> TYPE: PRT
<213> ORGANISM: Homo sapiens
<220> FEATURE:
<221> NAME/KEY: SITE
<222> LOCATION: (11)...(11)
<223> OTHER INFORMATION: Xaa=undetermined residue
<220> FEATURE:
<221> NAME/KEY: SITE
<222> LOCATION: (15)...(15)
<223> OTHER INFORMATION: Xaa=Ser residue was determined to be the most
      likely or "best-guess" at this position

<400> SEQUENCE: 25

Val Asp Ala Val His Lys Leu Lys Tyr Glu Xaa Tyr Thr Ser Ser Phe
 1               5                  10                  15

```
Phe Ile Arg Asp Ile Ile Lys Pro
            20

<210> SEQ ID NO 26
<211> LENGTH: 23
<212> TYPE: DNA
<213> ORGANISM: Artificial Sequence
<220> FEATURE:
<223> OTHER INFORMATION: forward primer
<220> FEATURE:
<221> NAME/KEY: modified_base
<222> LOCATION: (15)...(15)
<223> OTHER INFORMATION: n=undetermined base

<400> SEQUENCE: 26
ctcgaattcg arytnaaraa rga                                              23

<210> SEQ ID NO 27
<211> LENGTH: 24
<212> TYPE: DNA
<213> ORGANISM: Artificial Sequence
<220> FEATURE:
<223> OTHER INFORMATION: reverse primer
<220> FEATURE:
<221> NAME/KEY: modified_base
<222> LOCATION: (1)...(24)
<223> OTHER INFORMATION: n=undetermined base

<400> SEQUENCE: 27
ctcgaattcn ggngcrtcng grta                                             24

<210> SEQ ID NO 28
<211> LENGTH: 36
<212> TYPE: DNA
<213> ORGANISM: Artificial Sequence
<220> FEATURE:
<223> OTHER INFORMATION: oligonucleotide

<400> SEQUENCE: 28
gagctaaaga aagatgttta tgtcgtagaa ttggat                                36

<210> SEQ ID NO 29
<211> LENGTH: 36
<212> TYPE: DNA
<213> ORGANISM: Artificial Sequence
<220> FEATURE:
<223> OTHER INFORMATION: oligonucleotide

<400> SEQUENCE: 29
aggggcatcc ggataccaat ccaattctac gacata                                36

<210> SEQ ID NO 30
<211> LENGTH: 23
<212> TYPE: DNA
<213> ORGANISM: Artificial Sequence
<220> FEATURE:
<223> OTHER INFORMATION: forward primer
<220> FEATURE:
<221> NAME/KEY: modified_base
<222> LOCATION: (15)...(15)
<223> OTHER INFORMATION: n=undetermined base
<220> FEATURE:
<221> NAME/KEY: modified_base
<222> LOCATION: (18)...(18)
<223> OTHER INFORMATION: n=undetermined base

<400> SEQUENCE: 30
ctcgaattcg ayccnggnat gtt                                              23
```

```
<210> SEQ ID NO 31
<211> LENGTH: 24
<212> TYPE: DNA
<213> ORGANISM: Artificial Sequence
<220> FEATURE:
<223> OTHER INFORMATION: reverse primer
<220> FEATURE:
<221> NAME/KEY: modified_base
<222> LOCATION: (1)...(24)
<223> OTHER INFORMATION: n=undetermined base

<400> SEQUENCE: 31
ctcgaattcn gcncknarna rrtt                                          24

<210> SEQ ID NO 32
<211> LENGTH: 34
<212> TYPE: DNA
<213> ORGANISM: Artificial Sequence
<220> FEATURE:
<223> OTHER INFORMATION: oligonucleotide

<400> SEQUENCE: 32
gatccgggaa tgttcccatg ccttcaccac tccc                               34

<210> SEQ ID NO 33
<211> LENGTH: 35
<212> TYPE: DNA
<213> ORGANISM: Artificial Sequence
<220> FEATURE:
<223> OTHER INFORMATION: oligonucleotide

<400> SEQUENCE: 33
agcccgtagg aggttttggg agtggtgaag gcatg                              35

<210> SEQ ID NO 34
<211> LENGTH: 30
<212> TYPE: DNA
<213> ORGANISM: Artificial Sequence
<220> FEATURE:
<223> OTHER INFORMATION: oligonucleotide

<400> SEQUENCE: 34
ctgaagccat taaagaattc tcggcaggtg                                    30

<210> SEQ ID NO 35
<211> LENGTH: 20
<212> TYPE: PRT
<213> ORGANISM: Homo sapiens
<220> FEATURE:
<223> OTHER INFORMATION: Positions 1 - 20 of purified 40 kDa protein SEQ
      ID NO: 1

<400> SEQUENCE: 35

Ile Trp Glu Leu Lys Lys Asp Val Tyr Val Val Glu Leu Asp Trp Tyr
 1               5                   10                  15

Pro Asp Ala Pro
            20

<210> SEQ ID NO 36
<211> LENGTH: 5
<212> TYPE: PRT
<213> ORGANISM: Homo sapiens
<220> FEATURE:
<223> OTHER INFORMATION: Positions 3 - 7 of purified 40 kDa protein SEQ
      ID NO: 1

<400> SEQUENCE: 36
```

Glu Leu Lys Lys Asp
1               5

<210> SEQ ID NO 37
<211> LENGTH: 5
<212> TYPE: PRT
<213> ORGANISM: Homo sapiens
<220> FEATURE:
<223> OTHER INFORMATION: Positions 38-42 of purified 40 kDa protein SEQ
      ID NO: 1

<400> SEQUENCE: 37

Tyr Pro Asp Ala Pro
1               5

<210> SEQ ID NO 38
<211> LENGTH: 7
<212> TYPE: PRT
<213> ORGANISM: Homo sapiens
<220> FEATURE:
<223> OTHER INFORMATION: Positions 1 - 7 of purified 40 kDa protein SEQ
      ID NO: 1

<400> SEQUENCE: 38

Ile Trp Glu Leu Lys Lys Asp
1               5

<210> SEQ ID NO 39
<211> LENGTH: 5
<212> TYPE: PRT
<213> ORGANISM: Homo sapiens

<400> SEQUENCE: 39

Asp Pro Gly Met Phe
1               5

<210> SEQ ID NO 40
<211> LENGTH: 7
<212> TYPE: PRT
<213> ORGANISM: Homo sapiens

<400> SEQUENCE: 40

Arg Asn Leu Pro Val Ala Thr
1               5

<210> SEQ ID NO 41
<211> LENGTH: 7
<212> TYPE: PRT
<213> ORGANISM: Homo sapiens
<220> FEATURE:
<221> NAME/KEY: SITE
<222> LOCATION: (1)...(1)
<223> OTHER INFORMATION: Xaa=undetermined residue

<400> SEQUENCE: 41

Xaa Asn Leu Pro Val Ala Thr
1               5

<210> SEQ ID NO 42
<211> LENGTH: 5
<212> TYPE: PRT
<213> ORGANISM: Homo sapiens

<400> SEQUENCE: 42

Asn Leu Leu Arg Ala
1               5

```
<210> SEQ ID NO 43
<211> LENGTH: 12
<212> TYPE: PRT
<213> ORGANISM: Homo sapiens

<400> SEQUENCE: 43

Leu Pro Val Ala Thr Pro Asp Pro Gly Met Phe Cys
 1               5                  10
```

PURIFICATION AND CHARACTERIZATION OF CYTOTOXIC LYMPHOCYTE MATURATION FACTOR AND MONOCLONAL ANTIBODIES THERETO

This is a Continuation of application Ser. No. 09/401,839, filed Sep. 22, 1999, which is a Divisional of application Ser. No. 08/459,151, filed Jun. 2, 1995, now U.S. Pat. No. 6,683,046 which is a Divisional of application Ser. No. 08/205,011, filed Mar. 2, 1994, now abandoned, which is a Divisional of application Ser. No. 07/857,023, filed Mar. 24, 1992, now abandoned, which is a Continuation-In-Part of application Ser. No. 07/572,284, filed Aug. 27, 1990 now abandoned, which is a Continuation-In-Part of application Ser. No. 07/520,935, filed May 9, 1990, now abandoned, which is a continuation-in-part of application Ser. No. 07/455,708, filed Dec. 22, 1989, now abandoned, the contents of each of which is incorporated herein by reference in its entirety.

FIELD OF THE INVENTION

The present invention relates to the field of cytokines, in particular to those cytokines which synergize with Interleukin-2 (IL-2) to activate cytotoxic lymphocytes.

BACKGROUND OF THE INVENTION

'Cytokine' is one term for a group of protein cell regulators, variously called lymphokines, monokines, interleukins and interferons, which are produced by a wide variety of cells in the body, play an important role in many physiological responses, are involved in the pathophysiology of a range of diseases, and have therapeutic potential. This heterogeneous group of proteins has the following characteristics in common. They are low molecular weight ($\leq 80$ kDa) secreted proteins which are often glycosylated; are involved in immunity and inflammation where they regulate the amplitude and duration of a response; and are usually produced transiently and locally, acting in a paracrine or autocrine, rather than endocrine manner. Cytokines are extremely potent, generally acting at picomolar concentrations; and interact with high affinity cell surface receptors specific for each cytokine or cytokine group. Their cell surface binding ultimately leads to a change in the pattern of cellular RNA and protein synthesis, and to altered cell behavior. Individual cytokines have multiple overlapping cell regulatory actions.

The response of a cell to a given cytokine is dependent upon the local concentration of the cytokine, the cell type and other cell regulators to which it is concomitantly exposed. The overlapping regulatory actions of these structurally unrelated proteins binding to different cell surface receptors is at least partially accounted for by the induction of common proteins which can have common response elements in their DNA. Cytokines interact in a network by: first, inducing each other; second, transmodulating cytokine cell surface receptors and third, by synergistic, additive or antagonistic interactions on cell function. [*Immunology Today* 10 No. 9 p 299 (1989)].

The potential utility of cytokines in the treatment of neoplasia and as immunoenhancing agents has recently been demonstrated in studies using human recombinant interleukin-2 (rIL-2). Natural Interleukin-2 (IL-2) is a lymphokine which is produced and secreted by T-lymphocytes. This glycoprotein molecule is intimately involved in the induction of virtually all immune responses in which T-cells play a role. B cell responses in vitro are also enhanced by the presence of IL-2, and IL-2 has also been implicated as a differentiation inducing factor in the control of B and T lymphocyte responses.

Administration of human rIL-2 has been shown in some cases to result in regression of established tumors in both experimental animals [J. Exp. Med 161:1169-1188, (1985)] and in man [(N. Engl. J. Med 313:1485-1492, (1985) and N. Engl. J. Med 316:889-897 (1987)]. The anti-tumor effects of rIL-2 are thought to be mediated by host cytotoxic effector lymphocytes which are activated by rIL-2 in vivo [J. Immunol. 139:285-294 (1987)]. In addition, results from animal models suggest that rIL-2 might also have value in the treatment of certain infectious diseases [J. Immunol. 135:4160-4163 (1985) and J. Virol. 61:2120-2127 (1987)] and in ameliorating chemotherapy-induced immunosuppression [Immunol Lett. 10:307-314 (1985)].

However, the clinical use of rIL-2 has been complicated by the serious side effects which it may cause [N. Engl. J. Med. 313:1485-1492 (1985) and N. Engl. J. Med. 316:889-897 (1987)]. One approach to improving the efficacy of cytokine therapy while reducing toxicity is to use two or more cytokines in combination. For example, synergistic antitumor activity has been shown to result when rIL-2 is administered to tumor-bearing mice together with recombinant interferon alpha (rIFN alpha) [Cancer Res. 48:260-264 (1988) and Cancer Res. 48:5810-5817 (1988)] or with recombinant tumor necrosis factor alpha (rTNF alpha) [Cancer Res. 47:3948-3953 (1987)]. Since the antitumor effects of IL2 are thought to be mediated by host cytotoxic effector lymphocytes, it would be of interest to identify and isolate novel cytokines which synergize with rIL2 to activate cytotoxic lymphocytes a vitro. These novel cytokines would also be useful as anti-tumor agents when administered in combination with rIL2 a vivo.

SUMMARY OF THE INVENTION

The present invention is a novel cytokine protein called Cytotoxic Lymphocyte Maturation Factor (CLMF) also called IL-12 which is produced and synthesized by cells capable of secreting CLMF such as mammalian cells particularly human NC-37 B lymphoblastoid cells (ATCC CCL 214 American Type Culture Collection, Rockville, MD). CLMF synergistically induces with low concentrations of IL-2 (IL-2) the cytolytic activity of Lymphokine Activated Killer (LAK) cells, and CLMF is capable of stimulating T-cell growth.

The present invention is directed toward the process of isolating CLMF in a substantially pure form.

The process comprises the following:
stimulating NC-37 B lymphoblastoid cells to produce and secrete cytokines into a supernatant liquid;
collecting the supernatant liquid produced by the stimulated cells;
separating the supernatant liquid into protein fractions;
testing each protein fraction for the presence of CLMF;
retaining the protein fractions which are able to stimulate T-cell growth, said fractions containing an active protein which is responsible for the T-cell stimulating activity of the protein fractions;
isolating said active protein into a substantially pure form, said protein being cytolytic Lymphocyte Maturation Factor (CLMF). CLMF is a 75 kilodalton (kDa) heterodimer comprised of two polypeptide subunits, a 4.0 kDa subunit and a 35 kDa subunit which are bonded together via one or more disulfide bonds.

The process of this invention is capable of purifying CLMF from any liquid or fluid which contains CLMF together with other proteins. Also claimed are the protein fractions capable of stimulating T-cell growth, the substantially purified active protein, CLMF, obtained from the above-described process, the isolated cloned genes encoding the 40 kDa subunit and the 35 kDa subunit, vectors, containing these genes and host cells transformed with the vectors containing the genes.

In addition a method for stimulating LAK cells and T-cells comprised of treating these cells with CLMF alone or with IL-2 is claimed, Also claimed are isolated antibodies capable of binding to CLMF.

Antibodies to CLMF

Monoclonal antibodies prepared against a partially purified preparation of CLMF have been identified and characterized by 1: immunoprecipitation of $^{125}$I-labelled CLMF, 2: immunodepletion of CLMF bioactivity, 3: western blotting of CLMF, 4: inhibition of $^{125}$I-CLMF binding to its cellular receptor and 5: neutralization of CLMF bioactivity. Twenty hybridomas were identified which secreted anti-CLMF antibodies. The antibodies immunoprecipitate $^{125}$I-labelled CLMF and immunodeplete CLMF bioactivity as assessed in the T-cell proliferation and LAK cell induction assays. Western blot analysis demonstrate that each antibody binds to the 70 kDa heterodimer and to the 40 kDa subunit. These data demonstrated that the 20 antibodies were specific for CLMF and in particular for the 40 kDa subunit of CLMF. A CLMF receptor binding assay has been developed to evaluate the ability of individual antibodies to inhibit CLMF binding to its cellular receptor. The assay measures the binding of $^{125}$I-labelled CLMF to PHA activated PBL blast cells in the presence and absence of each antibody. Of the 20 antibodies tested, 12 antibodies inhibit greater than 60% of the $^{125}$I-labeled CLMF binding to the blast cells. Two inhibitory antibodies, 7B2 and 4A I, neutralize CLMF bioactivity while one non-inhibitory antibody, 8E3, does not neutralize CLMF bioactivity. These data confirm that antibodies which block $^{125}$I-labelled CLMF binding to its cellular receptor will neutralize CLMF bioactivity as assessed by the T-cell proliferation and LAK cell induction assays. The ability of the antibodies specific for the 40 kDa subunit of CLMF to neutralize CLMF bioactivity indicates that determinants on the 40 kDa subunit are necessary for binding to the CLMF cellular receptor.

Utility for the Monoclonal Anti-Human CLMF Antibodies

The monoclonal anti-CLMF antibodies provide powerful analytical, diagnostic and therapeutic reagents for the immunoaffinity purification of natural and recombinant human CLMF, the development of human CLMF immunoassays, the identification of the active site of the 40 kDa subunit of CLMF and as possible therapeutic treatments which require selective immunosuppression of cytotoxic T cells, such as in transplantation. Monoclonal antibodies which recognize different epitopes on human CLMF can be used as reagents in a sensitive two-site immunoassay to measure levels of CLMF in biological fluids, cell culture supernatants and human cell extracts.

The present invention is directed to monoclonal antibodies against CLMF which exhibit a number of utilities including but not limited to:

1. Utilizing the monoclonal antibodies as affinity reagents for the purification of natural and recombinant human CLMF;

2. Utilizing the monoclonal antibodies as reagents to configure enzyme-immunoassays and radioimmunoassays to measure natural and recombinant CLMF in biological fluids, cell culture supernatants, cell extracts and on plasma membranes of human cells and as reagents for a drug screening assay;

3. Utilizing the monoclonal antibodies as reagents to construct sensitive two-site immunoassays to measure CLMF in biological fluids, cell culture supernatants and human cell extracts;

4. Utilizing the monoclonal antibodies as reagents to identify determinants of the 40 kDa subunit which participate in binding to the 35 kDa subunit and which participate in binding to the CLMF cellular receptor;

5. Utilizing the intact IgG molecules, the Fab fragments or the humanized IgG molecules of the inhibitory monoclonal antibodies as therapeutic drugs for the selective blockade of proliferation and activation of cytotoxic T cells, such as in transplantation.

BRIEF DESCRIPTION OF THE DRAWINGS

FIG. 17 is a chart which summarizes the protein structural determination of the 40kDa subunit of CLMF (SEQ ID NO:1).

FIG. 25A-25D shows the DNA and deduced amino acid sequences for the 40 kDa subunit of CLMF (SEQ ID NO:2 and 3).

FIG. 26A-26C shows the cDNA sequence and deduced amino acid sequence for the human 35 kDa CLMF subunit (SEQ ID NO:4 and 5).

FIG. 32 shows Western blot analysis of the reactivity of monoclonal and rat polyclonal anti-CLMF antibodies with CLMF 40 kDa subunit.

A PBMC were cultured for 12 days in the presence of 10 ng/ml of IL-4 and increasing concentrations of IL-12 (0.1 to 100 pM). Shown are the mean ± 1 SEM of three experiments; *significantly different from control without IL-2 at P<0.01, Student's t test.

B. Cells were cultured in the presence of IL-4 and IL-12 (60 pM) with or without anti-IL-12 mAbs (a mixture of antibodies 4A1 and 20C2, each-at 10 µg/ml).

Figure 39:
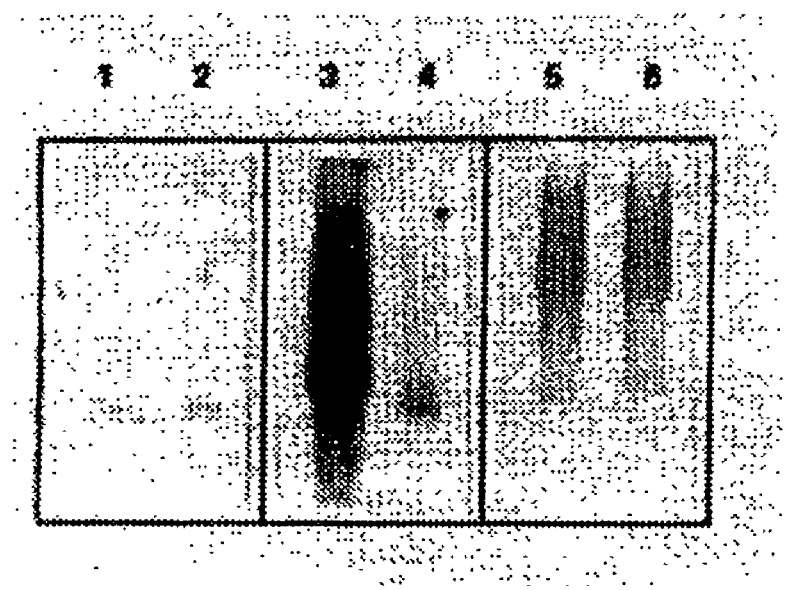

FIG. 39 shows that IL-12 suppresses the accumulation of productive but not germ-line Cε transcripts. Total RNA was extracted from PBMC cultured for 10 days with 10 ng/ml of IL-4; in the absence (lanes 1, 3 and 5) or in the presence of 60 pM IL-12 (lanes 2, 4, and 6). Northern blot was performed as described. The membrane was hybridized with $^{32}$P-labeled probes specific for the germ-line transcript (lanes 1 and 2) or for the Cε$_1$, -Cε$_2$ region binding to both germ-line and mature Cε transcripts (lanes 3 and 4). Equal loading was assessed by methylene blue staining of the ribosomal RNA (lanes 5 and 6).

DETAILED DESCRIPTION OF THE INVENTION

All publications mentioned herein, both supra and infra, are hereby incorporated herein by reference.

The CLMF (or IL-12) active proteins of the present invention include the homogenous natural CLMF protein as well as CLMF proteins which contain a biologically active fragment of the amino acid sequence of natural CLMF and CLMF proteins which contain the amino acid sequence of natural CLMF together with other amino acids. The proteins of this invention have the biological activity of CLMF as measured by standard assays such as T-cell growth factor assay as described in Example 9.

The protein of the present invention also include proteins which contain analogous amino acid sequences to CLMF or its CLMF active fragments. Such analogues are proteins in which one or more of the amino acids of natural CLMF or its fragments have been replaced or deleted without eliminating CLMF activity. Such analogues may be produced by known methods of peptide chemistry, or by known methods of recombinant DNA technology, such as planned mutagenesis. The CLMF biological activity of all of the proteins of the present invention including the fragments and analogues may be determined by using the standard T-cell growth factor assay such as described in Example 9.

In accordance with this present invention, natural CLMF is obtained in pure form. The amino acid sequence of this protein is depicted in FIGS. 25A-25D and 26A-26C. From the sequence of this protein obtained in accordance with this invention, biologically active analogues and fragments of this CLMF protein can be obtained. These biologically active proteins may be produced biologically through standard recombinant technology or may be chemically synthesized using the sequence described above and an amino acid synthesizer or manual synthesis using chemical conditions well known to form peptide bonds between selected amino acids. In this manner, these analogues, fragments and proteins which contain the amino acid sequence of CLMF together with other amino acids can be produced. All of these proteins may then be tested for CLMF activity.

Cytotoxic Lymphocyte Maturation Factor of the present invention was isolated and purified as follows:

Production of Supernatant Liquid Containing CLMF.

Human NC-37 B lymphoblastoid cells ATCC CCL 214 (American Type Culture Collection, Rockville, MD) were used for production of CLMF. These cells were maintained by serial passage in RPMI 1640 medium supplemented with 5% heat-inactivated (56° C., 30 min.) fetal bovine serum, 2 mM L-glutamine, 100 units/ml penicillin, and 100 μg/ml streptomycin (all obtained from GIBCO Laboratories, Grand Island, NY).

Higher producer sublines of NC-37 cells were derived by limiting dilution cloning in liquid microcultures. Each well of three Costar 3596® microplates (Costar Co:, Cambridge, MA) received 100 μl of a cell suspension containing five NC-37 cells/ml. The medium used for the cloning was a 1:1 mixture of fresh passage medium and filtered, conditioned medium from stock cultures of the parent NC-37 cells. One week and two weeks after culture initiation each of the microcultures was fed with 50 μl of the 1:1 mix of fresh and conditioned medium. Between 3 and 4 weeks after culture initiation the contents of wells containing clones of NC-37 cells were harvested and passed into larger cultures.

When the number of cells in a given subline exceeded $1.4 \times 10^6$, one million cells were stimulated to produce CLMF in 1 ml cultures containing 3 ng/ml phorbol 12-myristate 13-acetate (PMA) (Sigma Chemical Co., St. Louis, MO) and 100 ng/ml calcium ionophore A23187 (Sigma). Supernatants were harvested from the cultures after 2 days, dialyzed against about 50 volumes of Dulbecco's phosphate buffered saline (Gibco) using SPECTROPOR® #1 tubing (Fisher Scientific) overnight with one change of buffer and then for 4 hours against 50 volumes of RPMI 1640 medium with 50 μg/ml of gentamicin (both from Gibco) and tested for CLMF by means of the T cell growth factor assay (see below). Three sublines, NC-37.89, NC-37.98, and NC-37.102, were identified which routinely produced CLMF at titers >4 times the titers produced by the parent NC-37 cell line. Since cells from these three sublines produced CLMF at similar titers (>800 units/ml), culture supernatants derived from the three sublines were pooled for use as starting material for the purification of CLMF.

Bulk production of CLMF was carried out in roller bottle cultures on a roller apparatus set at about 38 rpms (Wheaton Cell Production Roller Apparatus Model II, Wheaton Instruments, Millville, NJ). Cell suspensions were prepared containing $1-1.5 \times 10^6$ NC-37.89, NC-37.98 or NC-37.102 cells/ml of RPMI 1640 supplemented with 1% Nutridoma-SP (Boehringer Mannheim Biochemicals, Indianapolis, IN), 2 mM L-glutamine, 100 units/ml penicillin, 100 μg/ml streptomycin, 10 ng/ml PMA and 20-25 ng/ml calcium ionophore A23187. Two hundred fifty to three hundred fifty ml aliquots of the cell suspensions were added to Falcon 3027 tissue culture roller bottles (Becton Dickinson, Lincoln Park, NJ) which had been gassed with a mixture of 5% $CO_2$, 95% air. The roller bottles were then capped tightly and incubated at 37° C. with continuous rolling for three days. At the end of this time, the culture supernatants were harvested. EDTA and phenylmethylsulfonyl fluoride (both from Boehringer Mannheim) were added to the culture supernatant at final concentrations of 1 mM and 0.1 mM, respectively, to retard proteolytic degradation. The supernatants were stored at 4° C. until concentration.

Lymphokine Activated Killer (LAK) Cell Induction (LCI) Assay.

Culture supernatants and chromatographic fractions were tested for their ability to synergize with rIL-2 to induce the generation of cytolytic LAK cells as follows. Human peripheral blood mononuclear cells (PBMC) were isolated by the following method. Blood from normal volunteer donors was drawn into syringes containing sufficient sterile preservative-free heparin (Sigma) to give a final concentration of approximately 5 units/ml. The blood was diluted 1:1 with Hanks' balanced salt solution (HBSS) without calcium or magnesium (GIBCO). The diluted blood was then layered over 15 ml aliquots of Ficoll/sodium diatrizoate solution (Lymphocyte Separation Medium, Organon Teknika Corp., Durham, N.C.) in 50 ml Falcon 2098 centrifuge tubes. The tubes were centrifuged for 30 minutes at room temperature at 500×g. Following centrifugation, the cells floating on the Ficoll/sodium diatrizoate layer were collected and diluted by mixing with $\geq 2$ volumes of HBSS without: calcium or magnesium. The resulting cell suspension was then layered over 15 ml aliquots of 20% sucrose (Fisher) in RPMI 1640 medium with 1% human AB serum (Irvine Scientific, Santa Ana, Calif.) in Falcon 2098 centrifuge tubes. The tubes were centrifuged for 10 minutes at room temperature at 500×g, and the supernatant fluids were discarded. The cell pellets were resuspended in 5 ml of HBSS without calcium or magnesium, repelleted by centrifugation, and finally resuspended in the appropriate culture medium; Accessory cells were removed from the PBMC by treatment with 5 mM L-glutamic acid dimethyl ester (Sigma) using the same conditions described by Thiele et al. J. Immunol. 131:2282-2290, (1983) for accessory cell depletion by L-leucine ethyl ester except that the glutamic acid ester was substituted for the leucine ester.

The accessory cell-depleted PBMC were further fractionated by centrifugation on a discontinuous Percoll density gradient (Pharmacia, Piscataway, N.J.) as described by Wong et al., Cell Immunol. 111:39-54, (1988). Mononuclear cells recovered from the 38, 41, 45, and 58% Percoll layers were pooled and used as a source of LAK cell precursors in the assay. The cells recovered from the Percoll gradient were washed and suspended in tissue culture medium (TCM) composed of a 1:1 mixture of RPMI 1640 and Dulbecco's modified Eagle's medium, supplemented with 0.1 mM nonessential amino acids, 60 μg/ml arginine HCl, 10 mM HEPES buffer, 2 mM L-glutamine, 100 units/ml penicillin, 100 μg/ml streptomycin (all available from GIBCO), $5 \times 10^{-5}$ M 2-mercaptoethanol (Fisher Scientific, Fair Lawn, N.J.), 1 mg/ml dextrose (Fisher), and 5% human AB serum (Irvine Scientific, Santa Ana, Calif.). These cells were incubated in 24-well tissue culture plates (Costar, Cambridge, Mass.) in 1 ml cultures ($7.5 \times 10^5$ cells/culture) to which $10^{-4}$ M hydrocortisone sodium succinate (Sigma) was added to minimize endogenous cytokine production. Some cultures also received human rIL-2 (supplied by Hoffmann-La Roche) at a final concentration of 5 units/ml and/or supernatants to be.assayed for CLMF activity. All cultures were incubated for 3.4 days at 37° C. in a humidified atmosphere of 5% $CO_2$, 95% air.

At the end of this incubation, the contents of each culture were harvested, and the cells were pelleted . by centrifugation and resuspended in 0.5 ml of fresh TCM. One tenth ml aliquots of these cell suspensions were mixed with 0.1 ml aliquots of $^{51}Cr$-labelled K562 or Raji cells (both cell lines obtained from the ATCC) and tested for their lytic activity in 5 hour $^{51}Cr$ release assays. The method for labelling target cells with $^{51}Cr$ W4 performing the cytolytic assays have been described by Gately et al., [JNCI 62:1245-1254 (1982)]. The percent specific $^{51}Cr$ release was calculated as $[(-c)/(100-c)] \times 100$, where e is the percentage of $^{51}Cr$ released from target cells incubated with lymphocytes and c is the percentage of $^{51}Cr$ released spontaeously from target cells incubated alone. The total releasable $^{51}Cr$ was determined by lysis of the target cells with 2% sodium dodecyl sulfate; see Gately et al., JNCI 69:1245-1254 (1982). All lymphocyte populations were assayed in quadruplicate for lytic activity.

LAK Cell Induction Microassay. The microassay for measuring synergy between rIL-2 and CLMF-containing solutions in the induction of human LAK cells was similar to the LAK cell induction assay described above but with the following modifications. Human peripheral blood mononuclear cells which had been depleted of accessory cells and fractionated by Percoll gradient centrifugation as described above were added to the wells of Costar 3596 microplates ($5 \times 10^4$ cells/well). Some of the wells also received rIL-2 (5 units/ml final concentration) and/or purified CLMF or immunodepleted CLMF-containing solutions. All cultures contained $10^{-4}$ M hydrocortisone sodium succinate (Sigma) and were brought to a total volume of 0.1 ml by addition of TCM with 5% human AB serum. The cultures were incubated for 3 days at 37° C., after which 0.1 ml of $^{51}$Cr-labelled K562 cells ($5 \times 10^4$ cells/ml TCM with 5% human AB serum) were added to each well. The cultures were then incubated overnight at 37° C. Following this, the cultures were centrifuged for 5 minutes at 500 ×g, and the supernatant solutions were harvested by use of a Skatron supernatant collection system (Skatron, Sterling, VA). The amount of $^{51}$Cr released into each) supernatant solution was measured with a gamma counter (Packard, Downer's Grove, IL), and the % specific $^{51}$Cr release was calculated as described above. All samples were assayed in quadruplicate.

Cytolytic T Lymphocyte (CTL) Generation Assay.

Methods used for generating and measuring the lytic activity of human CTL have been described in detail in Gately et al., J. Immunol. 136:1274-1282, 1986, and Wong et al., Cell Immunol. 111:39-54, 1988. Human peripheral blood mononuclear cells were isolated from the blood of normal volunteer donors, depleted of accessory cells by treatment with L-glutamic acid dimethyl ester, and fractioned by Percoll gradient centrifugation as described above. High density lymphocytes recovered from the interface between the 45% and 58% Percoll layers were used as responder lymphocytes in mixed lymphocyte-tumor cultures (MLTC). CTL were generated in MLTC in 24-well tissue culture plates (Costar #3424) by incubation of Percoll gradient-derived high density lymphocytes ($7.5 \times 10^5$/culture) together with $1 \times 10^5$ uv-irradiated HT144 melanoma cells (ATCC, Rockville, MD) or with $5 \times 10^4$ gamma-irradiated HT144 melanoma cells in TCM with 5% human AB serum (1.2 ml/culture). For uv-irradiation, HT144 cells were suspended at a density of $1-1.5 \times 10^6$ cells/ml in Hanks' balanced salt solution without phenol red (GIBCO) containing 1% human AB serum. One ml aliquots of the cell suspension were added to 35×10 mm plastic tissue culture dishes (Falcon #3001), and the cells were then irradiated (960 µW/cm$^2$ for 5 min) by use of a 254 nm uv light (model UVG-54 MINERALIGHT® lamp, Ultraviolet Products, Inc., San Gabriel, CA). For gamma irradiation, HT144 cells were suspended at a density of $1-5 \times 10^6$ cells/ml in TCM with 5% human AB serum and irradiated (10,000 rad) by use of a cesium source irradiator (model 143, J.L. Shepherd and Associates, San Fernando; CA). Uv- or gamma-irradiated HT144 were centrifuged and resuspended in TCM with 5% human AB serum at the desired cell density for addition to the MLTC. In addition to lymphocytes and melanoma cells, some MLTC received human rIL-2 and/or purified human CLMF at the concentrations indicated in the table. Hydrocortisone sodium succinate (Sigma) was added to the MLTC at a final concentration of $10^{-4}$ M (cultures containing uv-irradiated melanoma cells) or $10^{-5}$M (cultures containing gamma-irradiated melanoma cells) to suppress endogenous cytokine production [S. Gillis et al., J. Immunol. 123: 1624-1631, 1979] and to reduce the generation of non-specific LAK cells in the cultures [L.M. Muul and M.L Gately, J. Immunol. 132: 1202-1207, 1984]. The cultures were incubated at 37° C. in a humidified atmosphere of 5% $CO_2$ to air for 6 days. At the end of this time, lymphocytes from replicate cultures were pooled, centrifuged, resuspended in 1.2 ml TCM containing 5% human AB serum, and tested for their ability to lyse HT144 melanoma cells, and, as a specificity control, K562 erythroleukemia cells in overnight $^{51}$Cr release assays.

Melanoma cells and K562 cells were labeled with $^{51}$Cr sodium chromate as described by Gately et al. (JNCI 69:1245-1254, 1982). Likewise, measurement of lymphocyte mediated lysis of $^{51}$Cr-labeled melanoma cells was performed in a manner identical to that described by Gately et al. (ibid.) for quantitating lysis of glioma target cells. For assaying the lysis of $^{51}$Cr-labeled K562 cells, 0.1 ml aliquots of lymphocyte suspensions were mixed with 25 µl aliquots of $^{51}$Cr-labeled K562 ($2 \times 10^5$ cells/ml in TCM with 5% human AB serum) in the wells of Costar 3696 "half-area" microtest plates. After overnight incubation at 37° C., the plates were centrifuged for 5 min at 1400×g, and 50 µl of culture medium was aspirated from each well. The amount of $^{51}$Cr in each sample was measured with a gamma counter (Packard), and the % specific $^{51}$Cr release was calculated as described above. All assays were performed in quadruplicate, and values in the table represent the means+1 S.E.M. of replicate samples.

T Cell Growth Factor (TGF) Assay.

The ability of culture supernatants and chromatographic fractions to stimulate the proliferation of PHA-activated human T lymphoblasts was measured as follows. Human PBMC were isolated by centrifugation over discontinuous Ficoll and sucrose gradients as described above for the LCI assay. The PBMC ($5 \times 10^5$ cells/ml) were cultured at 37° C. in TCNM containing 0.1% phytohemagglutinin-P (PHA-P) (Difco Laboratories, Detroit, Mich.). After 3 days, the cultures were split 1:1 with fresh TCM, and human rIL-2 was added to each culture to give a final concentration of 50 units/ml. The cultures were then incubated for an additional 1 to 2 days, at which time the cells were harvested, washed, and resuspended in TCM at $4 \times 10^5$ cells/ml. To this cell suspension was added heat-inactivated goat anti-human rIL-2 antiserum (final dilution: 1/200) to block any potential IL-2-induced cell proliferation in the assay. This antiserum-which was provided by R. Chizzonite, Molecular Genetics Department, Hoffmann-La Roche, was shown to cause 50% neutralization of 2 units/ml rIL-2 at a serum dilution of 1/20,000. An equally functional anti-human rIL2 antibody can be obtained from the Genzyme Co., Boston, Mass.

Fifty µl aliquots of the cell suspension containing anti-IL-2 antiserum were mixed with 50 µl aliquots of serial dilutions of culture supernatants or chromatographic fractions in the wells of Costar 3596 microplates. The cultures were incubated for 1 day at 37° C. in a humidified atmosphere of 5% $CO_2$ in air, and 50 µl of 3H-thymidine (New England Nuclear, Boston, Mass.), 10 µCi/ml in TCM, were then added to each well. The cultures were further incubated overnight. Subsequently, the culture contents were harvested onto glass fiber filters by means of a cell harvester (Cambridge Technology Inc., Cambridge, Mass.), and $^3$H-thymidine incorporation into cellular DNA was measured by liquid scintillation counting. All samples were assayed in triplicate.

In purifying CLMF it was necessary to define units of activity in order to construct chromatographic elution profiles and to calculate the percent recovery of activity and the specific activity of the purified material. To do this, a partially purified preparation of human cytokines produced by coculturing PHA-activated human PBMC with NC-37 cells was used as a standard. Several dilutions of this preparation, which was assigned an arbitrary titor of 2000 units/ml, were included in each TGF or LAK induction assay. The results obtained for the standard preparation were used construct a dose-response curve from which could be interpolated units/ml of activity in each unknown sample at the dilution tested. Multiplication of this value by the dilution factor yielded the activity of the original sample expressed in units/ml.

For antibody neutralization studies, the TGF assay was modified as follows: Twenty-five μl aliquots of CLMF-containing medium were mixed with 50 μl aliquots of serial dilutions of antiserum or antibody solutions in the wells of COSTAR 3596® microplates. The mixtures were incubated for 30 min. at 37° C., and 25 μl aliquots of a suspension of PHA-activated lymphoblasts ($8 \times 10^5$/ml in TCM plus 1:100 anti-rIL-2) were then added to each well. The cultures were further incubated, pulsed with $^3$H-thymidine, harvested, and analyzed for $^3$H-thymidine incorporation as described above.
Natural Killer (NK) Cell Activation Assay.

Purified CLMF was tested for its ability to activate NK cells when added alone or in combination with rIL-2 as follows: Human PBMC were isolated by centrifugation over discontinuous Ficoll and sucrose gradients as described above and were suspended in RPMI 1640 medium supplemented with 10% heat-inactivated fetal bovine serum, 100 units/ml penicillin, 100 μg/ml streptomycin, and 2 mM L-glutamine. The PBMC were incubated overnight at 37° C. in 1 ml cultures ($5 \times 10^6$ cells/culture) together with rIL-2 and/or purified CLMF at various concentrations. After 18-20 hours, the contents of the cultures were harvested and centrifuged, and the cells were resuspended in the same medium used for the overnight cultures. The cytolytic activity of the cultured PBMC was then-assessed in $^{51}$Cr release assays as described above.
Purification and Characterization of Cytotoxic Lymphocyte Maturation Factor (CLMF)
Concentration of Cell Supernatant Solutions Crude human QMF supernatant solutions prepared from several batches of induced NC-37 cells were pooled and concentrated 30-fold using the Pellicon Cassette System (30,000 NMWL PTTK00005; Millipore Spore Corp., Bedford, Mass.). After concentrating to the desired volume, a buffer exchange was performed with 10 mM MES, pH adjusted to 6.0 with 10 N NaOH. The concentrate was centrifuged at 10,000×g for 10 min at 4° C. and the precipitate discarded.
Ion-Exchange Chromatography on NuGel P-SP Column The concentrated supernatant solution was applied at a flow rate of 120 ml/hr to a NuGel P-SP (Separation Industries, Metuchen, N.J.) column (5×5 cm), equilibrated in 10 mM MES, pH 6.0. The column was washed until baseline absorbance monitoring at 280 nm was obtained. Absorbed proteins were then eluted with a 500 ml salt gradient from 0 to 0.5 M NaCt/10 mM MES, pH 6.0 at a flow rate of 2 ml/min. Aliquots of fractions were assayed for TGF activity. Fractions containing TGF activity were pooled and dialyzed (Spectra/Por 7, Fisher Scientific) against 50 vol 20 mM Tris/HCl, pH 7.5.
Dye-Affinity Chromatography on Blue B-Agarose Column The dialyzed sample was centrifuged at 10,000×g. for 10 min at 4° C. and the precipitate discarded. The supernatant solution was applied at a flow rate of 20 ml/hr to a Blue B-Agarose (Amicon, Danvers, Mass.) column (2.5×10 cm) equilibrated in 20 mM Tris/HCl, pH 7.5. The column was washed with this same buffer until baseline absorbance monitoring at 280 nm was obtained. Absorbed proteins were then eluted with a 500 ml salt gradient from 0 to 0.5 M NaCl/20 mM Tfls/HCl, pH 7.5 at a flow rate of 15 ml/hr. Aliquots of fractions were assayed for TGF activity. Fractions containing TGF activity were pooled and dialyzed (Spectra/Por 7, Fisher Scientific) against 100 vol 20 mM Tris/HCl, pH 7.5.
Ion-Exachange Chromatography on Mono Q Chromatography The dialyzed sample was filtered through a 0.45 μm cellulose acetate filter (Nalgene Co., Rochester, N.Y.) and the filtrate applied at a flow rate of 60 ml/hr to a Mono Q HR 515 (Pharmacia LKB Biotechnology, Inc., Piscataway, N.J.) column (5×50 mm) equilibrated in 20 mM Tris/HCl, pH 7.5. The column was washed with this same buffer until baseline absorbance monitoring at 280 nm was obtained. Absorbed proteins were then eluted with a 1 hr linear salt gradient from 0 to 0.25 M NaCl/20 mM Tris/HCl, pH 7.5 at a flow rate of 60 ml/hr. Aliquots of fractions were assayed for TGF activity and protein purity was assessed without reduction by SDS-PAGE [Laemmli, U. K. (1970) Nature (London) 227:680-685] using 12% slab gels. Gels were silver stained [Morrissey, Anal. Biochem. 117:307-310] to visualize protein. Fractions which did not contain a single band were further purified by reversed-phase HPLC.
Reversed-Phase HPLC The chromatographic system has been described previously by Stern, A. S. and Lewis, R. V. (1985) in Research Methods in Neurochemistry, Eds. Marks, N. and Rodnight, R. (Plenum, N.Y.) Vol. 6, 153-193. An automated fluorescence detection system using fluorescamine (Polysciences, Inc., Warrington, Pa.) monitored the protein in the column effluents [Stein, S. and Moschera, J. (1981) Methods Enzymol. 78:435-447]. Reversed-phase HPLC was carried out using Vydac C18 or diphenyl columns (4.6×20 mm, The Sep/a/ra/tions Group, Hesperia, Calif.). Proteins were eluted with an acetonitrile gradient in 0.1% TFA.
Protein Analysis Amino acid analysis was performed on an instrument which used post-column reaction with fluorescamine for detection [Pan, Y. C. E., and Stei, S. (1986) in Methods of Protein Microcharacterization (Shively, J. E., Ed.), pp. 105-119, Humana Press, Clifton, N.J.].

Sequence analysis was performed using an Applied Biosystems Inc. Model 470A gas phase sequencer (Foster City, Calif.) [Hewick, R. M., Henkapillar, M. W., Hood, L. E., and Dreyer, W. J. (1981) J. Biol. Chem. 256:7990-7997]. Phenylthiohydantoin (PTH) amino acid derivatives were identified "on-line" with an ABI Model 120A PTH analyzer.
Cloning of the CLMF Gene As used herein, the term "CLMF polynucleotide containing a sequence corresponding to a cDNA" means that the CLMF polynucleotide contains a sequence which is homologous to or complementary to a sequence in the designated DNA; the degree of homology or complementary to the cDNA will be approximately 50% or greater, will preferably be at least about 70%, and even more preferably will be at least about 90%. The correspondence between the CLMF sequences and the cDNA can be determined by techniques known in the art, including, for example, a direct comparison of the sequenced material with the cDNAs described, or hybridization and digestion with single strand nucleases, followed by size determination of the digested fragments.

The practice of the present invention will employ, unless otherwise indicated, conventional techniques of molecular biology, microbiology, recombinant DNA and immunogloy which are within the skill of the art. Such techniques are explained fully in the literature. See e.g., Maniatis, Fitsch & Sambrook, Molecular Cloning: A Laboratory Manual (1982); DNA cloning, Volumes I AND II (D. N Glover ed. 1985);.

Oligonucleotide Synthesis (M. J. Gait ed. 1984); Nucleic Acid Hybridization (B. D. Harnes & S. J. Higgins eds. 1984); Transcription and Translation (B. D. Harnes & S. J. Higgins eds. 1984); Animal Cell Culture (R. I. Freshney ed. 1986); Immobilized Cells and Enzymes (IRL Press, 1986); B. Perbal, A. Practical Guide to Molecular Cloning (1984); the series, Methods in Enzymology (Academic Press, Inc.); Gene Transfer Vectors for Mammalian Cells (J. H. Miller and M. P. Calos eds, 1987, Cold Spring Harbor Laboratory), Methods in Enzymology Vol. 154 and Vol. 155 (Wu and Grossman, and Wu, eds., respectively), Mayer and Walker, eds. (1987), Immunochemical Methods in cell and Molecular Biology: Academic Press, London), Scopes, (1987), Protein Purification: Principles and Practice, Second Edition (Springer-Verlag, N.Y.), and Handbook of Experimental Immunology, Volumes I-IV (D. M. Weir and C. C. Blackwell eds 1986).

The DNA sequences and DNA molecules of the present invention may be expressed using a wide variety of host/vector combinations. For example, useful vectors may consist of segments of chromosomal, non-chromosomal and synthetic DNA sequences, such as various known derivatives of SV-40 and known bacterial plasmids, e.g., plasmids from *E. coli* including pCRI, pBR322, pMB9 and RP4, phage DNAs, e.g., the numerous derivatives of phageg, and other DNA phages, e.g., M13 and other Filamentous single-stranded DNA phages, vectors useful in yeasts, such as the 2m plasmid, vectors useful in eukaryotic cells, such as vectors useful in animal cells, such as those containing SV-40 adenovirus and retrovirus derived DNA sequences and vectors derived from combinations of plasmids and phage DNA's, such as plasmids which have been modifiedto employ phage DNA or other derivatives thereof.

Such expression vectors are also characterized by at least one expression control sequence that may be operatively linked to the CLMF DNA sequence inserted in the vector in order to control and to regulate the expression of that cloned DNA sequenced Examples of useful expression control sequences are the lac system, the trp system, the tac system, the trc system, major operator and promoter regions of phage λ, the control region of fd coat protein, the glycolytic promoters of yeast, e.g., the promoter for 3-phosphoglycerate kinase, the promoters of yeast acid phosphatase, e.g., Pho 5, the promoters of the yeast a-mating factors, and promoters derived from polymoma, adenovirus, retrovirus, and simian virus, e.g., the early and late promoters or SV40, and other sequences known to control the expression of genes of prokaryotic or eukaryotic cells and their viruses or combinations thereof.

Among such useful expression vectors are vectors that enable the expression if the cloned CLMF-related DNA sequences in eukaryotic hosts, such as animal and human cells [e.g., P. J. Southern and P. Berg, *J. Mol. Appl. Genet.*, 1, pp. 327-41 (1982); S. Subramani et al., *Mol. Cell. Biol.*, 1, pp. 854-64 (1981); R. J. Kaufmann and P. A. Sharp, *Mol. Cell. Biol.*, 159, pp 601-64 (1982) S. I. Scahill et al., "Expression and Characterization of The Product Of A Human Immune Interferon DNA Gene in Chinese Hamster Ovary Cells", *Proc. Natl. Acad. Sci. U.S.A.*, 80, pp. 4654-59 (1983); G. Urlaub and L. A. Chasin, *Proc. Natl. Acad. Sci. USA*, 77, pp. 4216-20 (1989)].

Furthermore, within each specific expression vector, various sites may be selected for insertion of the CLMF-related DNA sequences of this invention. These sites are usually designated by the restriction endonuclease which cut them. They are well recognized by those of skill in the art. It is, of course to be understood that an expression vector useful in this invention need not have a restriction endonuclease site for insertion of the chosen DNA fragment. Instead, the vector could be joined to the fragment by alternative means. The expression vector, and in particular the site chosen therein for insertion of a selected DNA fragment and its operative linking therein to an expression control sequence, is determined by a variety of factors, e.g., number of sites susceptible to a particular restriction enzyme, susceptibility of the protein to proteolytic degradation by host cell enzymes, contamination of the protein to be expressed by host cell proteins difficult to remove during purification; expression characteristics, such as the location of start and stop codons relative to the vector sequences, and other factors recognized by those of skill in the art. The choice of a vector and an insertion site for a DNA sequence is determined by a balance of these factors, not all selections being equally effective for a given case.

Not all host/expression vector combinations function with equal efficieacy in expressing the DNA sequences of this invention or in producing the CLMF polypeptides of this invention. However, a particular selection of a host/expression vector combination may be made by those of skill in the art after due consideration of the principles set forth herein without departing from the scope of this invention. For example, the selection should be based on a balancing of a number of factors, These include, for example, compatibility of the host and vector, toxicity of the proteins encoded by the DNA sequence to the host, ease of recovery of the desired protein, expression characteristics of the DNA sequences and the expression control sequences operatively linked to them, biosafety, costs and the folding, form or any other necessary post-expression modifications of the desired protein.

The CLMF produced by fermentation of the prokaryotic and eukaryotic hosts transformed with the DNA sequences of this invention can then be employed in the LAK cell and T cell activator and antitumor compositions and methods of the present invention.

The CLMF of the present invention can also be analyzed to determine their active sites for producing fragments or peptides, including synthetic peptides, having the activity of CLMF. Among the known techniques for determining such active sites' are x-ray crystallography, nuclear magnetic resonance, circular dichroism, UV spectroscopy and site specific mutagenesis. Accordingly, these fragments may be employed in methods for stimulating T-cells or LAK cells.

Administration of the polypeptides, or perhaps peptides derived or synthesized from them or using their amino acid sequences, or their salts or pharmaceutically acceptable derivatives thereof, may be via any of the conventionally accepted modes of administration of agents which exhibit antitumor activity. These include parenteral, subcutaneous, intravenous, or intralesional administration.

The preferred form of administration depends on the intended mode of administration and therapeutic application. The compositions also will preferably include conventional pharmaceutically acceptable carriers and may include other medicinal agents, carriers, adjuvants, excipients, etc. e.g., human serum albumin or plasma preparations. Preferably, the compositions of the invention are in the form of a unit dose and will usually be administered one or more times a day.

Methods for Assay of Monoclonal Antibodies

Purification of CLMF and Labelling of CLMF with $^{125}$I. CLMF was partially purified from cell supernatants harvested from human peripheral blood lymphocytes (PBLs) or NC-37 cells as described previously. Partially purified CLMF was labelled with $^{125}$I by a modification of the Iodogen method (Pierce Chemical Co.). Jodogen (Pierce Chemical Co.) was dissolved in chloroform at a concentration of 0.5 mg/ml and 0.1 ml aliquots were added to 12×75 borosilicate glass tubes.

The chloroform was evaporated under a stream of nitrogen and the Iodogen was dried in the center of the bottom of the glass tube. The coated tubes were stored in a dessicator at room temperature (RT) under vacuum. For radiolabeling, 0.5-1.0 mCi $^{125}$I-Na (Amersham) was added to an Iodogen coated tube containing 0.50 ml of Tris-Iodination Buffer (25 mM Tris-HCl pH 7.5, 0.4 M NaCl, 1 mnM EDTA) and incubated for 4 minutes at RT. The activated $^{125}$I-solution was transferred to a 1.5 ml tube containing 0.05-0.1 ml° CLMF (approximately 5 μg in 0.125 M NaCl, 20 mM Tris-HCl pH 7.5) and the reaction was further incubated for 8 minutes at RT. At the end of the incubation, 0.05 ml of Iodogen Stop Buffer (10 mg/ml tyrosine, 10% glycerol in Dulbecco's phosphate buffered saline (PBS) pH 7.4) was added and reacted for 30 seconds. The mixture was then diluted with 1.0 ml Tris-Iodination Buffer and applied to a BioRad BioGel P10DG BioRad Laboratories) desalting column for chromatography. The column was eluted with Tris-Iodination Buffer and fractions (1 ml) containing the peak amounts of labelled protein were combined and diluted to $1 \times 10^8$ cpm/ml with 0.25% gelatin in Tri iodiation buffer. The TCA precipitable radioactivity (10% trichloroacetic acid final concentration) was typically in excess of 95% of the total radioactivity. The radiospecific activity ranged from 6000 cpm/fmol to 10,000 cpm/fmol.

Immunoadepletion of CLMF. Hybridoma culture supernatants or purified monoclonal antibodies were tested for their ability to immunodeplete CLMF as follows: Goat anti-rat IgG-agarose beads (Sigma Chemical Co., St. Louis, Mo.) were washed three times with 10 ml of PBS (Gibco) supplemented with 1% bovine serum albumin (BSA) (Sigma) (PBS/BSA solution). After washing, the beads were resuspended in PBS/BSA at a final concentration of 50% vol/vol. Aliquots (0.2 ml) of the bead suspension were added to 1.5 ml Eppendorf tubes, together with the indicated amounts of monoclonal antibodies or hybridoma supernatant solutions. The volume of each mixture was brought to 1.4 ml by the addition of hybridoma maintenance medium [Iscove's modified Dulbecco's medium (IMDM) with 0.1% fetal bovine serum (FBS), 10% Nutridoma-SP (Boehringer-Mannheim), and 2 mM L-glutamine], and the mixtures were then incubated for 2 hours at room temperature on a hematology/chemistry mixer. Following this incubation, the tubes were centrifuged in a Beckman microfuge 12 (1.5 minutes at setting 5), and the supernatants were discarded. The beads were again washed three times with PBS/BSA and then resuspended in 1 ml of tissue culture medium (TCM) containing 5% human AB serum and the indicated concentration of purified human CLMF. The tubes were subsequently incubated overnight at 4° C. on the mixer. Following this, the beads were removed by centrifugation in the microfuge, and the resulting immunodepleted supernatant solutions were assayed for residual CLMF activity in the TGF assay or in the microassay for LAK cell induction.

Immunoprecipitation Assay. For the immunoprecipitation reaction, 0.05 to 0.5 ml of hybridoma supernatant, diluted antisera or purified IgG was added to a 1.5 ml microfuge tube containing 0.1 ml of a 50% suspension of goat-anti-rat IgG coupled to agarose (Sigma Chemical Co.). The assay volume was brought up to 0.5 ml with RIPA Buffer (50 mM NaPO$_4$ pH 7.5, 150 mM NaCl, 1% Triton-X 100, 1% Deoxycholic acid, 0.1% SDS, 1% BSA, and 5 mM EDTA) and the mixture was incubated on a rotating mixer for 2 hours at RT. The beads were pelleted by centrifugation for 1 minute at 12,000×g and then resuspended in 1 ml RIPA Buffer containing $^{125}$I CLMF ($1 \times 10^5$ cpm). The mixture was then incubated on a rotating mixer for 16 hours at 4° C. Following this incubation, the beads were pelleted by centrifugation and washed 2× in RIPA without BSA. The beads were then washed 1× with 0.125 M Tris-HCl pH 6.8 and 10% glycerol.

The $^{125}$I-CLMF bound to the solid phase antibodies was released by adding 10 μl of 2× Laemmli Sample Buffer with and without 5%β-mercaptoethanol and heating for 3 minutes at 95° C. The immunoprecipitated $^{125}$I-CLMF was analyzed by SDS-PAGE on a 10% or 12% polyacrylamide gel and visualized by autoradiography.

CLMF Receptor Binding Assay. The ability of hybridoma supernatant solutions, purified IgG or antisera to inhibit the binding of $^{125}$I-CLMF to PHA-activated human T lymphoblasts was measured as follows: 0.1 ml aliquots of serial dilutions of culture supernatants, purified IgG or antisera were mixed with 0.025 ml aliquots of Binding Buffer (RPMI-1640, 5% FBS, 25 mM HEPES pH 7.4) containing $^{125}$I-CLMF ($1 \times 10^5$ cpm). The mixture was incubated on an orbital shaker for 1 hour at RT, then 0.025 ml of activated blasts ($5 \times 10^7$ cells/ml) was added to each tube. The mixture was further incubated for 1 hour at RT. Non-specific binding was determined by inclusion of 10 nM unlabelled CLMF in the assay. Incubations were carried out in duplicate or triplicate. Cell bound radioactivity was separated from free $^{125}$I-CLMF by centrifugation of the assay contents through 0.1 ml of an oil mixture (1:2 mixture of Thomas Silicone Fluid 6428-R15: A. H. Thomas, and Silicone Oil AR 200: Gallard-Schlessinger) at 4° C. for 90 seconds at 10,000×g. The tip containing the cell pellet was excised and cell bound radioactivity was determined in a gamma counter.

SDS Polyacrylamide Gel Electrophoresis (SDS/PAGE) and Western Blotting. Immunoprecipitated $^{125}$I-labelled proteins and partially purified CLMF were treated with Laemmli sample buffer (2% SDS, 125 mM Tris-HCl, pH 6.8, 10% glycerol, 0.025% bromphenol blue) with and without 5% β-mercaptoethanol, heated at 95° C. for 3 minutes and separated by SDS/PAGE on 7.5% or 12% precast gels (BioRad Laboratories). For the immunoprecipitated $^{125}$I-labelled proteins, the gels were stained with 0.2% Coomassie Brilliant Blue in 25% isopropyl alcohol and 10% acetic acid, destained in 10% methanol and 10% acetic acid, dried and analyzed by autoradiography. For western blotting, the proteins separated by SDS/PAGE were transferred to nitrocellulose membrane (0.2μ) for 16 hours at 100 volts in 10 mM Tris-HCl pH 8.3, 76.8 mM glycine, 20% methanol and 0.01% SDS. The nitrocellulose membrane was blocked for 1 hour at 37° C. in 3% gelatin, Tris-HCl pH 7.5, 0.15 M NaCl and then probed with hybridoma supernatant solutions or purified antibody diluted in AB buffer (1% bovine serum albumin, 50 mM sodium phosphate pH 6.5, 0.5 M NaCl, 0.05% Tween 20) for 16 hours at 4° C. After washing with wash buffer (PBS, 0.05% Tween 20), the nitrocellulose strips were incubated for 2 hours at room temperature with goat anti-rat IgG antibody coupled to peroxidase (Boehringer Mannheim Biochemicals) diluted in AB buffer. The nitrocellulose membrane was washed with wash buffer and the bound antibody visualized by incubation for 30 minutes at RT with 4-chloro-1-napthol (0.5 mg/ml in 0.15% H$_2$O$_2$, 0.5 M NaCl, 50 mM Tris-HCl, pH 7.5). The reaction was stopped by extensive washing with distilled water.

In order that our invention herein described may be more fully understood, the following examples are set forth. It should be understood that these examples are for illustrative purposes only and should not be construed as limiting this invention in any way to the specific embodiments recited therein.

EXAMPLE 1

Purification of CLMF

CLMF was produced by a subclone of NC-37 lymphoblastoid cells after costimulation with PMA and calcium ionophore A23187. Stored, frozen supernatant solutions from these cells totaling 60 liters were thawed, pooled and concentrated to approximately 1.9 liters using the Pellicon Cassette System. To clarify this concentrate, the preparation was centrifuged and the precipitate discarded.

Figure 1:
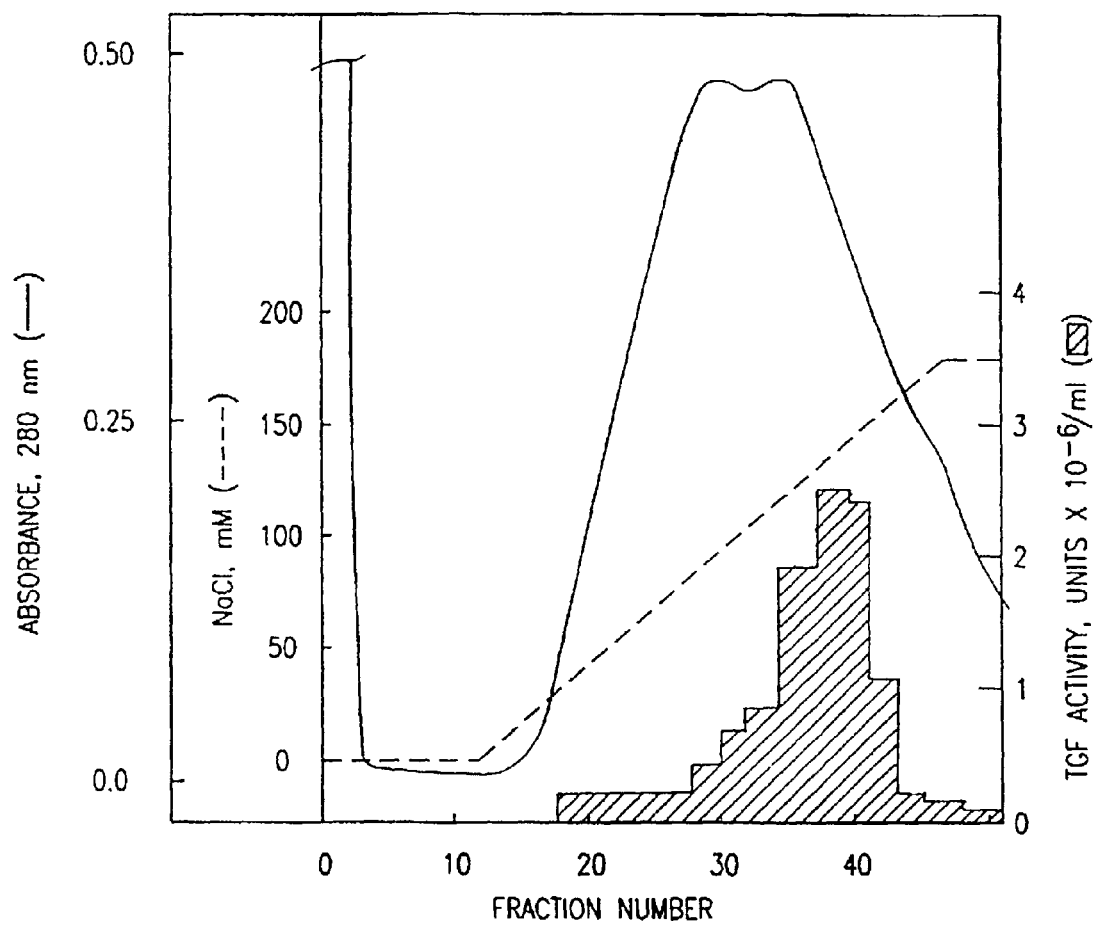
FIG. 1 is a plot of a supernatant solution obtained from cultured NC37 lymphoblastoid cells applied to a Nu-Gel P-SP column showing the protein fraction containing TGF activity being eluted with a salt gradient.
Figure 2:
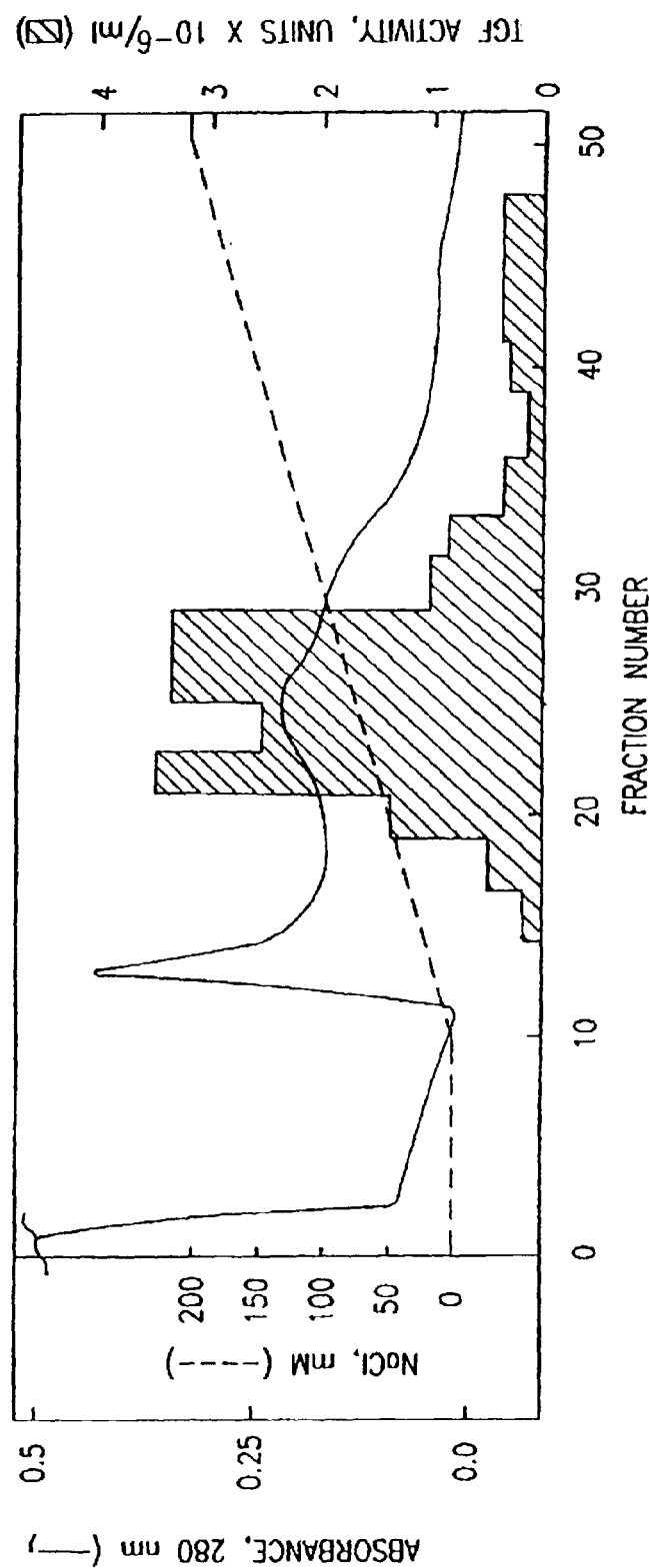
FIG. 2 is a plot of the material containing TGF activity obtained from the separation of FIG. 1 as it was being eluted with a salt gradient through a Blue-B-Agarose Column.
Figure 3:
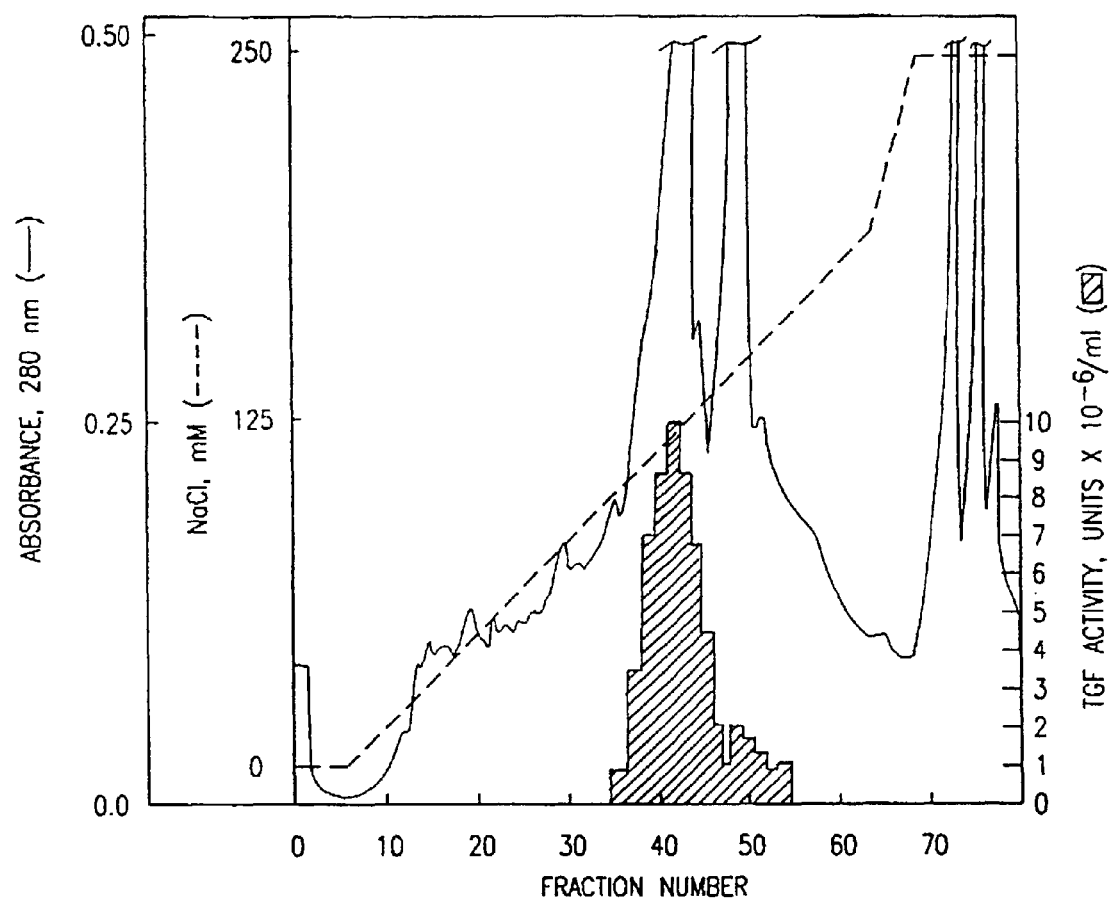
FIG. 3 shows the plot of the material containing TGF activity obtained from the separation of FIG. 2 as it was being eluted with a NaCl gradient through a Mono Q column.
Figure 4:
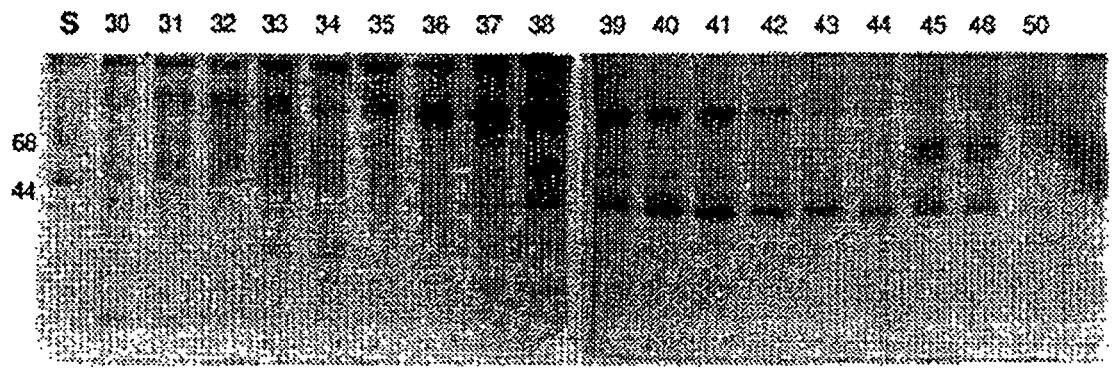
FIG. 4 shows the SDS-polyacrylamide gel electrophoresis (SDS-PAGE) analysis of the fractions obtained from the step illustrated in FIG. 3.

The supernatant solution was applied to a Nu-Gel P-SP column and protein was eluted with a salt gradient (FIG. 1). Peak T cell growth factor (TGF) activity was determined and the active fractions were pooled and dialyzed in order to reduce the salt concentration of the preparation by 50-fold. This material, after centrifugation to remove particulates, was applied to a Blue-B-Agarose column. Protein was eluted with a salt gradient (FIG. 2). Peak TGF activity was determined and the active fractions were pooled and dialyzed in order to reduce the salt concentration of the preparation by 100-fold. This material, after filtration, was applied to a Mono Q column. Protein was eluted with a salt gradient (FIG. 3). Aliquots of fractions were assayed for TGF activity and protein purity of individual fractions was assessed by SDS-PAGE under non-reducing conditions using a 12% slab gel. The gel was silver stained to visualize protein (FIG. 4). Fractions 36 and 37 were of greater than 95% purity and revealed a major band at 75,000 molecular weight. Fractions 38 through 41 containing TGF activity, revealed the 75 kDa protein by SDS-PAGE with major contaminants at 55,000 and 40,000 molecular weight.

Figure 5:
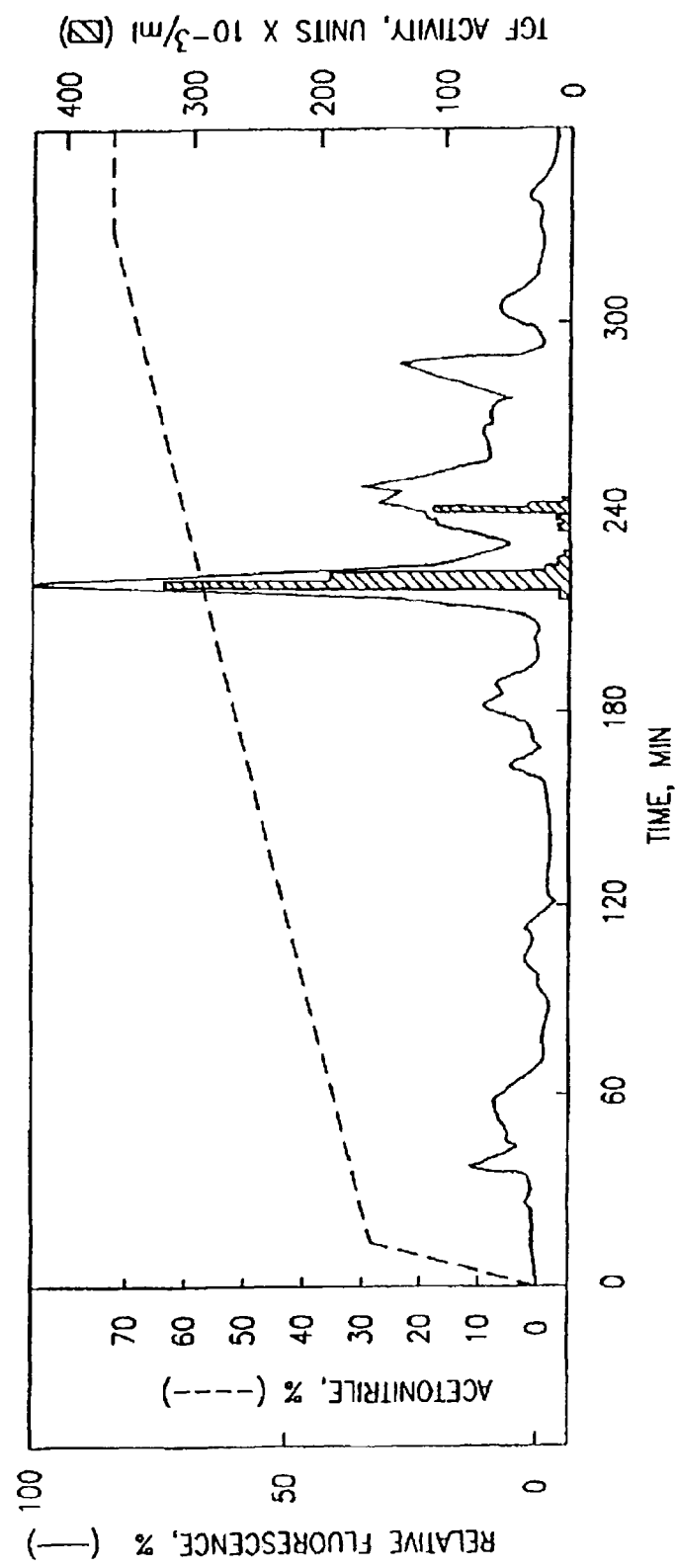
FIG. 5 shows the elution profile through a Vydac Diphenyl column of fraction 38 from the Mono Q Chromatography separation.
Figure 6:
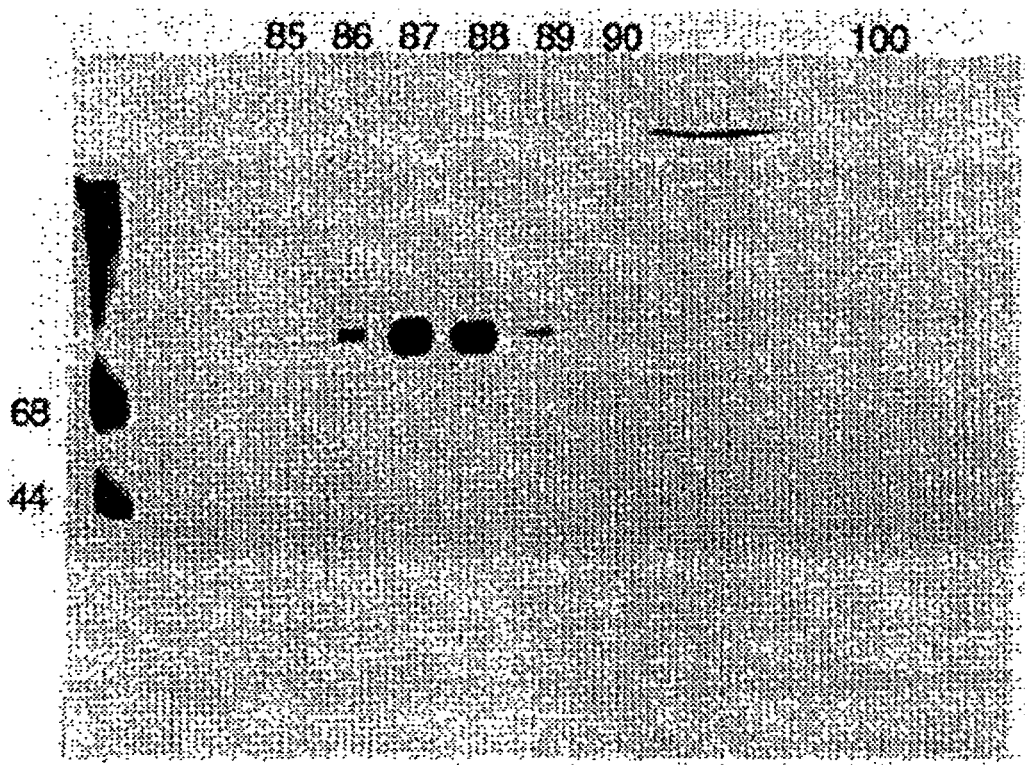
FIG. 6 shows SDS-PAGE analysis of protein purity of the protein fractions 86-90 recovered from the process depicted in FIG. 5.
Figure 7:
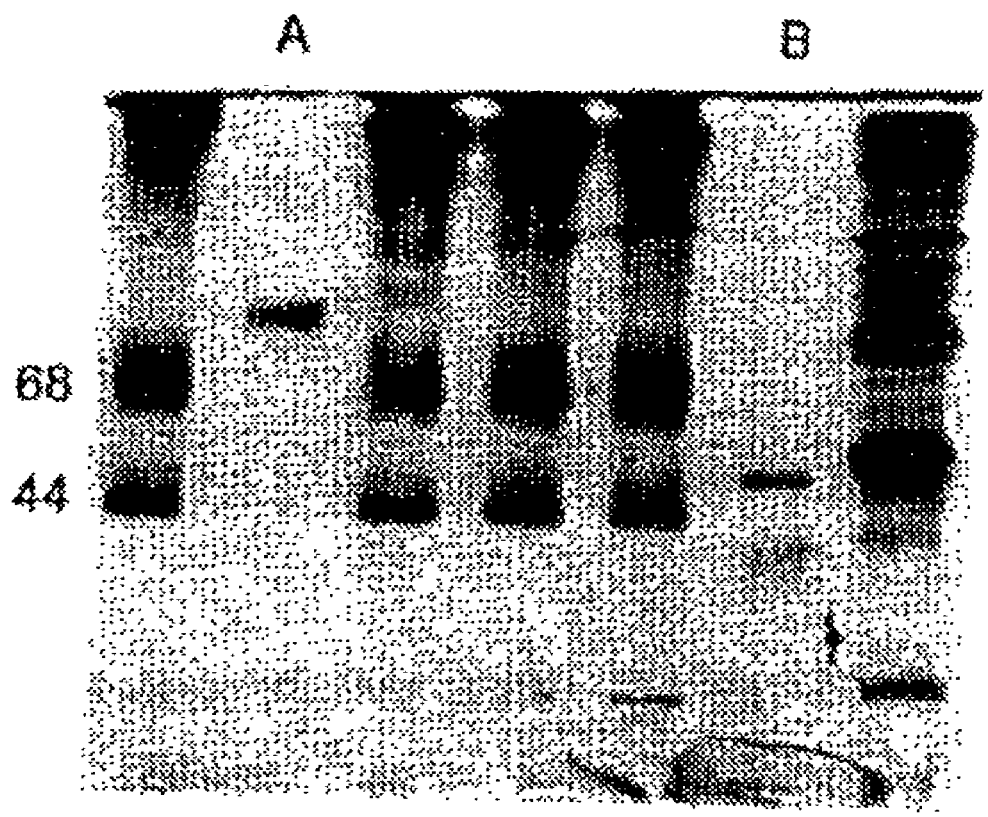
FIG. 7 shows the SDS PAGE analysis of fractions 87 and 88 under non-reducing (without β-mercaptoethanol) and reducing (in the presence of β-mercaptoethanol) conditions showing the 75,000 molecular weight CLMF separated into two subunits of 40 kDa and 35 kDa.

Therefore, to eliminate these contaminating proteins, fraction 38 of the previous Mono Q chromatography was diluted 1:1 vol/vol with 8 M urea and pumped onto a Vydac diphenyl column using an enrichment technique. The column was then washed with 5 ml of 0.1% trifluoroacetic acid. Elution of the proteins was accomplished with a gradient of 0-70% acetonitrile over 7 hrs in 0.1% trifluoroacetic acid (FIG. 5). Aliquots of fractions were assayed for TGF activity. Protein purity of the fractions containing TGF activity was assessed by SDS-PAGE under non-reducing conditions using a 10% slab gel. The gel was silver stained to visualize protein (FIG. 6). Fractions 86 through 90 were of greater than 95% purity and revealed protein of 75,000 molecular weight. Fractions 87 and 88 were pooled and aliquots were analyzed by SDS-PAGE under reducing (in the presence of β-mercaptoethanol) and non-reducing conditions (in the absence of β-mercaptoethanol). Under the reducing conditions, the 75,000 molecular weight CLMF was separated into two subunits of 40,000 and 35,000 daltons (FIG. 7). Thus we may conclude that CLMF is a 75 kDa heterodimer composed of disulfide-bonded 40 kDa and 35 kDa subunits.

The overall purification of CLMF that was achieved is shown in Table 1. The protein content of the Mono Q- and Vydac diphenyl-purified material was calculated on the basis of amino acid analysis. A specific activity of $8.5 \times 10^7$ units/mg and $5.2 \times 10^7$ units/mg for Mono Q- and Vydac diphenyl-purified material respectively, was obtained. The fact that the diphenyl-purified protein has a slightly lower specific activity than the Mono Q-purified material may be due to inactivation or denaturation of some of the molecules of CLMF in the HPLC elution solvents (i.e., acetonitrile in 0.1% trifluoroacetic acid)

Chemical Characterization

The ability to prepare homogeneous CLMF allowed for the determination of the amino acid composition and partial sequence analysis of the naturally occurring CLMF protein. Between 10 and 20 picomoles of Mono-Q-purified CLMF was subjected to hydrolysis, and its amino acid composition was determined (Table 2). Proline, cysteine and tryptophan were not determined (ND). Quantitation of histidine was not possible due to a large artifact peak, associated with Tris, coeluting with His (*).

Between 5 and 30 picomoles of diphenyl-purified CLMF was subjected to hydrolysis with and without pre-treatment with performic acid. Complete amino acid composition was thus obtained (Table 3) with the exception of tryptophan.

TABLE 1

| Step | Volume (ml) | Pooled Activity (U/ml) | Total Units (U) | Pooled Protein (mg/ml) | Total Protein (mg) | Specific Activity (U/mg) |
|---|---|---|---|---|---|---|
| Pooled Cell Supernatants | 60,000 | $2.58 \times 10^3$ | $1.6 \times 10^8$ | ND | ND | ND |
| Ultrafiltered Concentrate | 1,940 | $1.57 \times 10^5$ | $3.0 \times 10^8$ | 1.83 | 3550 | $8.5 \times 10^4$ |
| NuGel P-SP | 90 | $2.00 \times 10^6$ | $1.8 \times 10^8$ | 0.70 | 63 | $2.8 \times 10^6$ |
| Blue-B-Agarose | 45 | $3.11 \times 10^6$ | $1.4 \times 10^8$ | 0.24 | 11 | $1.3 \times 10^7$ |
| Mono Q Fraction 37 | 1 | $6.40 \times 10^6$ | $6.4 \times 10^6$ | 0.075 | 0.075 | $8.5 \times 10^7$ |
| Mono Q Fraction 38 –> 42 | 5 | $6.90 \times 10^6$ | $3.45 \times 10^7$ | 0.081 | 0.405 | $8.5 \times 10^7$ |
| Diphenyl Fraction 87 + 88 | 1.1 | $5.74 \times 10^5$ | $5.22 \times 10^5$ | 0.008 | 0.010 | $5.2 \times 10^7$ |

TABLE 2

| Amino Acid | mol % |
|---|---|
| Aspartic acid or asparagine | 11.8 |
| Threonine | 7.8 |
| Serine | 8.4 |
| Glutamic acid or glutamine | 14.9 |
| Proline | ND |
| Glycine | 6.2 |
| Alanine | 7.6 |
| Cysteine | ND |
| Valine | 6.9 |
| Methionine | 2.0 |
| Isoleucine | 4.6 |
| Leucine | 9.0 |
| Tyrosine | 3.7 |
| Phenylalanine | 4.0 |
| Histidine | * |
| Lysine | 9.3 |
| Arginine | 5.4 |
| Tryptophan | ND |

TABLE 3

| Amino acid | mol % |
|---|---|
| Aspartic acid or asparagine | 10.8 |
| Threonine | 7.2 |
| Serine | 8.9 |
| Glutamic acid or glutamine | 13.1 |
| Proline | 3.8 |
| Glycine | 4.7 |
| Alanine | 5.9 |
| Cysteine | 2.9 |
| Valine | 6.2 |
| Methionine | 1.9 |
| Isoleucine | 4.2 |
| Leucine | 9.4 |
| Tyrosine | 3.6 |
| Phenylalanine | 3.7 |
| Histidine | 1.8 |
| Lysine | 7.7 |
| Arginine | 4.4 |
| Tryptophan | ND |

Amino-terminal sequence determination was attempted by automated Edman degradation on 100 pmol of the, Mono Q purified CLMF Data from the first 22 cycles indicated two sequences present, as would be expected from the heterodimeric structure of CLMF. These results may be summarized as follows.

| Cycle | 1 | 2 | 3 | 4 | 5 | 6 | 7 | 8 |
|---|---|---|---|---|---|---|---|---|
| Amino Acid | I/? | W/? | E/L | L/P | K/V | K/A | D/T | V/P |
| Cycle | 9 | 10 | 11 | 12 | 13 | 14 | 15 | 16 |
| Amino Acid | Y/D | V/P | V/G | E/M | L/F | D/P | W/? | Y/L |
| Cycle | 17 | 18 | 19 | 20 | 21 | 22 | | |
| Amino Acid | P/H | D/H | A/S | P/Q | G/? | E/? | | |

EXAMPLE 2

Determination of the Amino-terminal Sequence of the 40,000 Dalton Subunit of CLMF Stored supernatant solutions from NC-37 cells totaling 39.1 liters were pooled and concentrated to approximately 2.4 liters using the Pedicon Cassette System and stored at −20° C. To clarify this concentrate after thawing preparation was centrifuged and the precipitate discarded.

Figure 8:
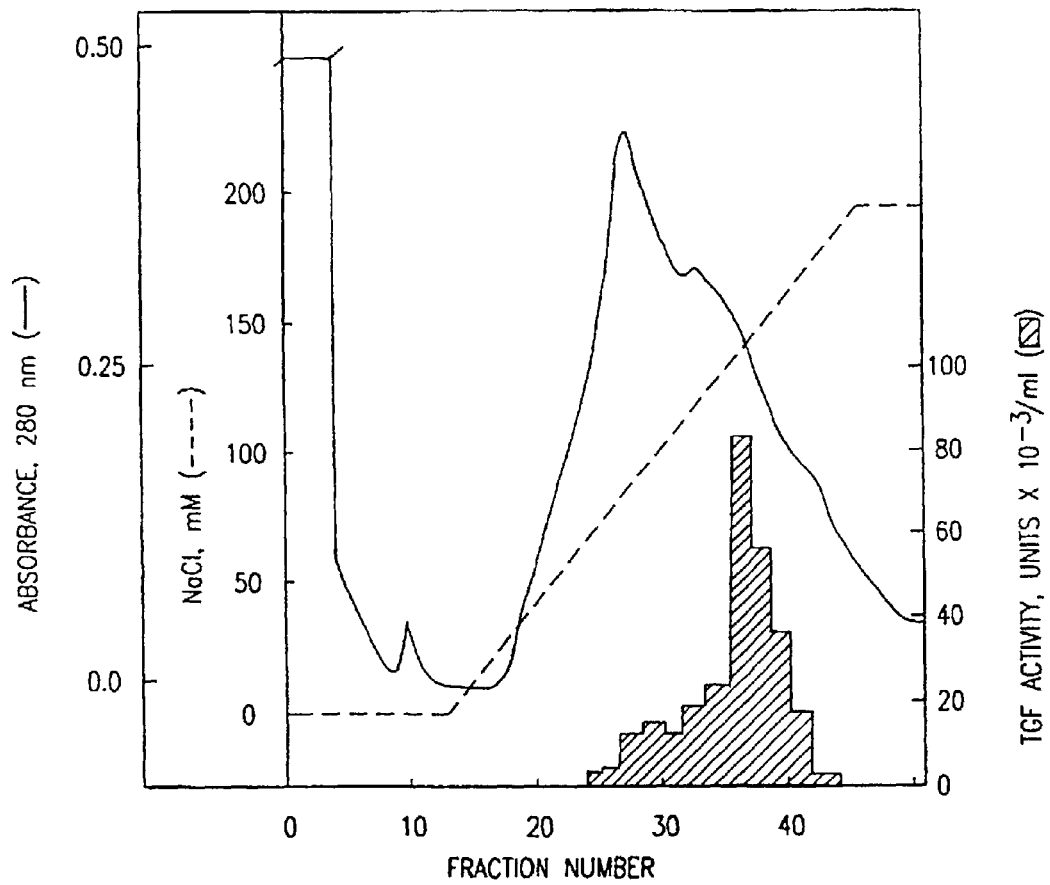
FIG. 8 shows the elution pattern of the proteins from the supernatant solution from NC-37 cells applied to a Nu-Gel P-SP column eluted with a salt gradient in Example 2.
Figure 9:
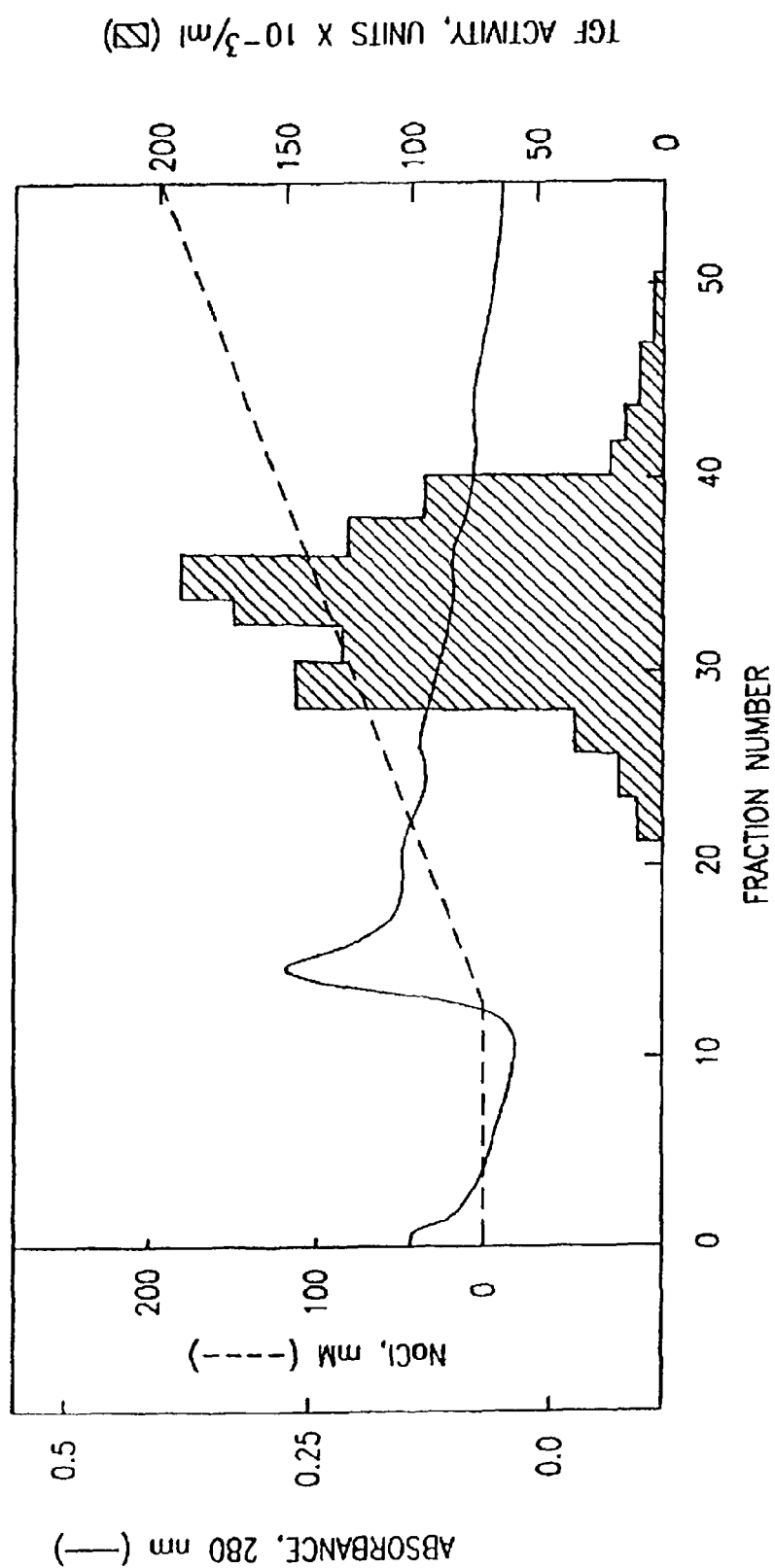
FIG. 9 is a Blue-B-Agarose column salt gradient elution profile of the active fractions obtained from the Nu-Gel P-SP column elution of FIG. 8.
Figure 10:
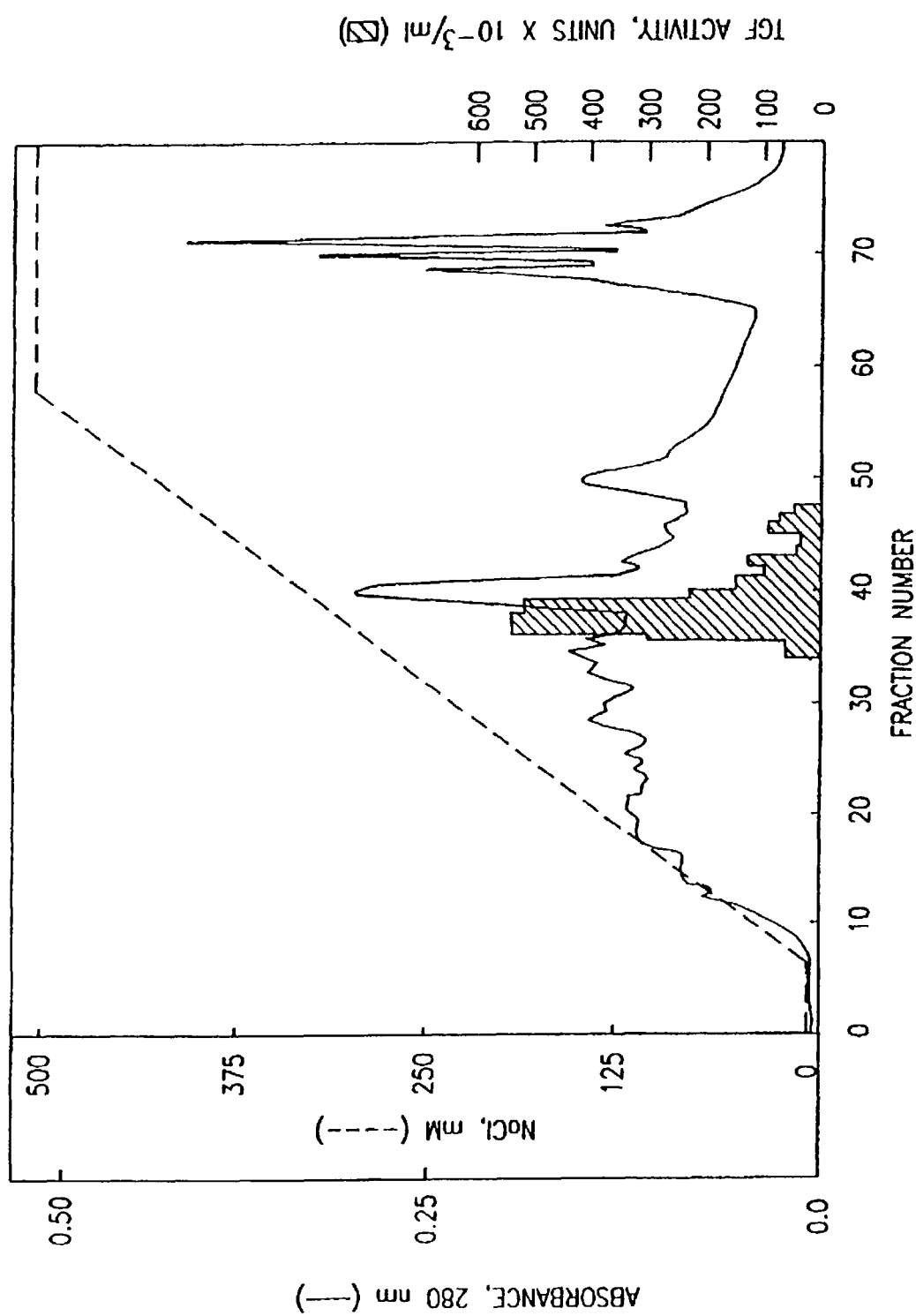
FIG. 10 is a Mono-Q column salt gradient elution profile of the active fractions obtained from the elution shown in FIG. 9.

The supernatant solution was applied to a Nu-Gel P-SP column and protein was eluted with a salt gradient (FIG. 8). Peak TGF activity was determined and the active fractions were-pooled and dialyzed in order to reduce the salt concentration of the preparation by 50-fold. This material, after centrifugation to remove particulates, was applied to a Blue-B-Agarose column. Protein was eluted with a salt gradient (FIG. 9). Peak TGF activity was determined and the active fractions were pooled and dialyzed in order to reduce the salt concentration of the preparation by 100-fold. This material, after filtration, was applied to a Mono Q column. Protein was eluted with a salt gradient (FIG. 10). Aliquots of fractions were assayed for TGF activity.

Figure 11:
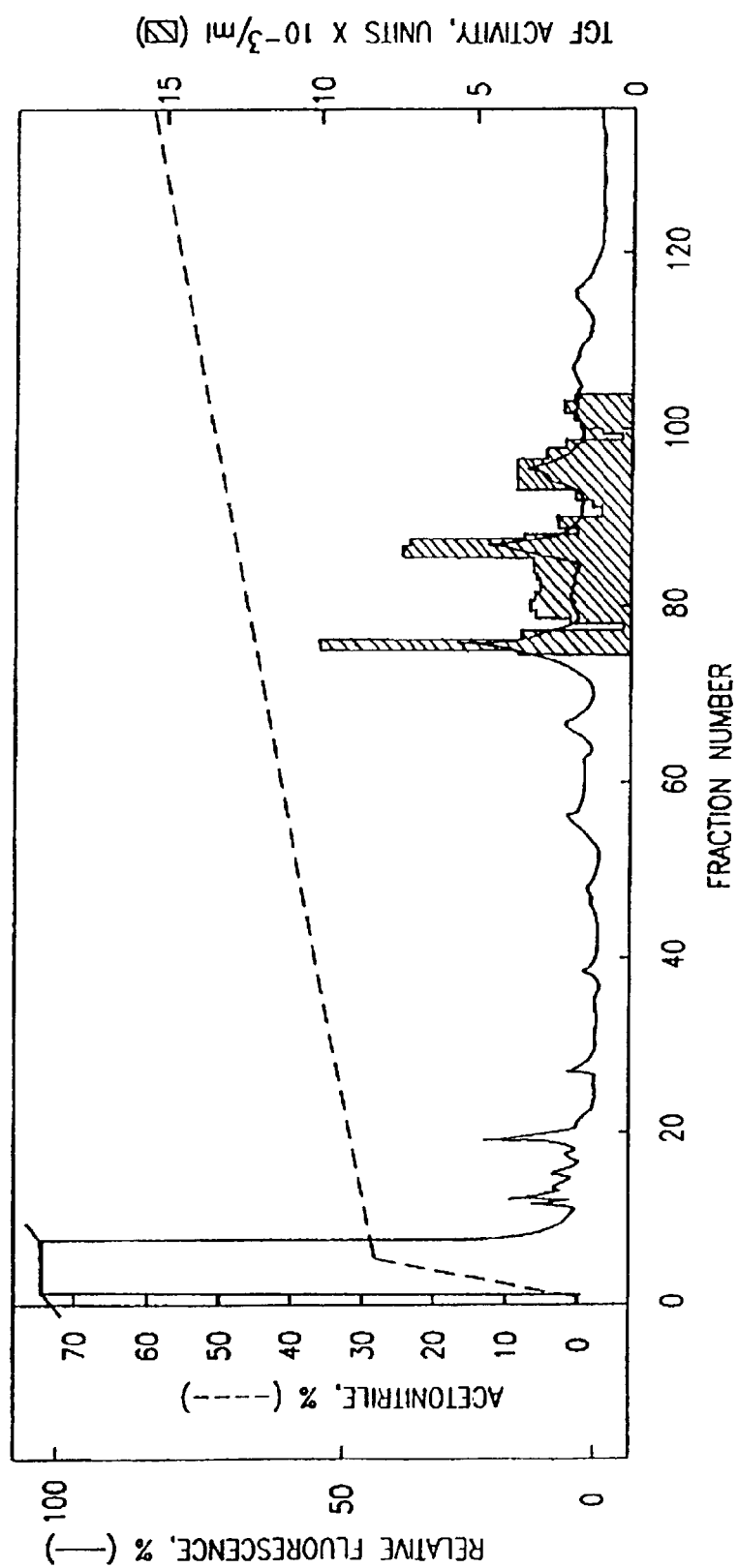
FIG. 11 is the elution pattern through a Vydac Diphenyl column of active fractions 39 and 40 obtained from the Mono Q Chromatography shown in FIG. 10.
Figure 12:
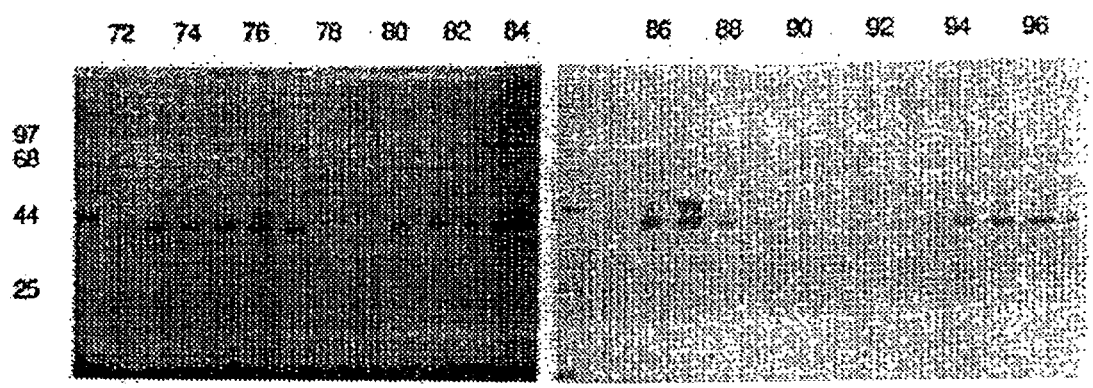
FIG. 12 is the SDS PAGE analysis under reducing conditions of the active fractions obtained from the elution of FIG. 11.

Fractions 39 and 40 of the previous Mono Q chromatography were pooled and diluted 1:1 vol/vol with 8 M urea and pumped onto a Vydac diphenyl column using an enrichment technique. The column was then washed with 5 ml of 0.1% trifluoroacetic acid. Elution of the proteins was accomplished with a gradient of 0-70% acetonitrile over 7 hrs in 0.1% trifluoroacetic acid (FIG. 11). Aliquots of fractions were assayed for TGF activity. Protein purity of the fractions containing TGF activity was assessed by SDS-PAGE under reducing (in the presence of β-mercaptoethanol) conditions (FIG. 12), Fractions 94 through 97 contained the 40,000 dalton subunit >90% pure.

Chemical Characterization

The ability to prepare a highly enriched preparation of the 40,000 dalton subunit of CLMF allowed for its partial sequence analysis.

Amino terminal sequence determination was attempted by automated Edman degradation on 20 pmol of the diphenyl purified 40,000 dalton subunit. The results may be summarized as follows:

| Cycle | 1 | 2 | 3 | 4 | 5 | 6 | 7 | 8 | 9 | 10 | 11 | 12 |
|---|---|---|---|---|---|---|---|---|---|---|---|---|
| Amino Acid | I | W | E | L | K | K | D | V | Y | V | V | E |
| Cycle | 13 | 14 | 15 | 16 | 17 | 18 | 19 | 20 | 21 | 22 | 23 | |
| Amino Acid | L | D | W | Y | P | D | A | P | G | E | M | |

With regard to the sequence analysis of 75,000 dalton CLMF (example 1) and the sequence analysis of the 40,000 dalton subunit of CLMF (example 2), one can deduce the amino terminal sequence of the 35,000 dalton subunit of CLMF. The amino terminal sequences of the 35,000 dalton subunit and the 40,000 dalton subunit can be summarized as follows:

35,000 dalton subunit:

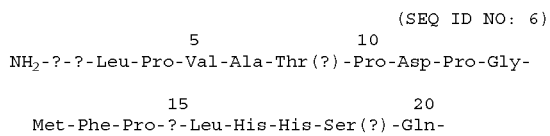

```
                                          (SEQ ID NO: 6)
                         5              10
     NH2-?-?-Leu-Pro-Val-Ala-Thr(?)-Pro-Asp-Pro-Gly-
                         15              20
           Met-Phe-Pro-?-Leu-His-His-Ser(?)-Gln-
```

40,000 dalton subunit:

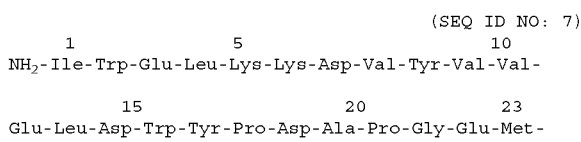

```
                                               (SEQ ID NO: 7)
        1               5                 10
     NH2-Ile-Trp-Glu-Leu-Lys-Lys-Asp-Val-Tyr-Val-Val-
               15             20             23
     Glu-Leu-Asp-Trp-Tyr-Pro-Asp-Ala-Pro-Gly-Glu-Met-
``` where ? represents an undetermined or "best-guessed" residue.

EXAMPLE 3

Determination of Internal Amino Acid Sequence Segments of the 40,000 Dalton Subunit of CLMF CLMF was purified as previously described in Example 1. The 40,000 dalton subunit was separated and purified from the 35,000 dalton subunit by the method described by Matsudaira [Journal of Biological Chemistry 262, 10035-10038 (1987)]. Fifty micrograms of CLMF (in 500 IL of 20 mM Tris, pH 7.5; 0.15 M NaCl) was diluted with 200 μl 2× concentrate Laemmli sample buffer [Nature 227, 680-685 (1970)]. The sample was concentrated to 400 μl and disulfide bonds broken by the addition of 18 μl β-mercaptoethanol followed by exposure to 105° C. for 6 minutes.

The sample was loaded onto a minigel (1.0 mm thick) containing 12% polyacrylamide and electrophoresed according to Laemmli. After-electrophoresis, the gels were soaked in transfer buffer (10 mM 3-[cyclohexylamino]-1-propanesulfonic acid, 10% methanol, pH 11.0) for 5 min to reduce the amount of Tris and glycine. During this time, a polyvinylidene difluoride (PVDF) membrane (Immobilon; Millipore; Bedford, Mass.) was rinsed with 100% methanol and stored in transfer buffer. The gel, backed with two sheets of PVDF membrane and several sheets of blotting paper, was assembled into a blotting apparatus and electroeluted for 30 min at 0.5 Amps in transfer buffer. The PVDF membrane was washed in deionized $H_2O$ for 5 min. The edge of the blot was excised from the PVDF membrane and stained with 0.L1% Coomassie Blue R-250 in 50% methanol for 5 min, and then destained in 50% methanol, 10% acetic acid for 5-10 min at room temperature. The 40,000 dalton stained band was then matched to the corresponding region of the unstained blot and the 40,000 subunit was cut from the unstained PVDF.

The Coomassie Blue-stained 40,000 dalton subunit was N-terminal sequenced to confirm that the N-terminus matched that previously obtained (see Example 2). By this method, the 40,000 dalton protein was identified as the 40,000 subunit of CLMF.

Five percent of the PVDF bound 40,000 dalton subunit was analyzed for its amino acid composition (Table 4). The remaining 95% of the blotted 40,000 dalton subunit was fragmented with trypsin according to the procedure of Bauw, Goal. [Proc. Natl. Acad. Sci. USA 86, 7701-7705 (1989)]. The membrane carrying the protein was cut into pieces of approximately 3 by 3 mm, and collected in an Eppendorf tube. They were then immersed in 300 µl of a 2% polyvinylpyrrolidone (40,000 dalton) solution in methanol. After 30 min., the quenching mixture was diluted with an equal volume of distilled water and further incubated for 5-10 min. The supernatant solution was then discarded and the membrane pieces were washed four times with 300 µl water and once with 300 µl 100 mM Tris HCl (pH 8.5). Two hundred microliters of this buffer containing 2 µg of trypsin was added. The sample was shaken and incubated for 4 hr at 37° C. The supernatant solution was then transferred into a second Eppendorf tube and the membrane pieces were further washed once with 100 µl of 88% (vol/vol) formic acid and three times with 100 µl of deionized water. All washing solutions were added to the digestion mixture in the second Eppendorf tube. The resultant peptides contained in the pooled digest were separated by narrow bore HPLC (HP1090A, Hewlett Packard) on a YMC C-18 column (2.6× 50 mm; Morris Plains, N.J.).

Figure 13:
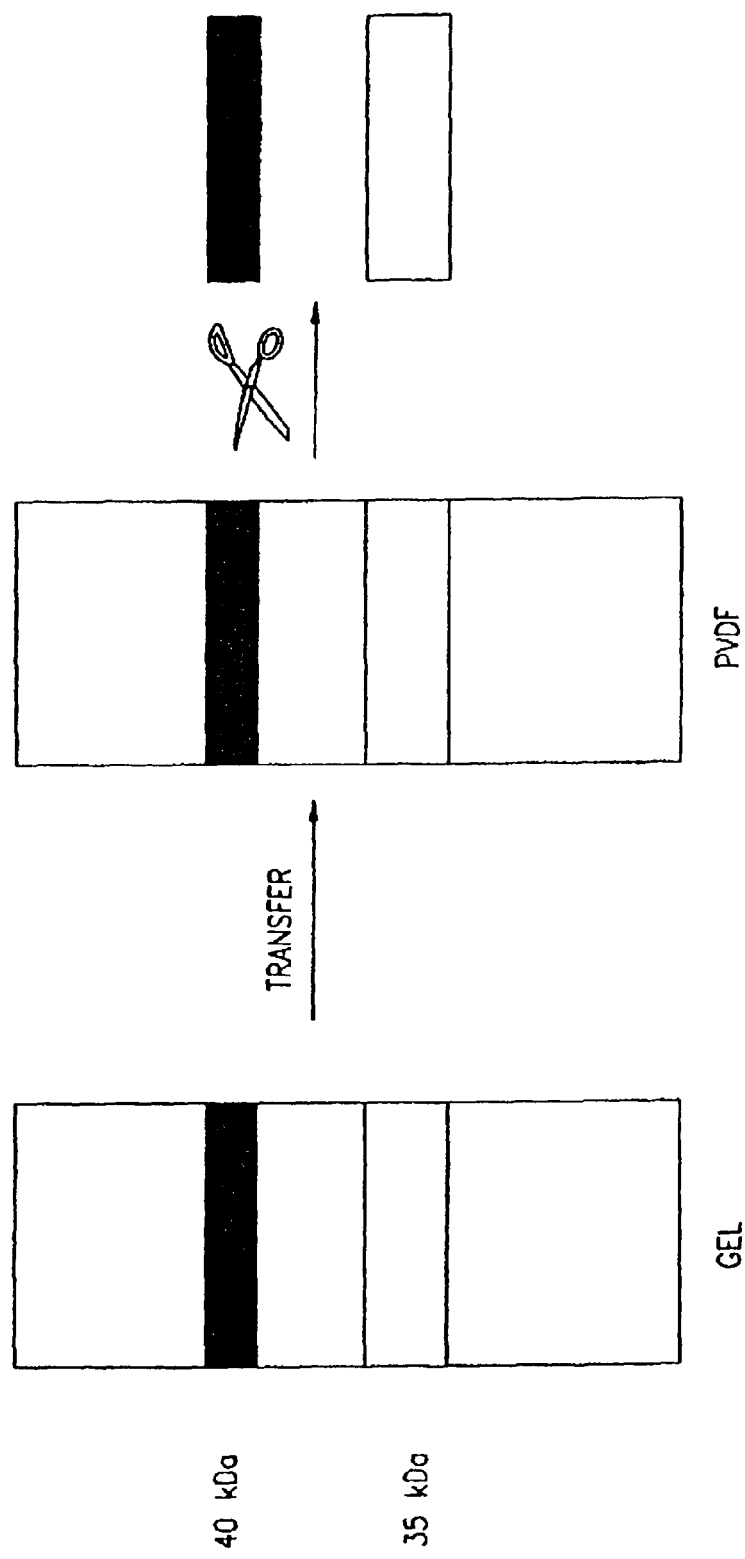
FIG. 13 is a schematic diagram—showing the separation of the 40kDa subunit from the 35kDa subunit of the CLMF cytokine of the present invention.
Figure 14:
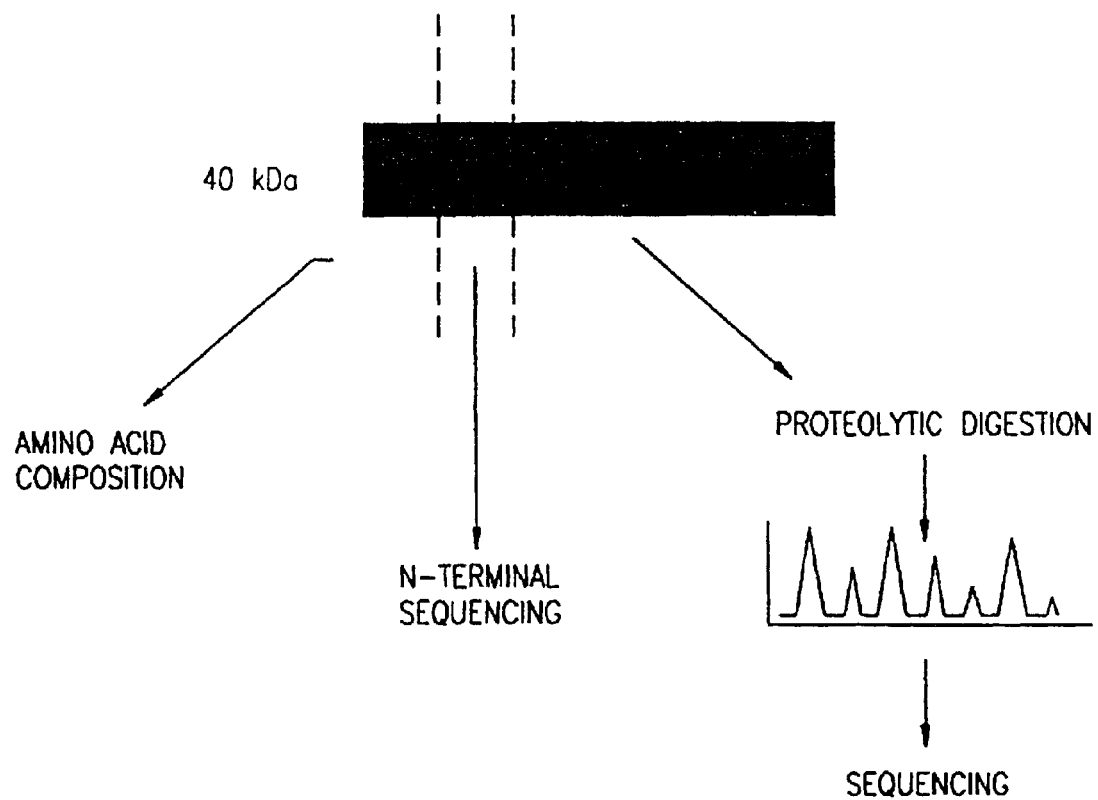
FIG. 14 is a schematic diagram showing the determination of the amino acid composition, N-terminal sequencing, proteolytic digestion and complete sequencing of the 40kDa subunit of the CLMF cytokine of the present invention.

The above described procedure is shown, in cartoon form, in FIGS. 13 & 14.

Figure 15:
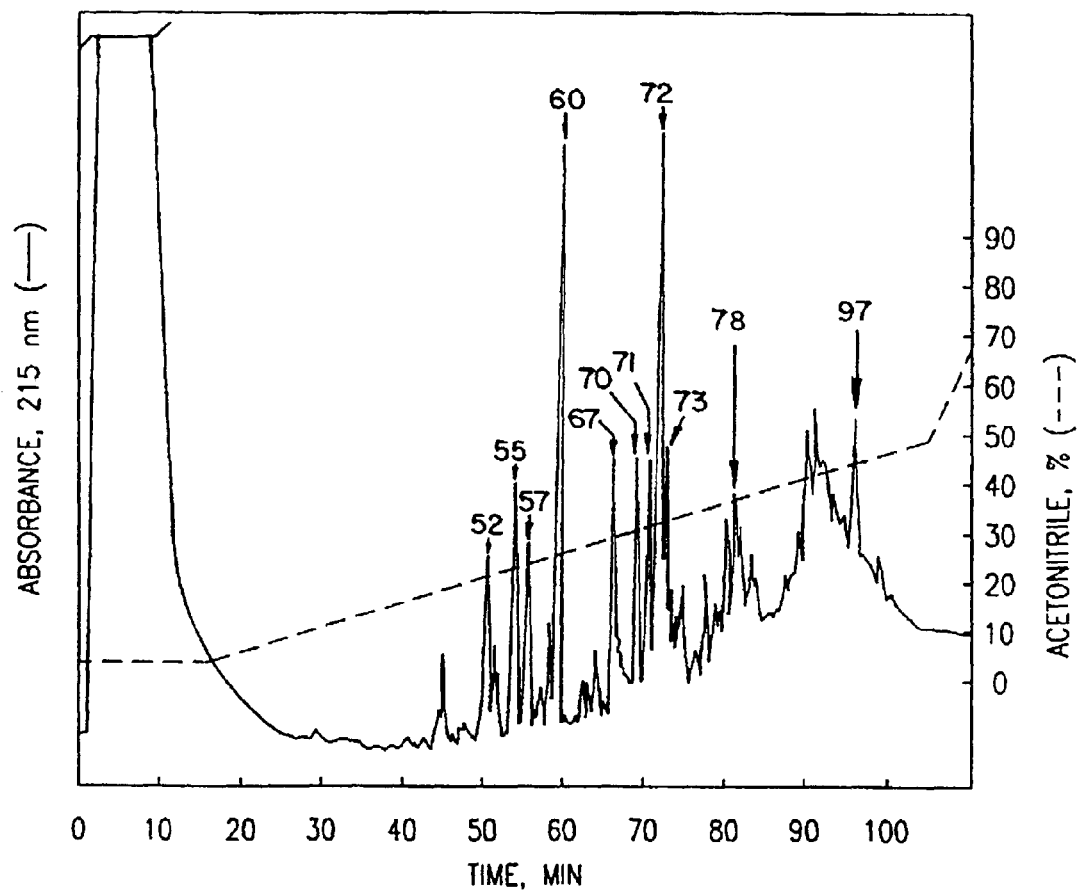
FIG. 15 is a tryptic peptide map of the digested 40kDa subunit of the CLMF cytokine of the present invention.

The tryptic peptide map of the digested 40,000 dalton subunit is shown in FIG. 15. Peptides were eluted with a linear gradient of acetonitrile. The peaks which were sequenced are numbered according to their fraction number. The amino acid sequence of these peptides is shown in Table 5.

Many tryptic peptides were recovered from all regions of the intact 40,000 dalton subunit (Table 5). The N-terminal hexapeptide (fraction no. 60) was recovered in high yield. The carboxy-terminal peptide (fraction no. 72) was recovered and is the full length of the predicted C-terminal peptide although the last two amino acids were not positively confirmed by sequencing. This is probably due to the fact that Cys and Ser residues are not detected well, especially when they occur at the end of a peptide. Four potential. Asn-linked carbohydrate sites are predicted from the cDNA sequence. Two peptides containing two of these sites were sequenced. When peptide 196-208 (fraction no. 70) was sequenced, no peak was detected at residue 200 indicating that this Asn (predicted by the cDNA) is indeed glycosylated. Peptide 103-108 (fraction no. 52) yielded Asn at residue 103. Therefore, this site is not glycosylated.

An unknown peak seen in the PTH (sequence) analysis of fraction no. 55 was detected at the position corresponding to residue no. 148. The site is predicted to be a Cys residue which is normally not detected by sequence analysis unless it is modified.

Figure 16:
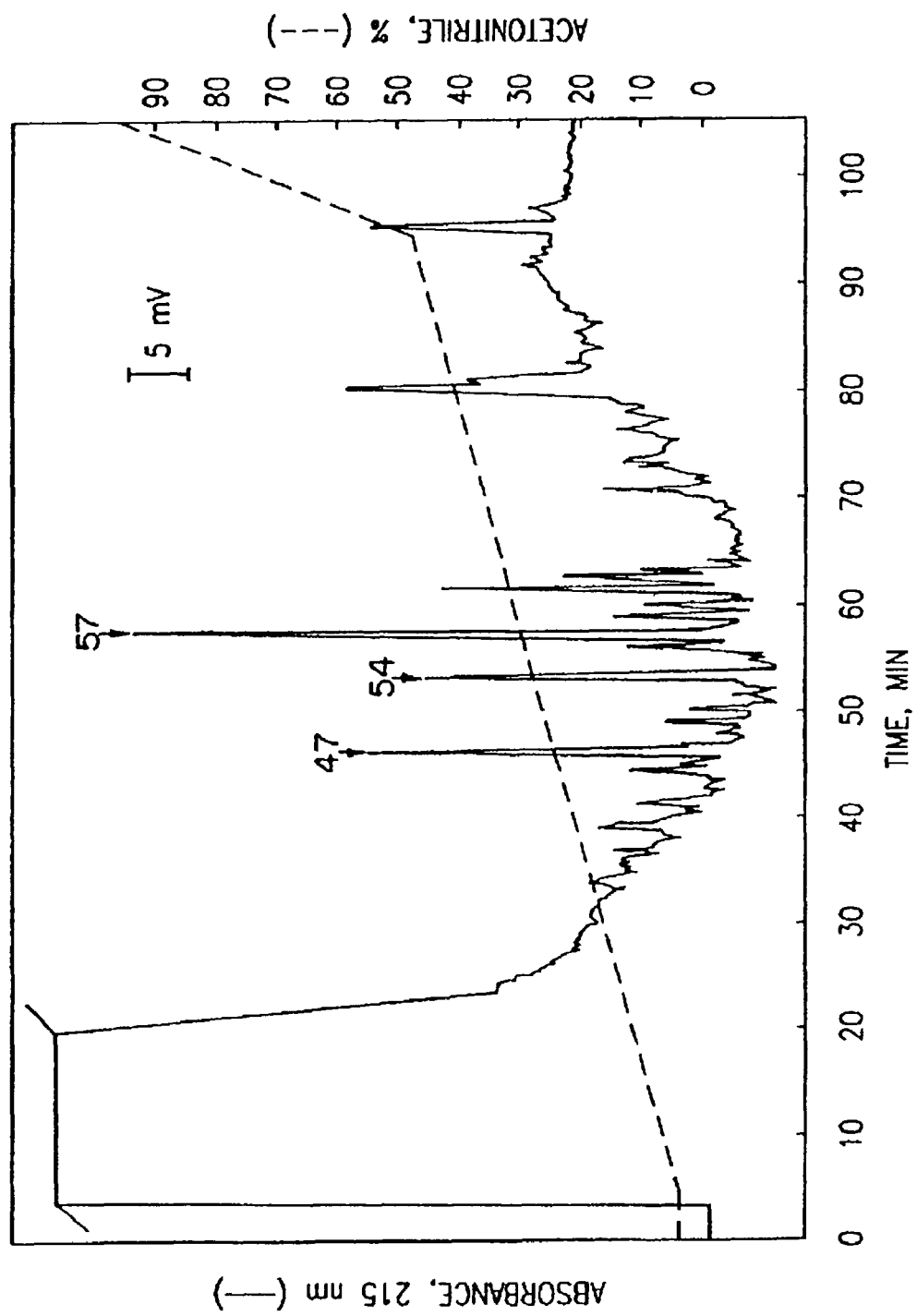
FIG. 16 is a proteolytic peptide map of the digested 40kDa subunit of the CLMF in which the proteolytic enzyme which was used was Staphylococcus aureus V8 protease

The above PVDF transfer procedure was repeated on a second 50 mg aliquot of CLMF (see FIGS. 13 & 14 for procedure outline). However, the blotted 40,000 dalton subunit was fragmented with the proteolytic enzyme, *Staphylococcus aureus* V8 protease (Endoproteinase Glu-C, Boerhinger Mannheim, Indianapolis, IN). Membrane pieces were digested for 6 hours at 37° C. with 20 mg of V8. The peptides were extracted with 88% (vol/vol) formic acid and separated on a Phase Separations column (2×150 mm, C8 S3, Queensferry, England, UK) (FIG. 16). Peptides were eluted with a linear gradient of acetonitrile. The peaks which were sequenced are numbered according to their fraction number. The amino acid sequence of these peptides is shown in Table 6.

Three major peaks of peptide (fraction nos. 47, 54 and 57) containing four peptides were sequenced. All four peptides were from the amino-terminal region of the 40 kDa subunit indicating that the N-terns of the protein is most susceptible to V8-digestion.

Figure 17:
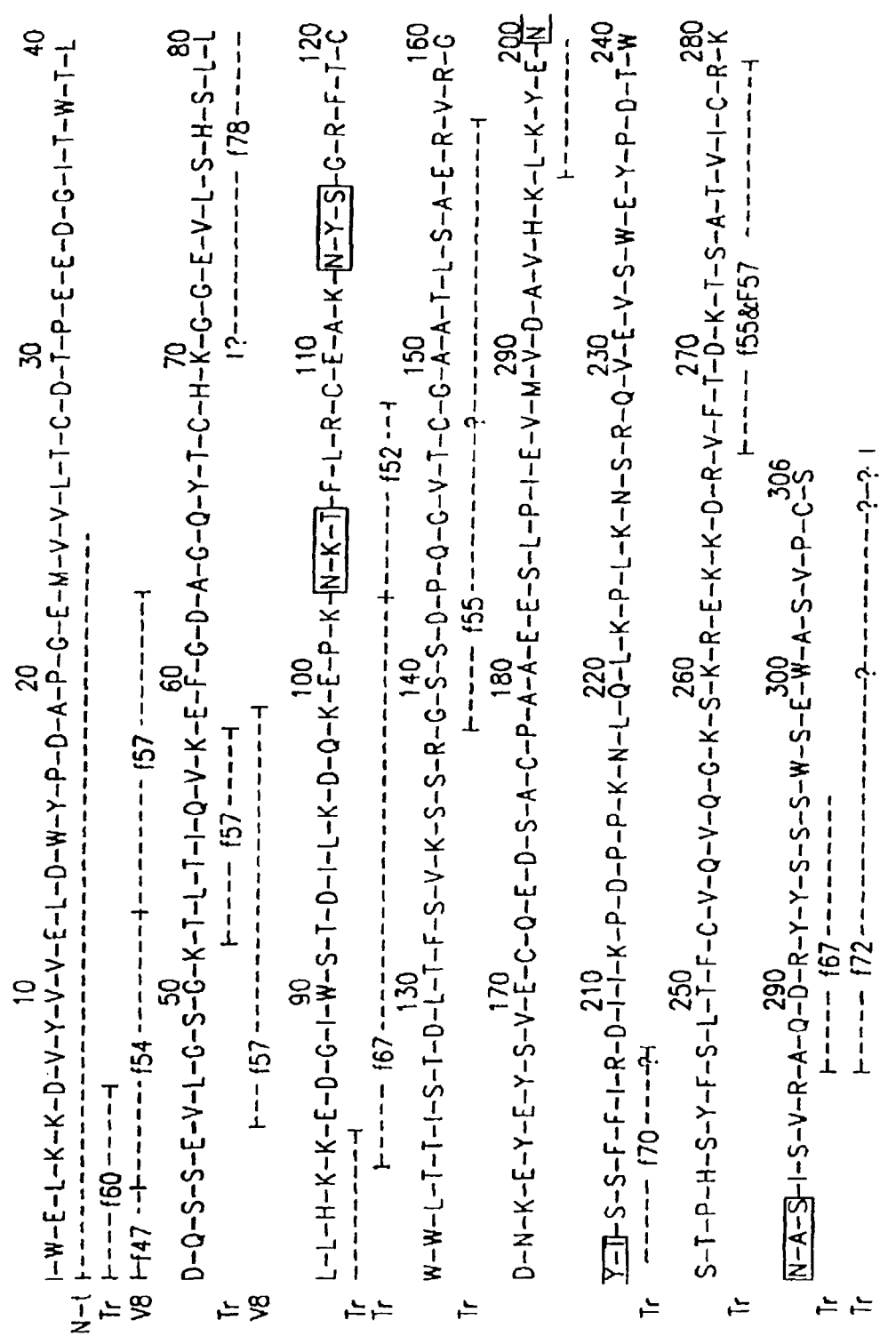

FIG. 17 summarizes the protein structural determination of the 40,000 dalton subunit of CLMF.

TABLE 4

| Amino Acid | Residue No. | |
|---|---|---|
| Aspartic acid or asparagine | 27.9 | (28) |
| Threonine | 20.7 | (23) |
| Serine | 24.6 | (34) |
| Glutamic acid or glutamine | 44.6 | (35) |
| Proline | ND | (14) |
| Glycine | 16.3 | (15) |
| Alanine | 16.2 | (14) |
| Cysteine | ND | (10) |
| Valine | 20.9 | (23) |
| Methionine | 2.5 | (2) |
| Isoleucine | 10.3 | (12) |
| Leucine | 22.9 | (22) |
| Tyrosine | 12.9 | (12) |
| Phenylalanine | 9.9 | (9) |
| Histidine | 5.2 | (5) |
| Lysine | 24.5 | (26) |
| Arginine | 12.5 | (12) |
| Tryptophan | ND | (10) |

Note:
The results represent the mean of two analyses. Proline, cysteine, and tryptophan were not determined (ND). Values in parentheses represent the theoretical amino acid composition of the 40,000 dalton subunit based upon the primary structure of the protein deduced from sequence analysis of cloned 40,000 dalton subunit.

TABLE 5

Tryptic 40 kDa CLMF peptides off PVDF

| fraction no. | residue no. | N-terminal sequence |
|---|---|---|
| 52 | 103-108 | N-K-T-F-L-R |
| 55 | 139-157 | G-S-S-D-P-Q-G-V-T-*-G-A-A-T-L-S-A-E-R |
| 55 & 57 | 267-279(?) | V-F-T-D-K-T-S-A-T-V-I-?-R |
| 57 | 52-58 | T-L-T-I-Q-V-K |
| 57 | 218-228 | N-L-Q-L-K-P-L-K-N-S-R |
| 60 | 1-6 | I-W-E-L-K-K |

TABLE 5-continued

Tryptic 40 kDa CLMF peptides off PVDF

| fraction no. | residue no. | N-terminal sequence |
|---|---|---|
| 67 | 288-? | A-Q-D-R-Y-Y-S-S |
| 67 | 85-102(?) | K-E-D-G-I-W-S-T-D-I-L-K-D-Q-K-E-P- |
| 70 | 196-208 | L-K-Y-E-?-Y-T-S-S-F-F-I-(R?) |
| 71 | 85-96(?) | K-E-D-G-I-?-S-T-D-I-L-K |
| 72 | 288-306(?) | A-Q-D-R-Y-Y-S-S-S-W-E-?-A-S-V-P-?-? |
| 78 | 71-85 | (G?)-G-E-V-L-S-H-S-L-L-L-(L?)-H-K-K |

TABLE 6

V8 (Glu-C) 40 kDa peptides off PVDF

| fraction no. | residue no. | N-terminal sequence |
|---|---|---|
| 47 | 1-3 | I-W-E |
| 54 | 4-12 | L-K-K-D-V-Y-V-V-E |
| 57 | 13-22 | L-D-W-Y-P-D-A-P-G-E |
| 57 | 45-59 | V-L-G-S-G-K-T-L-T-I-Q-V-K-(E?) |

EXAMPLE 4

Figure 18:
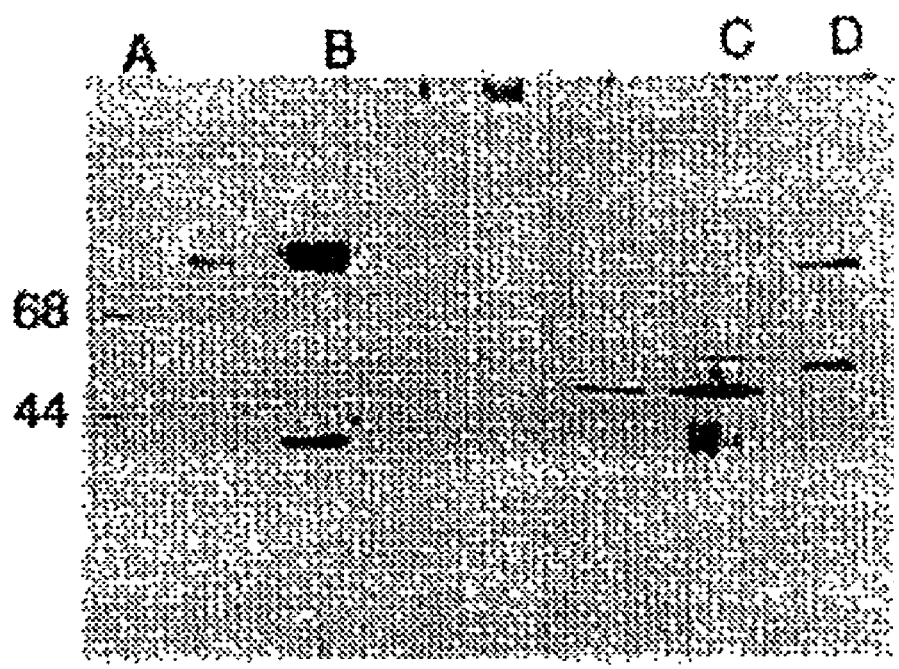
FIG. 18 is the SDS PAGE analysis of Fraction 39 from the Mono Q FPLC elution shown in FIG. 4.

Direct Determination of the Amino-terminal Sequence of the 35,000 Dalton Subunit of CLMF SDS-PAGE analysis of the Mono Q fraction 39 from Example 1 under reducing (in the presence of β-mercaptoethanol) and non-reducing (in the absence of β-mercaptoethanol) conditions (FIG. 18) demonstrated that the 40,000 dalton molecular weight "contaminant" is "free" 40,000 dalton CLMF subunit (i.e. unassociated with the 35,000 dalton subunit). The evidence which points to the deduction is that without reduction (lane 1, FIG. 18) mainly 75,000 dalton CLMF is present with some 40,000 dalton protein. After reduction (lane 2, FIG. 18), the 75,000 dalton CLMF is gone yielding the 35,000 dalton subunit and an enriched 40,000 dalton band.

Figure 19:
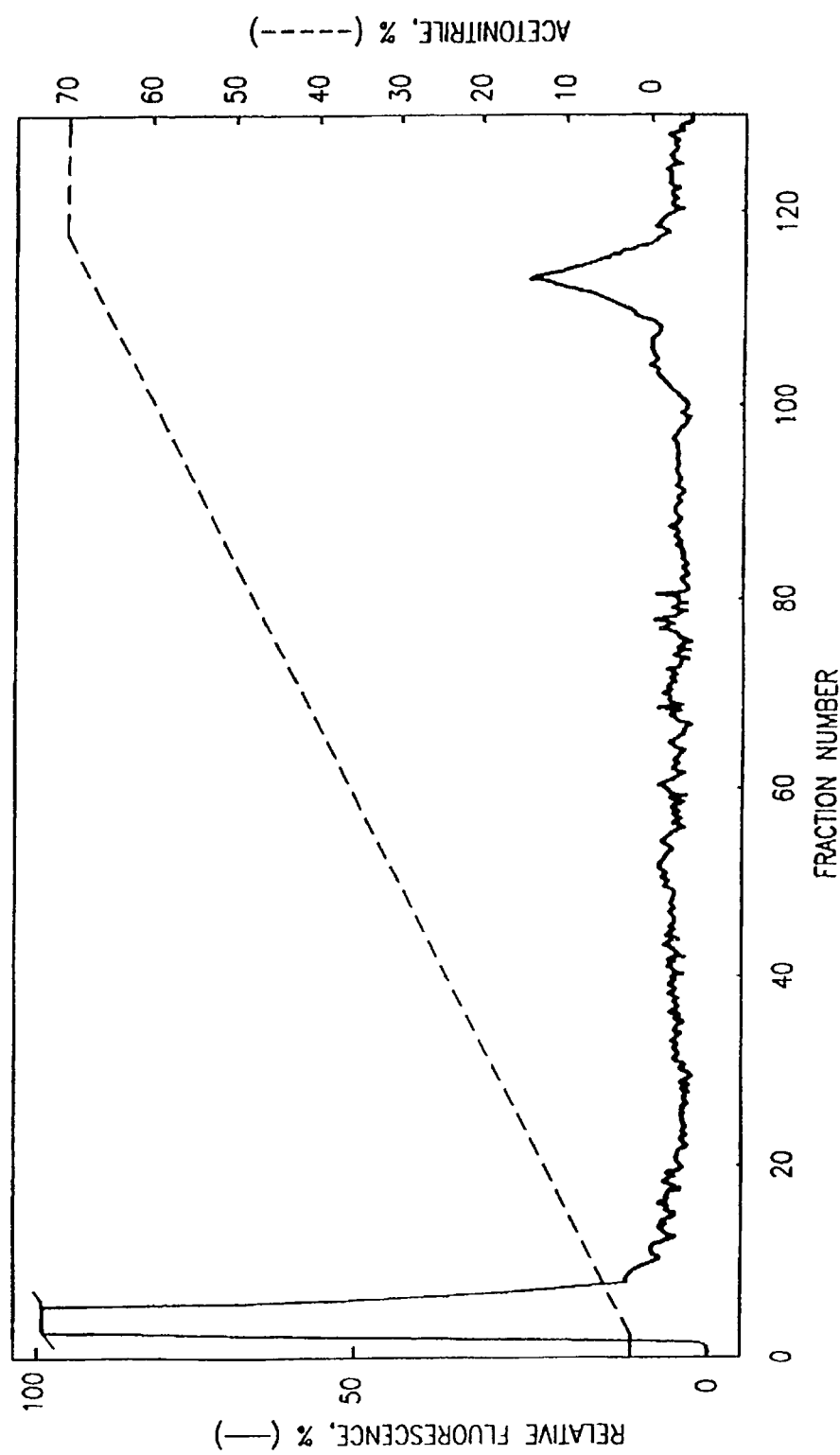
FIG. 19 is the elution pattern through a Vydac C-18 column of fraction 39 of the Mono Q chromatography which was reduced in 5% β-mercaptoethanol.
Figure 20:
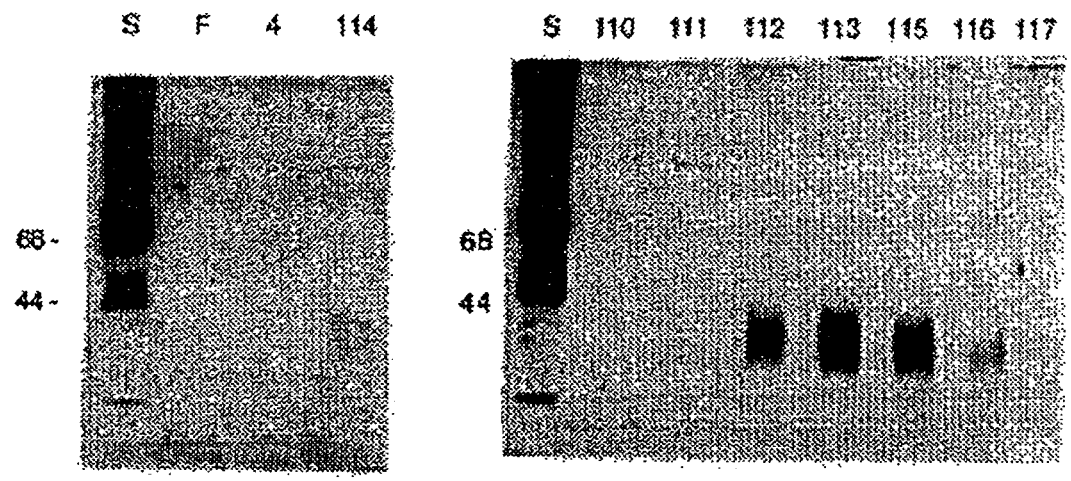
FIG. 20 is the SDS-PAGE gel analysis under non-reducing conditions of the fractions which were fluorescamine positive from the Vydac C-18 column elution shown in FIG. 19.

Fraction 39 of the previous Mono Q chromatography was reduced in 5% β-mercaptoethanol in the presence of 4 M urea and heated for 5 mins at 95° C. The sample was pumped onto a Vydac C-18 column using an enrichment technique and the column was then washed with 5 ml of 0.1% trifluoroacetic acid. Elution of the proteins was accomplished with a gradient of 0-70% acetonitrile over 5 hrs in 0.1% trifluoroacetic acid (FIG. 19). Protein purity of the fractions which were fluorescamine positive was assessed by SDS-PAGE under non-reducing conditions using a 10% slab gel. The gel was silver stained to visualize protein (FIG. 20). Fractions 112 through 117 revealed a diffuse band at 35,000 molecular weight which was greater than 95% pure. The 40,000 dalton subunit and any other proteins present in fraction 39 remained bound to the C-18 column. These proteins (including the 40,000 dalton subunit) were finally eluted with a solution of 42% formic acid/40% 1-propanol.

Chemical Characterization

The ability to prepare homogeneous 35,000 subunit allowed for the determination of the amino acid composition and partial sequence analysis of the lower molecular weight subunit of the CLMF protein. Approximately 1 μg of 35 kDa subunit was subjected to hydrolysis, and its amino acid composition was determined (Table 7). Proline, cysteine, tryptophan were not determined (ND).

Amino-terminal sequence determination was attempted by automated Edman degradation on 100 pmol of the C-18 purified 35 kD subunit. Data from the first 20 cycles confirmed the sequence obtained by deduction as described in Example 2. Furthermore, the second amino acid was obtained in addition to amino acids 21 thru 26. These results may be summarized as follows:

| Cycle | 1 | 2 | 3 | 4 | 5 | 6 | 7 | 8 | 9 | 10 | 11 | 12 |
|---|---|---|---|---|---|---|---|---|---|---|---|---|
| Amino Acid | ? | N | L | P | V | A | T | P | D | P | G | M |
| Cycle | 13 | 14 | 15 | 16 | 17 | 18 | 19 | 20 | 21 | 22 | 23 | 24 |
| Amino Acid | F | P | ? | L | H | H | S | Q | N | L | L | R |
| Cycle | 25 | 26 | | | | | | | | | | |
| Amino Acid | A | V | | | | | | | | | | |

Therefore, the amino terminal sequence of the 35,000 dalton summarized as follows:
35,000 dalton subunit (SEQ ID NO: 23)
```
                    5                        10
NH₂-?-Asn-Leu-Pro-Val-Ala-Thr-Pro-Asp-Pro-Gly-Met- 15                   20                    25
Phe-Pro-?-Leu-His-His-Ser-Gln-Asn-Leu-Leu-Arg-Ala- 26
Val
``` where ? represents an undetermined residue.

TABLE 7

| Amino Acid | Mol % |
|---|---|
| Aspartic acid or asparagine | 10.9 |
| Threonine | 6.7 |
| Serine | 8.3 |
| Glutamic acid or glutamine | 14.9 |
| Proline | ND |
| Glycine | 6.1 |
| Alanine | 7.7 |
| Cysteine | ND |
| Valine | 6.3 |
| Methionine | 2.9 |
| Isoleucine | 4.5 |
| Leucine | 10.9 |
| Tyrosine | 3.2 |
| Phenylalanine | 4.4 |
| Histidine | 2.3 |
| Lysine | 5.6 |
| Arginine | 5.5 |
| Tryptophan | ND |

EXAMPLE 5

Determination of the Sequence of a Tryptic Fragment of CLMF

Mono Q fractions 36 and 37 from Example 1 were pooled (approximately 100 pmol/1.7 ml) and the volume (less 30 μ—see Example 6) reduced to 200 μl under a stream of helium. One hundred microliters of 0.1 M ammonium bicarbonate was added. Trypsin (Worthington Biochemical Corp., Freehold, N.J.) cleavage was performed at a substrate-to-enzyme ratio of 2:1 (w/w) at 37° C. for 20 hr. The resultant peptide fragments were reduced and carboxymethylated. This was accomplished by addition of 160 μl of 0.1 M Tris-HCl, pH 8.5/6 M guanidine-HCl. The volume was reduced to 200 IL under a stream of helium, and 4 µl of dithiothreitol (50 mg/ml) was added. The mixture was incubated at 37° C. for 4 hrs. After reductive cleavage of the disulfide bonds, [$^{14}$C] iodoacetic acid (4 mmol) was added and the resulting solution was incubated in the dark at room temperature for 10 min.

Figure 21:
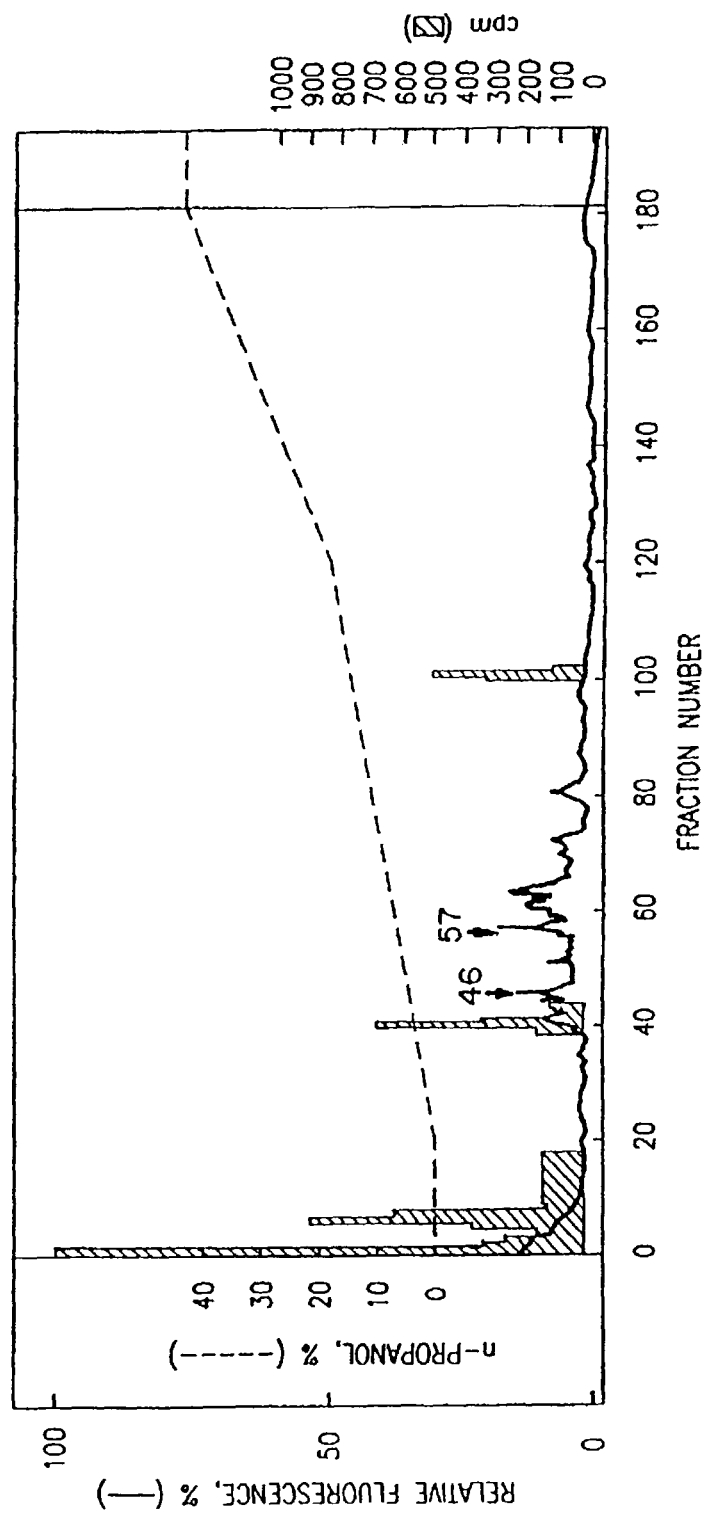
FIG. 21 is the elution pattern through a YMC ODS column of a tryptic digest of fractions 36 and 37 of the Mono Q Chromatography.

The resultant peptide fragments were isolated by reversed-phase HPLC (FIG. 21) on an S-5 120 Angstrom ODS column (2.6×50 mm, YMC, Inc., Morris Plains, N.J.). Peptides were eluted with a 1-propanol gradient in 0.9 M acetic acid, pH adjusted to 4.0 with pyridine. The amino acid sequence of the peptide found in fraction 46 was found to be (by automated Edman degradation): Asp-Ile-Ile--Lys-Pro-Asp-Pro-Pro-Lys (SEQ ID NO:24).

EXAMPLE 6

Determination of Internal Amino Acid Sequence Segments of CLMF

CLMF was purified as previously described in Example 1. Approximately 80 µl of protein was precipitated with 10% trichloroacetic acid. The precipitate was dissolved in 70% (v/v) aqueous formic acid at room temperature. An approximately 50-fold molar excess over methionine residues of cyanogen bromide (CNBr) in a small volume of 70% formic acid was added, with stirring, and the mixture was incubated in the dark under oxygen-free helium at room temperature for 48 hr. The mixture was diluted with 15 vol of water, divided into two equal portions and dried under a stream of helium for complete removal of the acid and by-products, the drying was repeated after further addition of water.

One of the portions (@40 µg) of fragmented CLMF was dissolved with 50 µl Laemmli sample buffer [Nature 227: 680-685 (1970)] containing 4% β-mercaptoethanol followed by exposure to 105° C. for 6 minutes. The sample was loaded into 3 wells of a minigel (1.0 mm thick) containing 17.5% polyacrylamide and electrophoresed according to Laemmli.

After electrophoresis, the gels were soaked in transfer buffer (10 mM 3-[cyclohexylamino]-1-propanesulfonic acid, 10% methanol, pH 11.0) for 30 min. During this time, a polyvinylidene difluoride (PVDF) membrane (Immobilon; Millipore; Bedford, Mass.) was rinsed with 100% methanol and stored in transfer buffer. The gel, backed with two sheets of PVDF membrane and sandwiched with blotting paper, was assembled into a blotting apparatus and electroeluted for min. at 0.5 Amps in transfer buffer. The PVDF membrane was washed in deionized H20 for 5 min and stained with 0.1% Coomassie Blue R-250 in 50% methanol for 5 min, and then destained in 50% methanol, 10% acetic acid for 5-10 min at room temperature. A number of smeared bands were observed.

Figure 22:
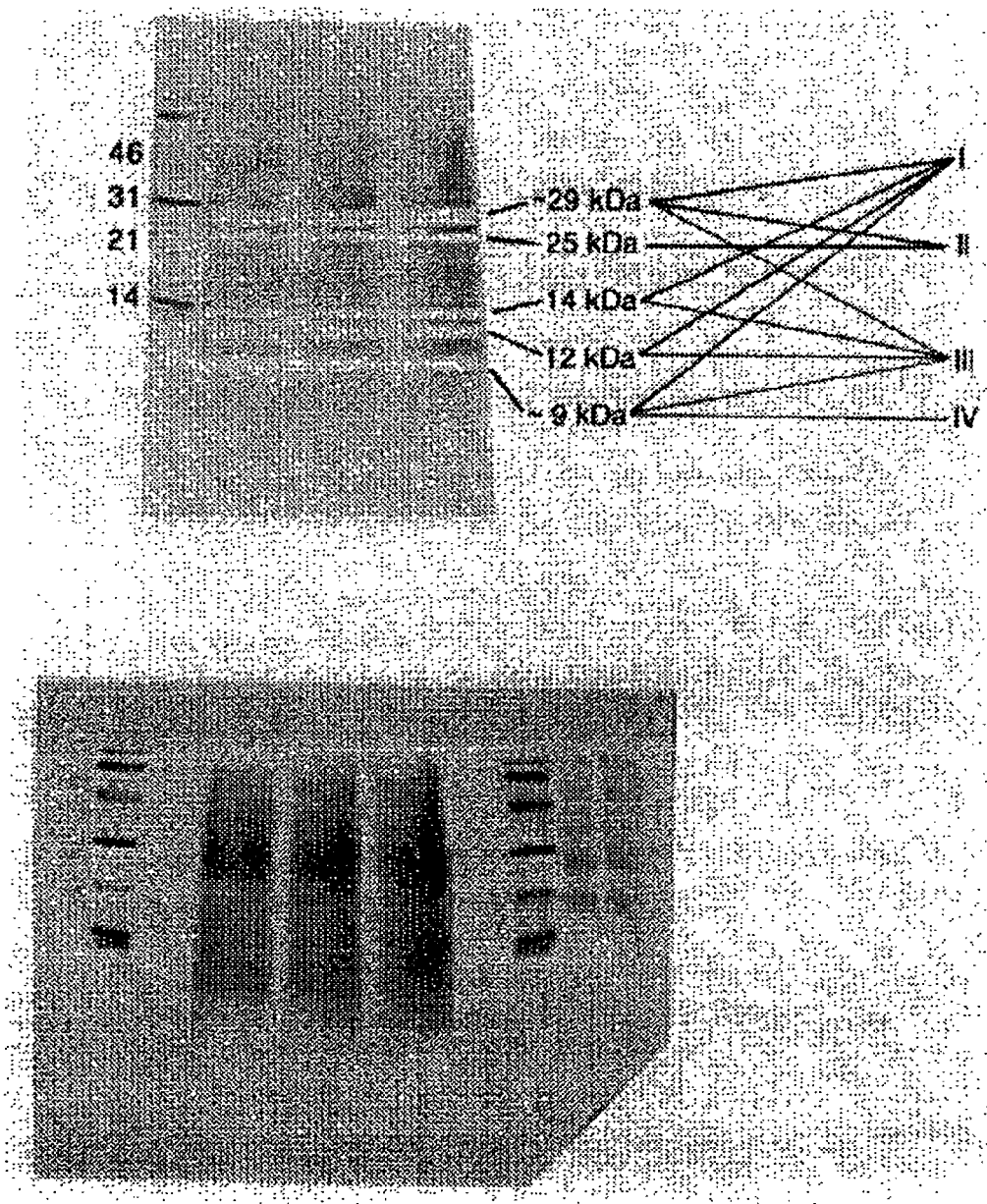
FIG. 22 shows a summary of the sequences obtained from CNBr fragments of CLMF produced in Example 6.

Five regions of the membrane were excised across the three last lanes containing the CLMF CNBr digest These regions were sequenced. A summary of the sequences obtained from the CNBr fragments of CLMF is shown on FIG. 22.

Figure 23:
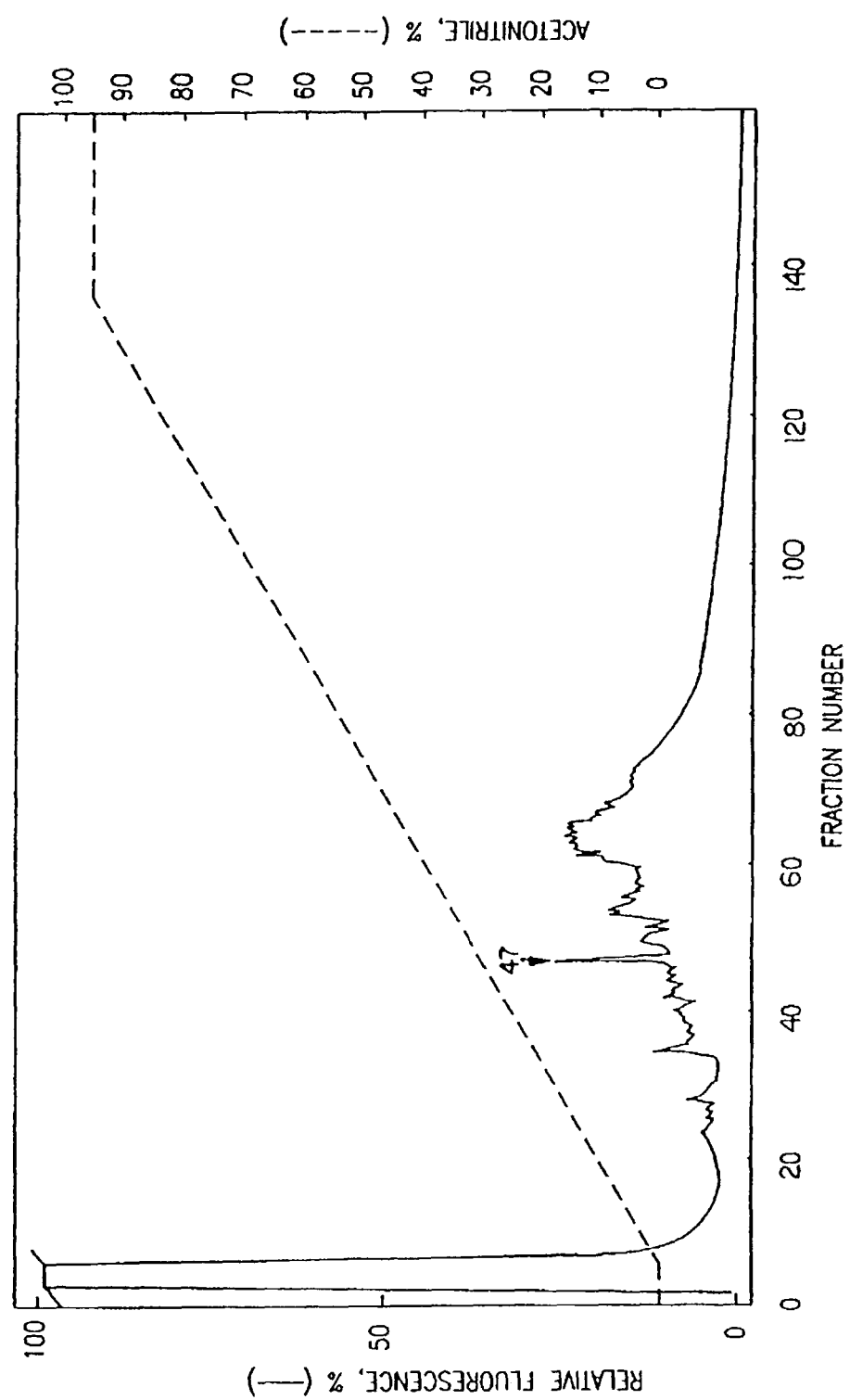
FIG. 23 shows the reverse-phase HPLC of peptide fragments of CLMF produced according to Example 6.

The second portion (@40 µg) of fragment CLMF was dissolved in 400-500 µl 88% formic acid containing 6 M guanidine HCl, 0.1 M Tris/HCl, 0.5 M NaOH, pH 8.0. The sample was pH adjusted to pH 4.0 with formic acid. The peptide fragments were isolated by reversed phase HPLC (FIG. 23) on a Vydac C$_4$ column (4.6×20 mm. The Sep/a/ra/tions Group, Hesperia, Calif.). Peptides were eluded with a 4.5 hr linear gradient of acetonitrile in 0.1% TFA. One of these peaks was sequenced and the amino acid sequence of this peptide was:

| Fraction No. | N-Terminal Sequence |
|---|---|
| 47 | V-D-A-V-H-K-L-K-Y-E-?-Y-T-S-(S?)-F-F-I-R-D-I-I-K-P- (SEQ ID NO: 25) (Starts at residue #190 of 40 kDa subunit) |

It is assumed or known that the above sequence is preceded by a Met residue "?" represents a "best-guessed" residue.

EXAMPLE 7

Purification of CLMF and 40,000 Dalton Subunit Using Affinity Chromatography

An affinity chromatography resin was prepared by covalently attaching 7B2 monoclonal antibody to activated agarose. Similarly, the below outlined purification could also be carried out by covalently coupling the antibody to silica or thin microporous membranes. The activated agarose was prepared as follows:

1. 100 ml Sepharose CL-6B was washed three times with 100 ml H$_2$O.
2. 100 ml of 1% sodium meta-periodate in H$_2$O was added to the resin and the suspension shaken at room temperature for 60 min.
3. The resin was washed with cold H$_2$O thoroughly.

The covalent attachment of 7B2 to the activated agarose was carried out as follows:

1. 9 ml of the activated agarose (described above) was suspended in 7 ml of 7B2 (@ 3.9 mg/ml) in phosphate buffered saline, pH 7.4.
2. Added 50.2 mg of cyanoborohydride was added to the gel suspension which was shaken overnight at 4° C.
3. The gel suspension was filtered and added to 7 ml of 1.0 M ethanolamine, pH 7.0 containing 50.2 mg of cyanoborohydride.

One millimeter of the above described resin (@ 2.6 mg IgG/ml gel) was packed in a column and washed extensively with phosphate buffered saline. Fractions from the Mono Q chromatography containing the 75 kDa, CLMF protein but with additional major contaminating proteins, were pooled (approx. 3.5×10$^6$ U TGF activity) and dialyzed extensively against PBS. This preparation was applied to the 7B2-Sepharose column at a rate of 5 ml/hr at room temperature. The column was washed with phosphate buffered saline (pH 7.4) until baseline absorbance monitoring at 280 nm was obtained. Adsorbed proteins were then eluded with 0.2 N acetic acid, 0.15 M NaCl, pH @3. Aliquots of fractions were assayed for TGF activity. Approximately 76% of the starting activity was recovered in the acid eluate.

Figure 24:
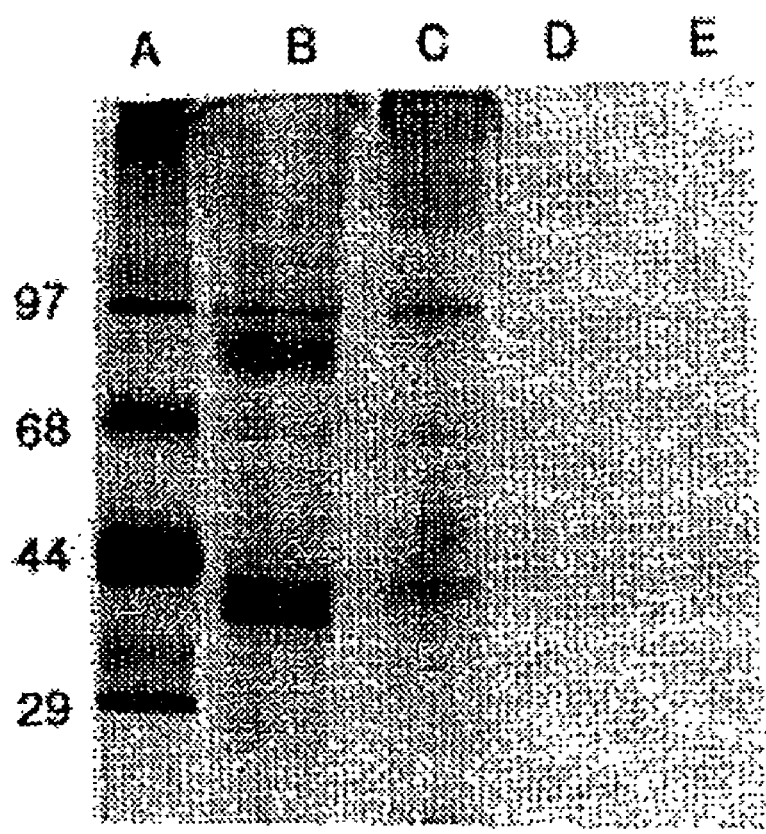
FIG. 24 is an SDS PAGE of pure CLMF and "free" unassociated 40 kDa subunit of CLMF purified by Affinity Chromatography according to Example 7.

Protein purity was assessed without reduction by SDS-PAGE [Laemmli, U.K. (1970) Nature (London) 227: 680-685)] using a 10% slab gel. Gels were silver stained [Morrissey, Anal. Biochem. 117:307-310] to visualize protein. The acid eluant contained pure CLMF and the "free" unassociated 40 kDa subunit of CLMF (FIG. 24).

EXAMPLE 8

Determination of the pI of CLMF

Thirty microliters of the pooled Mono Q fractions ,36 and 37 (see Example 5) were spotted onto a precast ampholine PAGplate gel, pH 3.5-9.5 (Pharmacia LKB Biotechnology) to determine the pI of CLMF. Based on pI standard markers, a major band was observed at pI 4.8 and a minor band at pi 5.2. Based on pH determination, the pi of these bands are 4.2 and 4.6 respectively.

EXAMPLE 9

Biologic Activities of Purified CLMF

Purified CLMF stimulated the proliferation of human PHA-activated lymphoblasts in the T cell growth factor assay (Table 8). The T cell growth factor activity of the purified CLMF recovered from the Mono Q column was compared to that of a standard preparation of human lymphokines in five separate experiments, and the specific activity of the purified CLMF was found to be $8.5 \pm 0.9 \times 10^7$ units/mg protein. In one experiment in which purified CLMF obtained from diphenyl HPLC was compared to the standard lymphokine preparation in the TGF assay, a specific activity of $5.2 \times 10^7$ units/mg protein was observed. When suboptimal concentrations of purified CLMF and human rIL-2 were tested in combination in the TGF assay, additive proliferation was observed (Table 8), up to the maximum proliferation caused by rIL-2 alone. However, proliferation caused by rIL-2 could be distinguished from proliferation due to CLMF in that the former was totally inhibited in the presence of a neutralizing goat anti-human IL-2 antiserum but the latter was not affected.

The ability of purified CLMF to activate cytotoxic effector cells was examined both in a 4-day LAK cell induction assay and in an overnight NK cell activation assay. In the LCI assay, purified CLMF at concentrations as high as 800 units/ml had little activity in the absence of IL-2 (Table 9). However, CLMF synergized with, low concentrations of human rIL-2 in causing LAK cell induction in as much as the lytic activity generated in the presence of both cytokines was significantly greater than the sum of the lytic activities observed in cultures containing either cytokine alone (Table 9). In the presence of rIL-2, purified CLMF was active at concentrations as low as 3 units/ml.

In contrast to the results in the 4-day LAK induction assay, purified CLMF was effective by itself in activating human NK cells in an overnight assay (Table 10). In this assay, CLMF was active at concentration as low as 1.6 units/ml. When CLMF was tested in combination with human rIL-2, the two cytokines together had, at best, additive effects in enhancing NK activity (Table 10).

In addition to its ability to enhance the lytic activity of nonspecific NK/LAK cells, CLMF also facilitated specific human cytolytic T lymphocyte (CTL) responses in vitro. CLMF increased the specific allogeneic CTL response to weakly immunogenic, gamma-irradiated HT144 melanoma cells (Table 11). In combination with a low concentration of rIL-2, CLMF also facilitated specific allogeneic human CTL responses to uv-irradiated HT144 melanoma cells, which did not elicit any detectable CTL response in the absence of added cytokines (Table 11). The specificity of the cytolytic effector cells generated in these studies was demonstrated by their ability to cause substantial lysis of $^{51}$Cr-labeled HT 144 melanoma cells but little or no lysis of K562 cells. In contrast, LAK cells which were generated in the same experiments by incubating low density lymphocytes with rIL-2 in the absence of hydrocortisone lysed the K562 cells to a much greater extent than HT144 melanoma cells. For further discussion of the specificity and identity of the cytolytic effector cells generated in assays such a those shown in Table 11, see Gately et al., J. Immunol. 136: 1274-1282, 1986.

Our results demonstrate that purified human CLMF by itself caused proliferation of activated human T lymphocytes, enhanced the cytolytic activity of human NK cells, and augmented human CTL responses. These activities of CLMF, which are similar to those of IL-2, suggest that: CLMF, like IL-2, should have immunoenhancing and antitumor effects when used as a single therapeutic agent in vivo. Clearly, CLMF may also have utility in stimulating the growth in vitro of NK/LAK cells and of activated T cells, such as may be derived from tumor infiltrating lymphocytes [S. L. Tupalian et al., J. Immunol. 142: 3714-3725, 1989]. In addition, purified CLMF synergized with low concentrations of rIL-2 in causing the generation of human LAK cells in culture and acted additively or synergistically with rIL-2 in facilitating specific CTL responses in vitro. These results suggest that the use of CLMF in combination with rIL-2 might constitute a more optimal antitumor therapy.

TABLE 8

Purified Human CLMF Stimulates the Proliferation of Human PHA-Activated Lymphoblasts

| | Cytokine Added: | | $^3$H-Thymidine Incorporated by |
|---|---|---|---|
| Expt. | Human CLMF[c] (u/ml) | Human rIL-2 (u/ml) | PHA-Activated Lymphoblasts (mean cpm + 1 S.E.M.) |
| 1[a] | 0 | 0 | 10,607 ± 596 |
| | 500 | 0 | 70,058 ± 1,630 |
| | 100 | 0 | 60,377 ± 1,927 |
| | 20 | 0 | 36,018 ± 321 |
| | 4 | 0 | 24,996 ± 669 |
| | 0.8 | 0 | 17,765 ± 790 |
| 2[b] | 0 | 0 | 9,976 ± 374 |
| | 200 | 0 | 60,980 ± 1,713 |
| | 50 | 0 | 38,817 ± 884 |
| | 12.5 | 0 | 18,885 ± 2,132 |
| | 3.1 | 0 | 13,648 ± 731 |
| | 0 | 16 | 80,041 ± 5,835 |
| | 0 | 4 | 21,282 ± 1,145 |
| | 0 | 1 | 11,241 ± 898 |
| | 50 | 4 | 62,050 ± 2,408 |
| | 12.5 | 4 | 40,628 ± 2,196 |
| | 3.1 | 4 | 31,144 ± 3,754 |

[a]All cultures in experiment 1 contained goat anti-human rIL-2.
[b]No cultures in experiment 2 contained goat anti-human rIL-2.
[c]Purified human CLMF from Mono Q FPLC.

TABLE 9

Purified Human CLMF Synergizes with Human rIL-2 in the Generation of Lymphokine-Activated Killer (LAK) Cells in 4-Day Cultures

| Cytokine Added: | | | |
|---|---|---|---|
| Human CLMF[b] (u/ml) | Human rIL-2 (u/ml) | % Specific K562 | $^{51}$Cr Release[a] from: Raji |
| 0 | 0 | 3 ± 1.7 | −1 ± 0.5 |
| 800 | 0 | 7 ± 0.3 | 1 ± 0.1 |
| 200 | 0 | 5 ± 1.1 | 1 ± 0.4 |
| 50 | 0 | 4 ± 3.0 | 0 ± 0.9 |
| 0 | 5 | 10 ± 2.4 | 2 ± 0.8 |
| 800 | 5 | 41 ± 4.0 | 11 ± 0.8 |
| 200 | 5 | 42 ± 1.9 | 11 ± 0.3 |
| 50 | 5 | 36 ± 2.7 | 9 ± 0.8 |
| 12.5 | 5 | 28 ± 2.1 | 7 ± 0.7 |
| 3.1 | 5 | 19 ± 0.8 | 5 ± 0.3 |
| 0.8 | 5 | 14 ± 1.2 | 3 ± 0.8 |

[a]Values represent the means ± 1 S.E.M. of quadruplicate determinations. The spontaneous $^{51}$Cr release values for K562 and Raji were 16% and 14%, respectively.
[b]Purified human CLMF from Mono Q FPLC.

TABLE 10

Purified Human CLMF Causes Activation of Natural Killer (NK) Cells in Overnight Cultures

| Cytokine Added: | | % Specific $^{51}$Cr Release[a] from Raji Cells at Effector/Target Ratio=: | |
|---|---|---|---|
| Human CLMF[b] (u/ml) | Human rIL-2 (u/ml) | 20/1 | 5/1 |
| 0 | 0 | 10 ± 0.6 | 5 ± 0.4 |
| 40 | 0 | 31 ± 0.4 | 14 ± 0.5 |
| 8 | 0 | 23 ± 2.1 | 12 ± 0.4 |
| 1.6 | 0 | 15 ± 0.3 | 10 ± 0.6 |
| 0.3 | 0 | 12 ± 1.2 | 9 ± 0.2 |
| 0 | 1 | 13 ± 0.4 | 6 ± 0.5 |
| 40 | 1 | 33 ± 2.0 | 17 ± 0.5 |
| 8 | 1 | 26 ± 0.8 | 13 ± 1.9 |
| 1.6 | 1 | 19 ± 1.1 | 11 ± 2.1 |
| 0.3 | 1 | 16 ± 1.0 | 10 ± 1.5 |
| 0 | 5 | 20 ± 1.3 | 13 ± 0.6 |
| 40 | 5 | 23 ± 2.0 | 12 ± 1.5 |
| 8 | 5 | 29 ± 1.1 | 16 ± 0.7 |
| 1.6 | 5 | 27 ± 1.2 | 13 ± 0.8 |
| 0.3 | 5 | 24 ± 1.8 | 13 ± 1.2 |
| 0 | 25 | 38 ± 1.4 | 19 ± 0.7 |

[a]Each value represents the mean ± 1 S.E.M. of quadruplicate determinations. The spontaneous $^{51}$Cr release was 9%.
[b]Purified human CLMF from Mono Q FPLC.

TABLE 11

PURIFIED HUMAN CLMF ENHANCES SPECIFIC HUMAN CYTOLYTIC T LYMPHOCYTE RESPONSES TO ALLOGENEIC MELANOMA CELLS IN VITRO

| Contents of Cultures: | | | | | % Specific $^{51}$Cr Release from[a] | | | |
|---|---|---|---|---|---|---|---|---|
| Lymphocytes (Percoll fraction[b]) | Hydrocortisone (M) | Melanoma Cells[c] | rIL-2 (u/ml) | CLMF (u/ml) | Expt. 1 | | Expt. 2 | |
| | | | | | HT144 | K562 | HT144 | K562 |
| 4 | $10^{-4}$ | | | | 6 ± 3 | −4 ± 1 | −2 ± 2 | 3 ± 4 |
| 4 | $10^{-4}$ | | 7.5 | 10 | −3 ± 1 | −1 ± 1 | −5 ± 1 | 4 ± 1 |
| 4 | $10^{-4}$ | HT$_{uv}$ | | | 0 ± 2 | −3 ± 1 | −2 ± 2 | 2 ± 1 |
| 4 | $10^{-4}$ | HT$_{uv}$ | | 10 | 7 ± 2 | −1 ± 1 | 13 ± 3 | −4 ± 1 |
| 4 | $10^{-4}$ | HT$_{uv}$ | 7.5 | | 5 ± 1 | 3 ± 1 | 1 ± 3 | 3 ± 3 |
| 4 | $10^{-4}$ | HT$_{uv}$ | 7.5 | 10 | 20 ± 3 | 10 ± 1 | 27 ± 9 | −6 ± 1 |
| 4 | $10^{-5}$ | HT$_\gamma$ | | | 17 ± 3 | −4 ± 1 | 10 ± 1 | 3 ± 1 |
| 4 | $10^{-5}$ | HR$_\gamma$ | | 10 | 39 ± 3 | −2 ± 2 | 33 ± 6 | 5 ± 3 |
| 1 + 2 | | | | 15 | 33 ± 4 | 67 ± 3 | 19 ± 1 | 47 ± 1 |

[a]In both experiments the contents of duplicate cultures were pooled, washed, resuspended in 1.2 ml TCM, and assayed for lytic activity undiluted and at 1:5 dilution. In experiment 1, the data shown were obtained using the 1:5 dilution of lymphocytes in the cytolytic assay, corresponding to a lymphocyte: target ratio of approximately 4:1. In experiment 2, significant lysis was seen only when lymphocytes were added undiluted to the lytic assay, and these data are shown in the table. The spontaneous $^{51}$Cr release from HT144 cells was 25% and 31% in experiments 1 and 2, respectively, and for K562 was 18% and 27% in experiments 1 and 2, respectfully.
[b]Percoll Fraction 4 contained high density lymphocytes recovered from the interface between the 45% and 58% Percoll layers, whereas Percoll fraction 1 + 2 contained lower density lymphocytes harvested from the interfaces between the 35% and 38% and between the 38% and 41% Percoll layers. Percoll fraction 4 contained CTL precursors but few LAK precursors; on the other hand, fraction 1 + 2 was rich in LAK cell precursors.
[c]HT$_{uv}$ and HT$_\gamma$ represent HT144 melanoma cells which had been uv-irradiated or gamma-irradiated, respectively.

EXAMPLE 10

Cloning of a cDNA Coding for the 40 kDa Subnit Of Human CLMF

1) Cell culture and isolation of polyA+ RNA

NC 37 cells (subclone 98) were grown in roller bottles as described above and induced with PMA and calcium ionophore for 15.5 hours. The cells were harvested, resulting in a frozen cell pellet of 1.11 grams, 5.25×10$^8$ cells. A portion of the culture was continued for 3 days, at which point the bioassay titer for CLMF activity read 2200 units/ml, indicating that the cells harvested for isolation of RNA had indeed produced the CLMF activity. Total RNA was isolated from the frozen cells by standard procedures and polyA+ RNA was obtained by affinity chromatography. The yield of polyA+ RNA was 2.5% (w/w) relative to the total amount of RNA input.

2) Establishment of a cDNA library.

2 µg of the above polyA+ RNA were reverse transcribed into cDNA using 150 ng random hexamers as primers. A library in lambda gt10 was established, and 1.5×10$^5$ clones were amplified for the screening.

3) Use of PCR to Generate a DNA Probe Specific for the 40 KDa CLMF Subunit cDNA

The partial N-terminal sequence of the purified 40 kDa protein is IWELKKDVYVVELDWYPDAP . . . (SEQ ID NO:35). Two primers for use in mixed primer PCR were designed and synthesized by standard procedures. The forward primer was designed as the coding strand corresponding to amino acids ELKKD (SEQ ID NO:36) in the above sequence, containing all possible codons for that sequence and having an extension at its 5' end including an EcoR1 site and three additional bases adding stability. The sequence of the forward primer is thus 5' ctc gaa ttc gaa/g c/ttn aaa/g aaa/g ga (SEQ ID NO:26), i.e., a 23mer with 64 different sequences. The reverse primer was designed in the same manner, to represent the antisense strand corresponding to the amino acid sequence YPDAP (SEQ ID NO:37) in the partial N-terminal 40 kDa sequence. The reverse primer thus has the sequence 5' ctc gaa ttc ngg ngc a/gtc ngg a/gta (SEQ ID NO:27) and is a 24 mer containing 256 different sequences. The symbol n stands for any one of the four possible bases a,g,c or t. The primers thus define an amplicon of 72 basepairs in length. After cutting with EcoR1 for generating cohesive ends for subcloning, the amplicon size-drops to 64 basepairs. Single-stranded cDNA was generated for use in the PCR as described in section 2 above, using polyA+ RNA from induced and, as a control, uninduced cells. 40 ng of either one of those cDNAs were amplified with forward and reverse primers in 100 µl of 10 mM Tris-HCl pH 8.3/50mM KCl/1.5 mM MgCl$_2$/0.01% gelatine/200 µM each of the four nucleotides/10 units Taq-polymerase/250 pmoles of each primer. The PCR parameters were as follows: initial denaturation was at 95° C. for 7minutes. Low stringency annealing was performed by cooling to 37° C. over 2 minutes, incubating 2 minutes at 37° C., heating 72° C. over 2.5 minutes, extending at 72° C. for 1.5 minutes, heating to 95° C. over 1 minute and denaturing at 95° C. for 1 minute; this low stringency annealing cycle was repeated once. Afterwards, 30 standard cycles were run as follows: 95° C. for 1 minute, 55° C. for 2 minutes, 72° C. for 2 minutes. A final extension was performed at 72° C. for 10 minutes. 10% of the total samples were run on a 4% agarose gel, stained and analyzed. The amplicon of the expected size was only detectable in the sample where induced cDNA had been amplified. The remainder of the sample was extracted with phenol, concentrated by precipitation with ethanol and redissolved in 42 µl of water. The sample was digested with 60 units of the restriction enzyme EcoR1 in 50 µl at 37° C. for 2 hours. The sample was subsequently run on a 6% polyacrylamide gel and the 64 bp amplicon was cut out of the gel and eluted by standard procedures. The DNA amplicon was subcloned into the EcoR1 site of the bluescript SK+ plasmid by standard procedures (5). Colonies obtained from the transformation of the E. coli strain DH5 alpha were picked and analyzed for the presence of the 64 bp insert. Two positive candidates were sequenced to determine the sequence of the cloned amplicon. It is clear from this analysis that the correct fragment was amplified, since the deduced amino acid sequence matches exactly the partial amino terminal amino acid sequence from the purified 40 kDa protein. This information was subsequently used to design a 54 bp long oligonucleotide probe that could be used for screening of the cDNA library. Two oligos were designed, with the following sequence: 5' gag cta aag aaa gat gtt tat gtc gta gaa ttc gat (SEQ ID NO:28)and 5' agg ggc atc cgg ata cca atc caa ttc tac gac ata. (SEQ ID NO:29). These two oligos are partially complementary to form the following structure:

```
                                            (SEQ ID NO: 28)
    5' gagctaaagaaagatgtttatgtcgtagaattggat 3'

(SEQ ID NO: 29)
    3' atacagcatcttaacctaaccataggcctacgggga 5'
```

Such a structure can be labelled by using klenow fragment and labelled nucleotides such that a high specific activity probe results for the screening of cDNA libraries.
4) Screening of cDNA Libraries
A total of 3×10⁵ clones from the amplified library were screened on 6 duplicate filters under the following conditions: 50 ml of 5×SSC/10× Denhardts/100 µg/ml denatured calf thymus DNA/20% formamide/0.1% SDS/1.5×10⁶ cpm of labelled 54 mer at 37° C. for 16 hours. The filters were subsequently washed in 2×SSC at 42° C. for 30 minutes, dried and exposed to X-ray film. After overnight exposure with an intensifying screen, 16 possible positives were picked and further analyzed by a second screening round. 10 rehybridizing phage were isolated and their DNA prepared. 8 of those 10 isolates looked identical, upon EcoR1 cutting releasing two fragments of 0.8 kb and 0.6 kb length, indicating a possible internal EcoR1 site. Upon blotting and hybridization with the screening probe, only the 0.6 kb fragment showed hybridization. The two fragments were subcloned separately into the EcoR1 site of the bluescript SK+ plasmid as described above and were completely sequenced. This analysis showed that both fragments align in one contiguous cDNA of about 1.4kb in length with a naturally occurring internal EcoR1 site, since both fragments upon translation showed the presence of reading frames coding for tryptic peptides that had actually been isolated from purified 40 Kd protein. The complete sequence of the 40 kDa subunit as deduced from the cDNA is shown in FIG. 25. The cDNA codes for one open reading frame of 328 amino acids. The protein starts with the initiating Met, followed by another 21 amino acids that make up a classical hydrophobic signal peptide. The N-terminus of mature purified 40 kDa subunit, i.e. IWELKKD . . . (SEQ ID NO:38), follows immediately after the signal sequence. The mature protein thus consists of 306 amino acids. The deduced protein sequence contains 4 possible N-linked glycosylation sites, two of which are present in isolated and sequenced tryptic peptides. One of these two sites is used in vivo for the attachment of a carbohydrate side chain. The molecular weight of the mature unglycosylated protein is 34699, the pI is 5.24. The corresponding mRNA is 2.4kb in length and is detectable in a northern blot in steady state RNA only from induced cells.

EXAMPLE 11

Cloning of a cDNA Coding for the 35 kDa Subunit of Human CLMF

Cell culture, isolation of mRNA and establishment of a cDNA library were as described earlier for the cloning of the 40 kDa subunit.
Use of Mixed Primer PCR to Generate a DNA Probe Specific for the 35 kDa Subunit cDNA
The partial N-terminal sequence of the purified 35 kDa subunit is ?NLPVATPDPGMFP?LHHSQNLLRAV . . . (SEQ ID NO:23). Two primers for use in mixed primer PCR were generated by standard procedures. The forward primer was designed as the coding strand corresponding to the amino acids DPGMF (SEQ ID NO:39)in the above sequence, containing all possible codons for that sequence and having an extension at its 5' end including an EcoR1 site and three additional bases adding stability. The sequence of this forward primer was thus 5' CTC GAA TTC GAT/C CCN GGN ATG TT-3'(SEQ ID NO:30), i.e. a 23 mer with 32 different sequences. The reverse primer was designed in the same manner, to represent the antisense strand corresponding to the amino acids NLLRA (SEQ ID NO:42) in the partial N-terminal sequence. The reverse primer had the sequence 5' CTC GAA TTC NGC NCG/T NAA/G NAA/G A/GTT (SEQ ID NO:31), i.e a 24mer with 4096 different sequences. In both primer sequences, N stands for all 4 bases. The two primers thus defined an amplicon 69 bases long. After cutting with EcoR1 for generating cohesive ends for subcloning, the amplicon size drops to 61 bases. About 3 µg of human genomic DNA were amplified with forward and reverse primers in 50 µl of 10 mM Tris-HCl pH 8.3/50 mM KCl/1.5 mM MgCl₂/0.01% gelatine/200 µM each of the four nucleotides/ 2.5 units of Taq polymerase/64 pmoles of forward and 2048 pmoles of reverse primer (to compensate for the greatly differing complexities of the two primers). The PCR cycling parameters were as follows: initial denaturation was at 95° C. for 7 minutes. Low stringency annealing was performed by cooling to 37° C. over 2 minutes, incubating at 37° C. for 2 minutes, heating to 72° C. over 2.5 minutes, extending at 72° C. for 1.5 minutes, heating to 95° C. over 1 minute and denaturing at 95° C. for 1 minute; this low stringency annealing cycle was repeated once. Afterwards, 40 standard cycles, were run as follows: 95° C. for 1 minute, 55° C. for 2 minutes and 72° C. for 3 minutes. A final extension was performed at 72° C. for 10 minutes. About 20% of the samples were run on a 6% polyacrylamide gel and an amplicon of the expected size was detected after staining the gel with ethidium bromide. The remainder of the sample was extracted with phenol, concentrated by precipitation with ethanol and redissolved in 17 µl of water. The sample was digested with 20 units of EcoR1 enzyme in 20 µl for 60 minutes at 37° C. The sample was subsequently fractionated on an 8% polyacrylamide gel and the 61 basepair amplicon was cut out of the gel and eluted by standard procedures. The DNA amplicon was subcloned into the EcoR1 site of the Bluescript plasmid SK+ by standard procedures. Colonies obtained from the transformation of the strain DH5 alpha were analyzed for the presence of the 61 basepair insert. Two candidates were sequenced to determine the sequence of the subcloned amplicon. One of the two clones contained the correct sequence, since translation of that sequence resulted in the amino acid sequence expected from the purified protein. Based on this information, two synthetic oligonucelotides were designed, with the following sequences:

```
                                         (SEQ ID NO: 32)
    5' gatccgggaatgttcccatgccttcaccactccc 3'

(SEQ ID NO: 33)
    3' gtacggaagtggtgagggttttggaggatgcccga 5'
```

Such a structure can be labelled using radiolabelled nucleotides with the Klenow fragment to very high specific activities for library screening.

Screening of a cDNA Library:

A total of $10^6$ clones from the amplified 16 h library were screened on 40 duplicate filters with the above probe under the following conditions 400 ml of 5×SSC/20% formamide/10×Denhardts/100 µg/ml denatured calf thymus DNA/0.1% SDS/3.8×$10^7$ cpm labelled probe at 37 ° C. overnight. The filters were subsequently washed in 2×SSC at 40°C. and exposed to X-ray film with a screen overnight. Six potential positives were picked from this first round of screening and analyzed by a second round of plaque hybridization, as above. One clone was picked for the final analysis. Upon preparing phage DNA, the clone was found to contain two EcoR1 fragments of about 0.8 kb and 0.3 kb in size. The two fragments were subcloned separately into the Bluescript SK+ plasmid and sequenced. This analysis showed that the two fragments align into one contigous sequence of about 1.1 kb total length with a naturally occurring internal EcoR1 site. The complete sequence of the cDNA and the deduced amino acid sequence for the 35 kDa CLMF subunit are shown in FIG. 26A-26C. The cDNA codes for an open reading frame of 219 amino acids, starting with the initiating Met at position 1. The following 21 amino acids constitute a classical hydrophobic signal sequence. Immediately following the signal peptide, the N-terminus of the mature 35 kDa protein starts with the sequence RNLPVAT . . . (SEQ ID NO:40). Purified 35 kDa protein had yielded the sequence ?NLPVAT . . . (SEQ ID NO:41). The mature 35 kDa protein thus consists of 197 amino acids, containing three possible N-linked glycosylation sites and 7 cys-residues. The molecular weight of mature unglycosylated protein is 22513, and the pI is 6.09. The corresponding mRNA is 1.4 Kb in length and is only detectable in RNA from cells that had been induced for CLMF for at least 6 hours.

EXAMPLE 12

Expression of Biologically Active Recombinant CLMF in COS-cells

The two subunits for CLMF were engineered for expression in mammalian cells as follows:

40 kDa Subunit

The two EcoR1 fragments constituting the full length cDNA for the 40 kDa CLMF subunit were ligated to an expression vector similar to pBC12 [See *B. Cullen*, Meth. Enzymology 152, 684,703, (1987)], except that the cDNA expression is driven off the SV40 early promoter/enhancer. Clones containing the two inserts in the proper orientation to each other were selected by colony hybridization with a synthetic oligonucleotide that spans the internal EcoR1 site in the 40 kDa cDNA. This oligonucleotide has the following sequence: 5' CTG AAG CCA TTA AAG AAT TCT CGG CAG GTG 3'(SEQ ID NO:34). It was labelled by kinasing using standard procedures. Clones were subsequently analyzed for proper orientation of insert to vector by the polymerase chain reaction procedure, using as forward primer a primer specific for sequences in the SV 40 early promoter and as reverse primer an oligonucleotide corresponding to the 40 kDa cDNA sequence positions no. 851-868. Clones with the correct orientation will give a PCR amplicon of 885 bp. Eight out of 20 clones tested gave the predicted fragment, and one was chosen for further study.

35 kDa subunit

The full length cDNA for the 35 kDa subunit was amplified out of the original lambda phage by PCR, using primers situated to the left and right of the EcoR1 site in lambda gt10 (primers were New England Biolab Articles No. 1231 and 1232). The resulting PCR amplicon was blunt-end ligated into the EcoRV site of the bluescript plasmid SK+ and the DNA propagated. DNA sequencing showed that the orientation of the cDNA insert within the plasmid was such that the end of the cDNA corresponding to the 5' end of mRNA was close to the ClaI site in the polylinker. The insert was thus released by cutting with ClaI, filling out this end with T4 DNA polymerase and cutting secondarily with Not I. The resulting fragment was gel-purified and subcloned into air expression plasmid based on the bluescipt vector and containing the SV40 early promoter to drive expression of inserted cDNAs. The sites in the expression plasmid used were a blunt-ended PstI site at the 5' end and a Not I site at the 3' end of the CDNA. One clone was chosen for further study after ascertaining its structure by PCR as above for the 40 kDa construct.

Expression of the Two cDNAs in COS-cells

The DNAs for the expression constructs of the 40 kDa and 35 kDa subunits were introduced into COS cells on 6 cm diameter plates by the DEAE Dextran transfection procedure ($7 \times 10^5$ cells/dish plated; 1 µg DNA per dish). 24 hours after the transfection, the cells were fed with standard tissue-culture medium containing 1% Nutridoma instead of the fetal bovine serum and the supernatants were collected after 40 hours and filtered through a 0.45µfilter.

Supernatant fluids from cultures of COS cells which had been transfected with cDNA encoding the 35 kDa CLMF subunit or the 40 kDa CLMF subunit or with both cDNAs were tested for CLMF activity in the T cell growth factor assay (Table 12). As shown in the table, COS cells which had been transfected with only one of the subunit cDNAs did not release biologically active CLMF into the culture fluid. However, COS cells which had been transfected with both subunit cDNAs produced biologically active CLMF. By comparing the amount of lymphoblast proliferation induced by the culture fluid from doubly transfected COS cells to the amount of proliferation induced by purified NC-37derived CLMF, the concentration of CLMF activity in the culture fluid was estimated to be 374 units/ml; Assuming a specific activity of $8 \times 10^7$ units/mg CLMF protein, this result suggests that the fluid from cultures of doubly transfected COS cells contained approximately 4.7 ng/ml of recombinant CLMF.

TABLE 12

T Cell Growth Factor Activity of Recombinant
CLMF Expressed in COS cells

| Cytokine added: | Concentration | $^3$H-Thymidine Incorporated by PHA-Activated Lymphoblasts (mean cpm ± 1 S.E.M.) |
|---|---|---|
| None | | 14,587 ± 343 |
| Natural CLMF* | 200 units/ml | 79,848 ± 854 |
| Natural CLMF | 40 units/ml | 59,093 ± 2029 |
| Natural CLMF | 8 units/ml | 39,180 ± 545 |
| Natural CLMF | 1.6 units/ml | 25,996 ± 763 |
| Supernatant fluid from cultures of COS cells transfected with: | | |
| 35 kDa CLMF subunit cDNA | 1/5 dilution | 15,332 ± 797 |
| 35 kDa CLMF subunit cDNA | 1/25 dilution | 12,149 ± 379 |
| 40 kDa CLMF subunit cDNA | 1/5 dilution | 14,883 ± 1039 |
| 40 kDa CLMF subunit cDNA | 1/25 dilution | 13,889 ± 110 |
| 35 kDa + 40 kDa CLMF subunit cDNAs | 1/5 dilution | 66,228 ± 166 |
| 35 kDa + 40 kDa CLMF subunit cDNAs | 1/25 dilution | 47,873 ± 275 |
| Mock transfected | 1/5 dilution | 14,368 ± 628 |
| Mock transfected | 1/25 dilution | 14,426 ± 173 |

*Purified NC-37-derived CLMF from Mono Q FPLC.

EXAMPLE 13

Preparation. Characterization and Purification of Hybridoma Antibodies

Lewis rats (Charles River Laboratories, Wilmington, Mass.) were initially immunized by the intraperitoneal route (i.p.) with partially purified CLMF mixed with an equal volume of Freund's complete adjuvant (Gibco). The rats were injected i.p. with booster immunization of CLMF mixed with Freund's incomplete adjuvant (Gibco) according to the schedule in Table 13. For preparation of activated spleen cells, one rat was injected i.v. with partially purified CLMF on two successive days starting 4 days prior to the cell fusion (Table 14). Spleen cells were isolated from this rat and fused with NSO cells at a ratio of 1:1 (spleen cells:NSO cells) with 35% polyethylene glycol (PEG 4000, E. Merck). The fused cells were plated at a density of 5×10$^4$ cells/well/ml in 48 well plates in IMDM supplemented with 15% FBS, glutamine (2 mM), beta-mercaptoethanol (0.1 mM), gentamycin (50: ug/ml), HEPES: (10 mM) and 15% P388D1 cell supernatant. Hybridoma supernatants were screened for specific CLMF antibodies in 4 assays: 1) immunoprecipitation of $^{125}$I-labelled CLMF, 2) immunodepletion of CLMF bioactivity, 3) western blotting with CLMF and 4) inhibition of $^{125}$I-CLMF binding to PHA-activated PBL blast cells. Hybridoma cell lines secreting anti-CLMF antibodies were cloned by limiting dilution. Antibodies were purified from large scale hybridoma cultures or ascites fluids by affinity chromatography on protein G bound to cross-linked agarose according to the manufacturer's protocol (Gammabind G, Genex, Gaithersburg, Md.).

Figure 27:
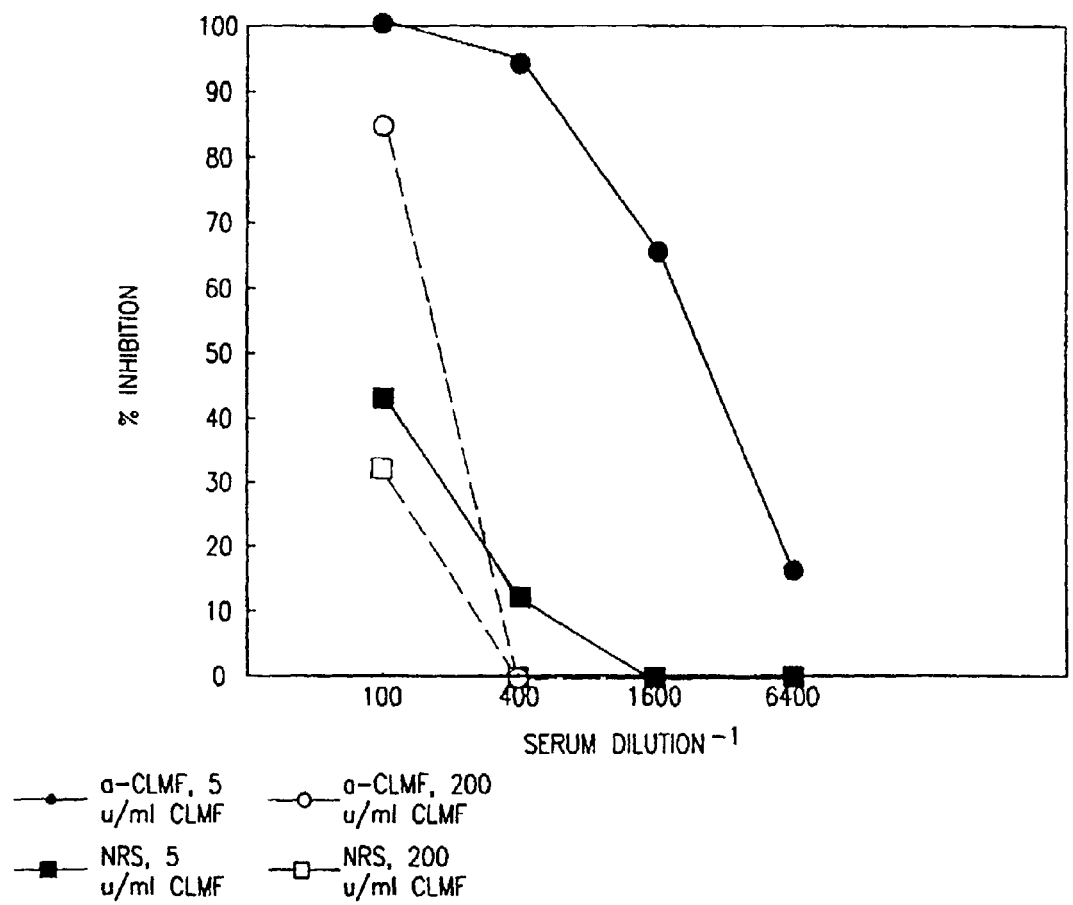
FIG. 27 shows the inhibition of CLMF bioactivity by serum from CLMF immunized and control rats.

Isolation and Identification of Monoclonal Antibodies Specific for CLMF. Serum isolated at the 3rd bleed from the rat immunized with partially purified CLMF (Table 13) neutralized CLMF bioactivity (5 units/ml) as determined in the TGF assay (FIG. 27). This neutralization could be blocked by adding excess CLMF (200 units/ml) demonstrating that the neutralization by the antiserum was specific for CLMF (FIG. 27). Normal rat serum did not neutralize CLMF bioactivity (FIG. 27). Spleen cells isolated from this rat were fused with NSO cells and the resulting hybridomas were initially screened for CLMF-specific antibodies by immunoprecipitation of $^{125}$I-labelled CLMF.

Figure 28:
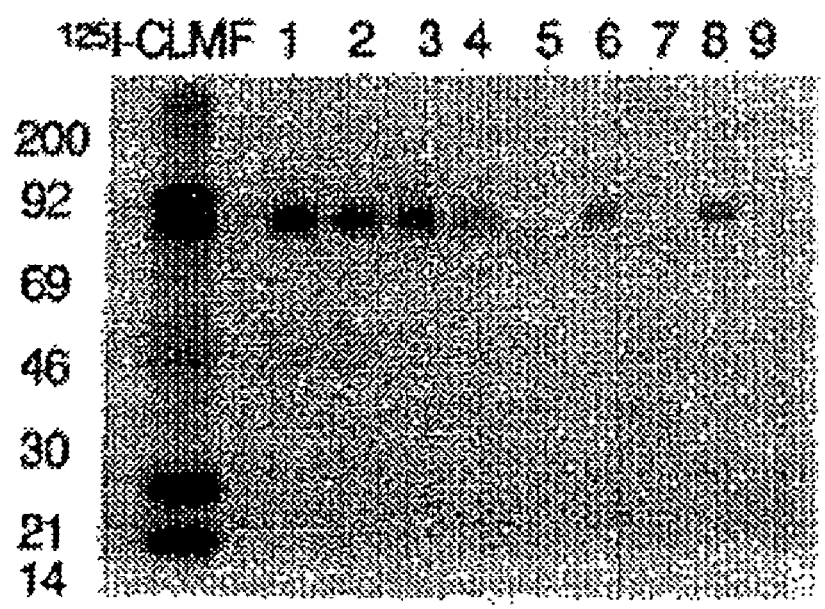
FIG. 28 shows SDS PAGE analysis of immunoprecipitation of $^{125}$I-CLMF b$_y$ monoclonal antibodies 4A1 (1), 4D1 (2), 8E3 (3), 9C8 (4) and control (5) and by immune rat serum (6 and 8) and normal rat serum (7 and 9).

The radioiodinated partially purified CLMF preparation contains predominantly the CLMF 75 kDa heterodimer, a small amount of the free CLMF 40 kDa subunit and two other proteins of approximately 92 kDa and 25 kDa (FIG. 28). The $^{125}$I-labelled CLMF preparation retained CLMF bioactivity in the TGF assay, indicating that the labelling procedure did not significantly alter the configuration of the CLMF molecule. The CLMF immunized rat serum immunoprecipitated the 75 kDa heterodimer and the free 40 kDa subunit (Lanes 6 and 8, FIG. 28) whereas normal rat serum did not immunoprecipitate these radiolabelled proteins (Lanes 7 and 9, FIG. 28). Four individual monoclonal antibodies also immunoprecipitated the 75 kDa heterodimer and the free 40 kDa subunit (FIG. 28) but did not immunoprecipitate the 92 kDa or 25 kDa labelled proteins. The immunoprecipitation assay identified twenty hybridomas which secreted anti-CLMF antibodies (Table 14). All the antibodies immunoprecipitated the radiolabelled 75 kDa heterodimer and the free 40 kDa subunit as determined by SDS/PAGE and autoradiography (data shown for 4 representative antibodies in FIG. 28).

Figure 29:
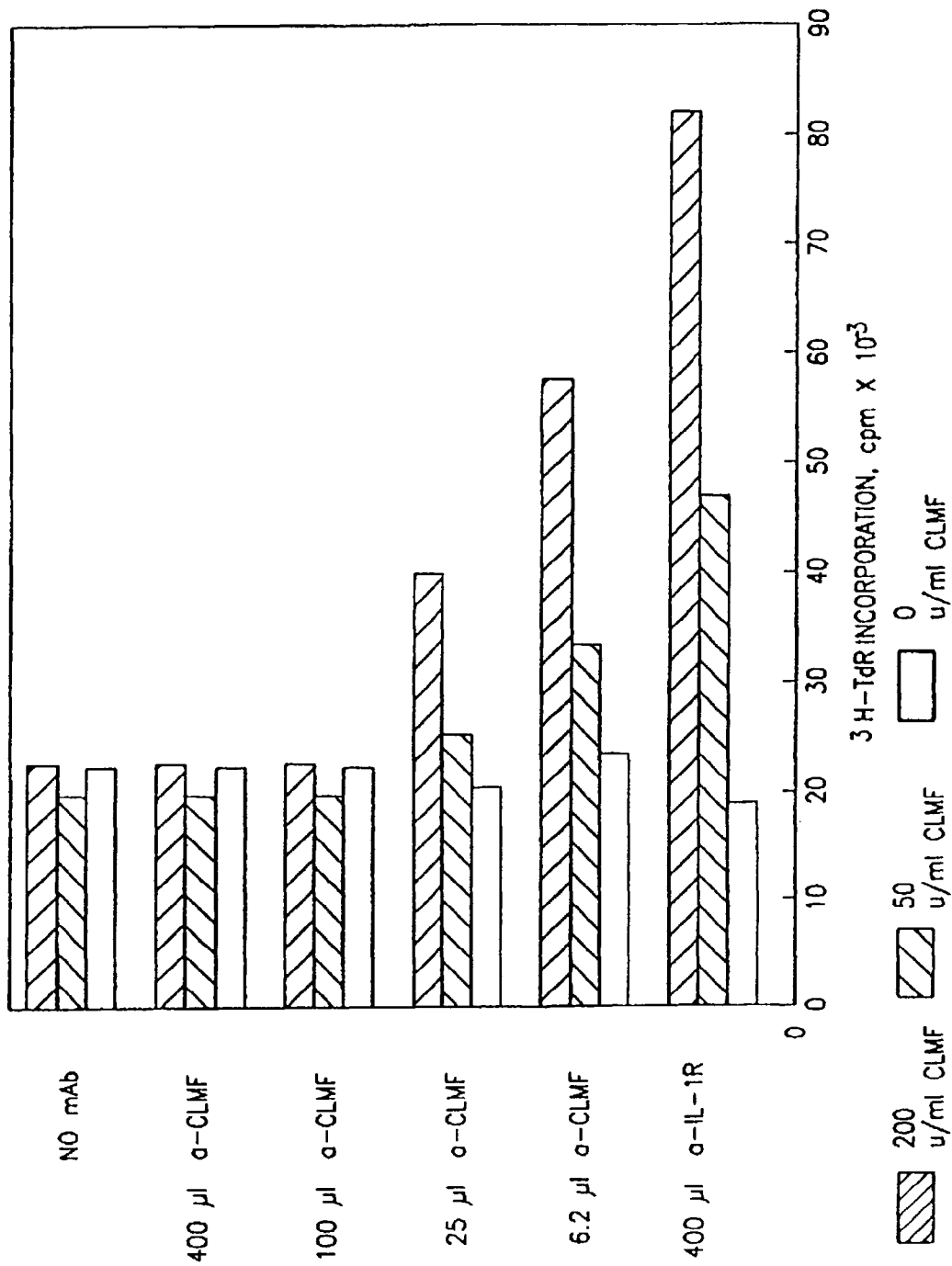
FIG. 29 shows the immunodepletion of CLMF bioactivity (TGF activity) by monoclonal anti-CLMF antibodies (a-CLMF).

After initially identifying specific CLMF antibodies in the immunoprecipitation assay, the antibodies were tested for their ability to immunodeplete CLMF bioactivity as assessed by the TGF and LAK cell induction assays. Increasing amounts of CLMF cause a dose dependent increase in the proliferation of PBL blasts in the TGF assay as measured by the incorporation of $^3$H-thymidine into the dividing blast cells (FIG. 29). Immunodepletion of CLMF activity by immobilized anti-CLMF antibodies occurs in a dose dependent manner (FIG. 29). Aliquots (0.4 and 0.1 ml) of hybridoma supernatant solution will completely deplete 50 and 200 units/ml of CLMF activity from the culture medium. 0.025 ml of supernatant solution will completely deplete 50 units/ml but only approximately 50% of 200 units/ml. 0.0062 ml of hybridoma supernatant shows even less depletion of 50 and 200 units/ml of CLMF. An aliquot (0.4 ml) of an anti-IL-1 receptor antibody supernatant solution shows no immunodepletion of CLMF bioactivity.

Figure 30:
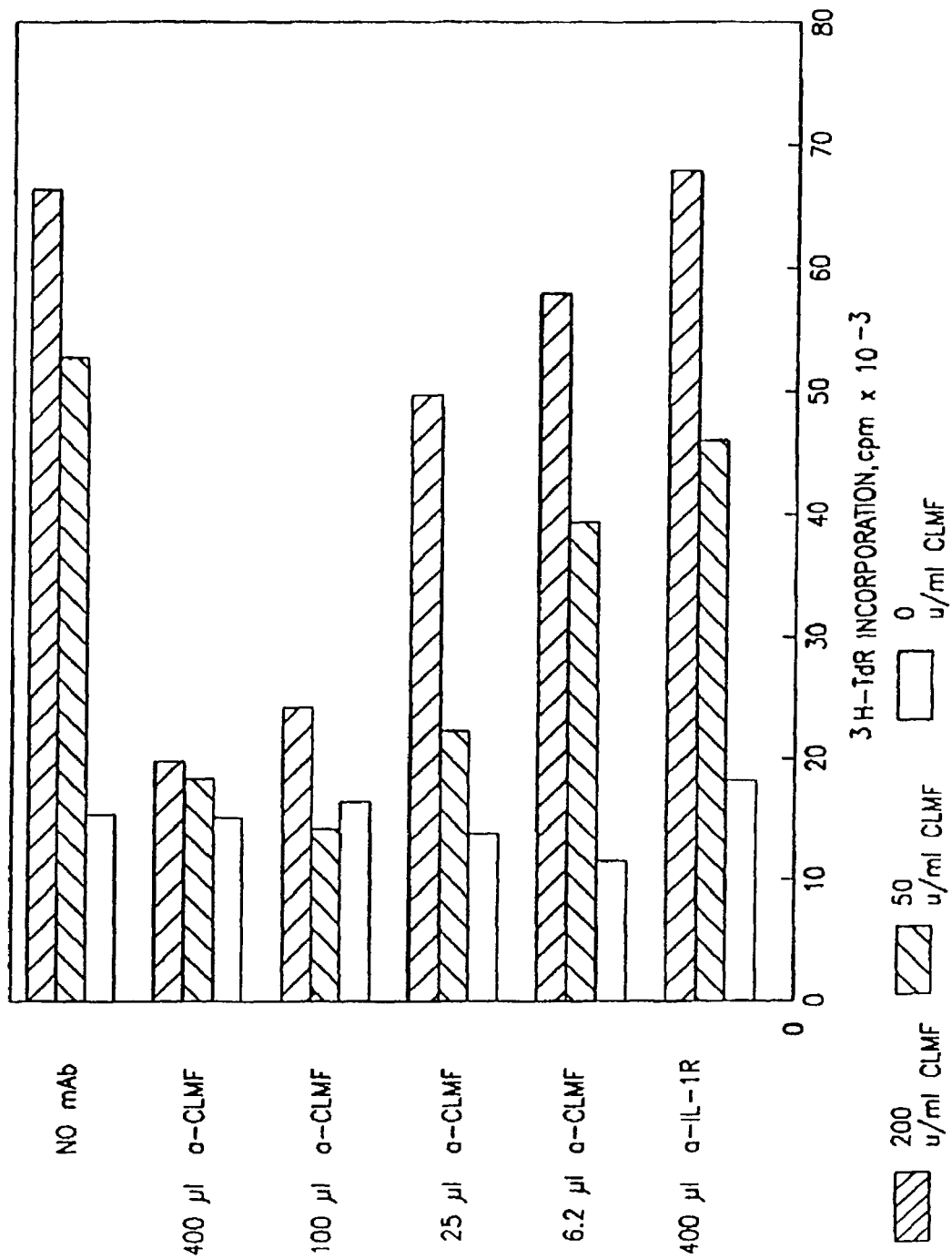
FIG. 30 shows immunodepletion of CLMF bioactivity (LAK induction activity) by monoclonal anti-CLMF antibodies (a-CLMF).

Increasing amounts of CLMF also cause a dose dependent increase in the lysis of target cells by LAK cells as measured by the release of $^{51}$Cr in the LAK cell induction microassay (FIG. 30). The immobilized anti-CLMF antibodies also deplete in a dose dependent manner the CLMF activity in the LAK cell induction assay (FIG. 30).

These data confirm that the antibodies which immunoprecipitate the 1 5 75 kDa labelled protein from the radiolabelled partially purified CLMF preparation are specific for CLMF. The data also demonstrate that the radiolabelled 75 kDa protein is the protein responsible for CLMF bioactivity.

Figure 31:
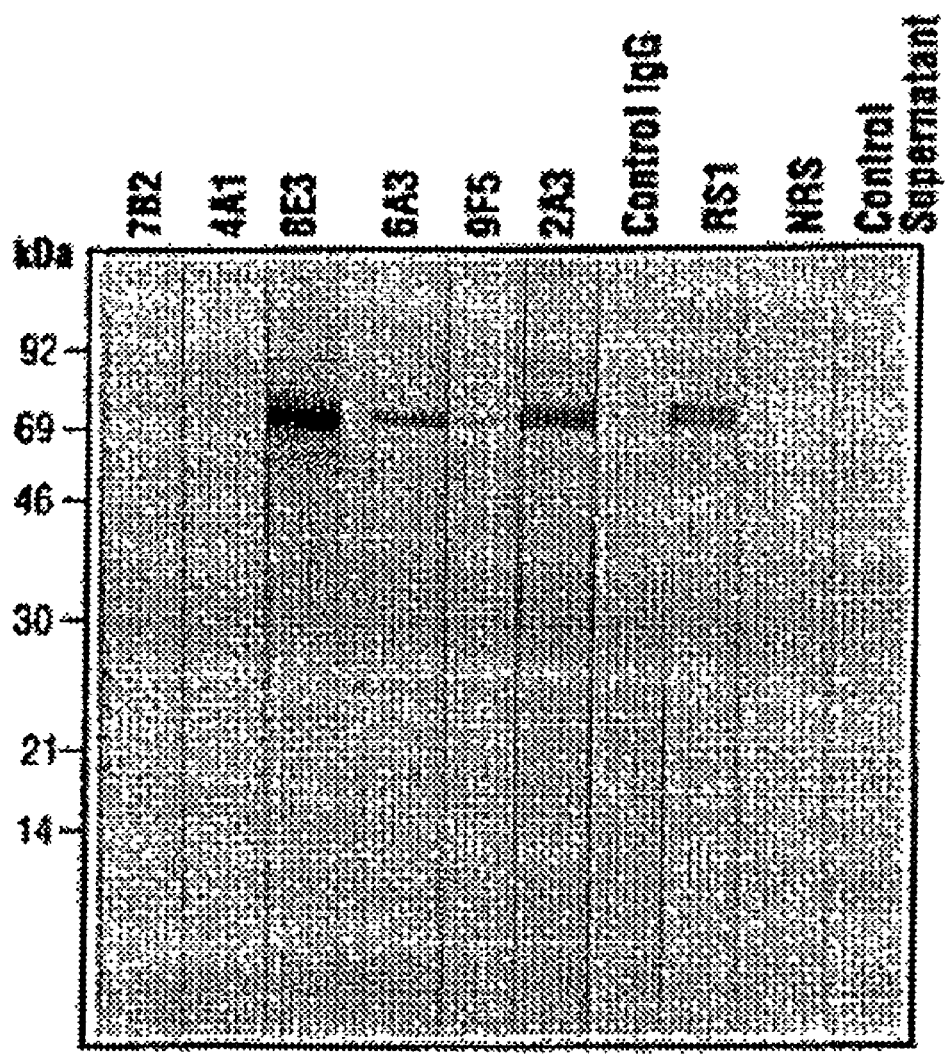
FIG. 31 shows Western blot analysis of the reactivity of monoclonal and rat polyclonal anti-CLMF antibodies with CLMF 75 kDa heterodimer.

Identification of the CLMF Subunit Bound by the Monoclonal Antibodies. CLMF is a 75 kDa heterodimer protein composed of 40 kDa and 35 kDa subunits. Western blot analysis was used to determine if the monoclonal anti-CLMF antibodies recognized the 40 kDa or the 35 kDa subunits. Highly purified 75 kDa CLMF heterodimer was separated by non-reducing SDS/PAGE and transferred to nitrocellulose membrane (FIG. 31). In addition, purified CLMF, which was composed of approximately 95% free 40 kDa subunit and 5% 75 kDa heterodimer, was separated by both non-reducing and reducing SDS/PAGE and the proteins were transferred to nitrocellulose membrane (FIG. 32). Individual nitrocellulose strips containing the non-reduced 75 kDa CLMF heterodimer (FIG. 31), the non-reduced 40 kDa subunit (top panel FIG.

32) and the reduced 40 kDa subunit (bottom panel FIG. 32) were probed with monoclonal anti-CLMF antibodies, control monoclonal antibody, rat anti-CLMF serum and control rat serum. The monoclonal anti-CLMF and rat polyclonal anti-CLMF antibodies bind specifically to an approximately 75 kDa heterodimer on the strips containing non-reduced 75 kDa CLMF while the control antibody preparations do not show this binding activity (FIG. 31). All the monoclonal and rat polyclonal anti-CLMF antibodies recognize the non-reduced 40 kDa subunit (top panel, FIG. 32). However, only the rat polyclonal antiserum and three monoclonal antibodies, 8E3, 9F5 and 22E7, bind to reduced 40 kDa subunit protein (bottom panel, FIG. 32). These data demonstrated that all the monoclonal antibodies were specific for the 40 kDa subunit of CLMF.

Figure 33:
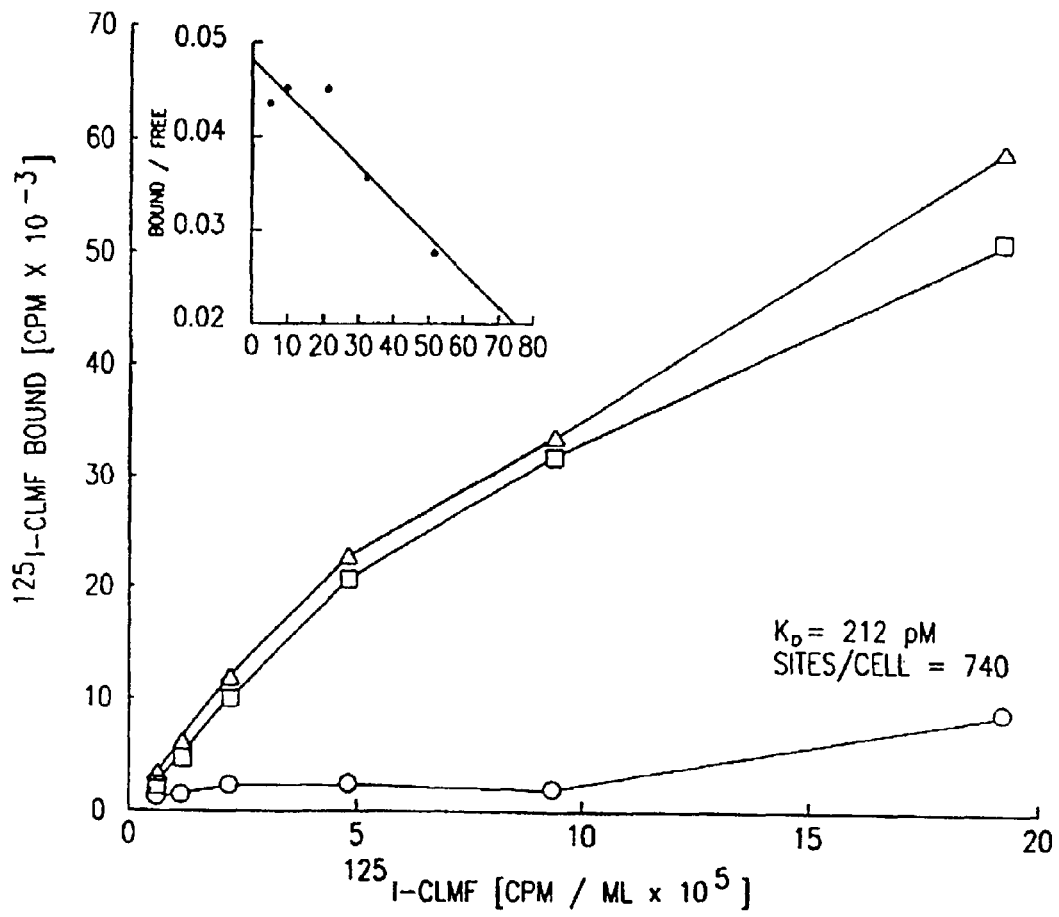
FIG. 33 shows the binding of $^{125}$I-CLMF to PHA activated peripheral blood lymphocyte (PBL) lymphoblats.
Figure 34:
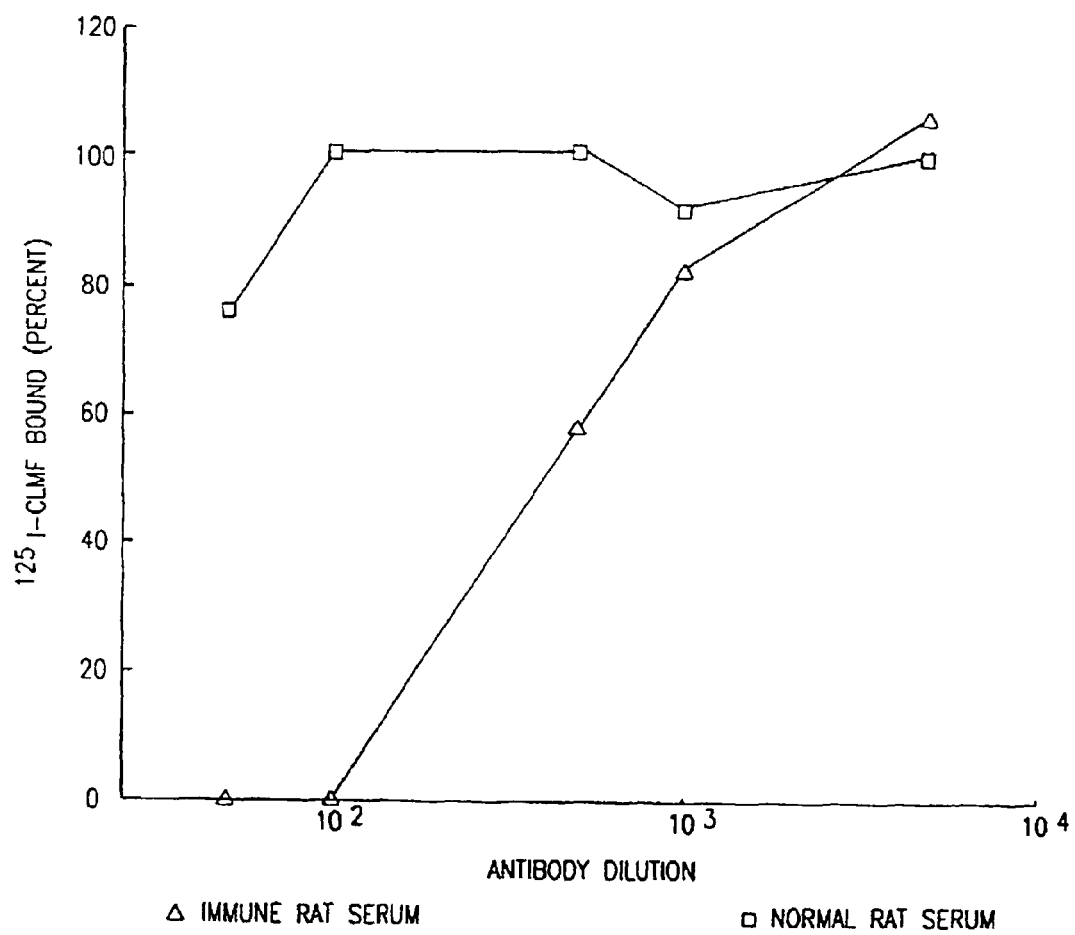
FIG. 34 shows the inhibition of $^{125}$I-CLMF binding to PHA-activated PBL blast cells by rat anti-CLMF serum. The data are expressed as amount (% bound) of $^{125}$I-CLMF binding to the cells in the presence of the indicated concentrations of serum when compared to the to the total specific binding in the absence of serum.

Identification of a CLMF Receptor on PHA-Activated Lymphoblasts. The previous data demonstrated that the monoclonal anti-CLMF antibodies immunoprecipitated $^{125}$I-labelled CLMF, immunodepleted CLMF bioactivity and bound to the 40 kDa subunit of CLMF. However, the antibodies present in the hybridoma supernatant solutions could not be directly tested for their ability to neutralize CLMF bioactivity in the TGF or LAK cell induction assays due to non-specific inhibitory effects of supernatant solutions containing control antibodies. Our previous work with IL-2 monoclonal antibodies demonstrated that antibodies which would block $^{125}$I-IL-2 binding to IL-2 receptor bearing cells would also neutralize IL-2 bioactivity. Since receptor binding assays ate usually unaffected by addition of hybridoma supernatant solutions or other substances, a CLMF receptor binding assay was developed to evaluate the anti-CLMF antibodies for inhibitory/neutralization activity. A CLMF receptor binding assay was configured-with $^{125}$I-labelled CLMF and the PHA-activated peripheral blood lymphoblasts (FIG. 33). The binding of $^{125}$I-CLMF to the PHA-activated lymphoblasts was saturable and specific (FIG. 33). Scatchard plot analysis [See Scatchard. G. Ann. N.Y. Acad. Sci. 51, 660-672 (1949)] of the equilbrium binding data indicated that the apparent dissociation constant for $^{125}$I-CLMF binding to the receptor is approximately 200 pM and that each lymphoblast has about 700-800 receptors. Since the serum from the rat immunized with CLMF showed neutralization of CLMF bioactivity, it was tested for inhibition of $^{125}$I-CLMF binding to the lymphoblasts (FIG. 34). The rat immune serum blocks 50% of $^{125}$I-labelled CLMF binding at approximately a 1/500 dilution, while the control rat serum does not show any inhibition at this dilution. With the specificity of the receptor binding assay established, hybridoma supernatant solutions were tested for antibodies which would inhibit $^{125}$I-CLMF binding to lymphoblasts.

Figure 35:
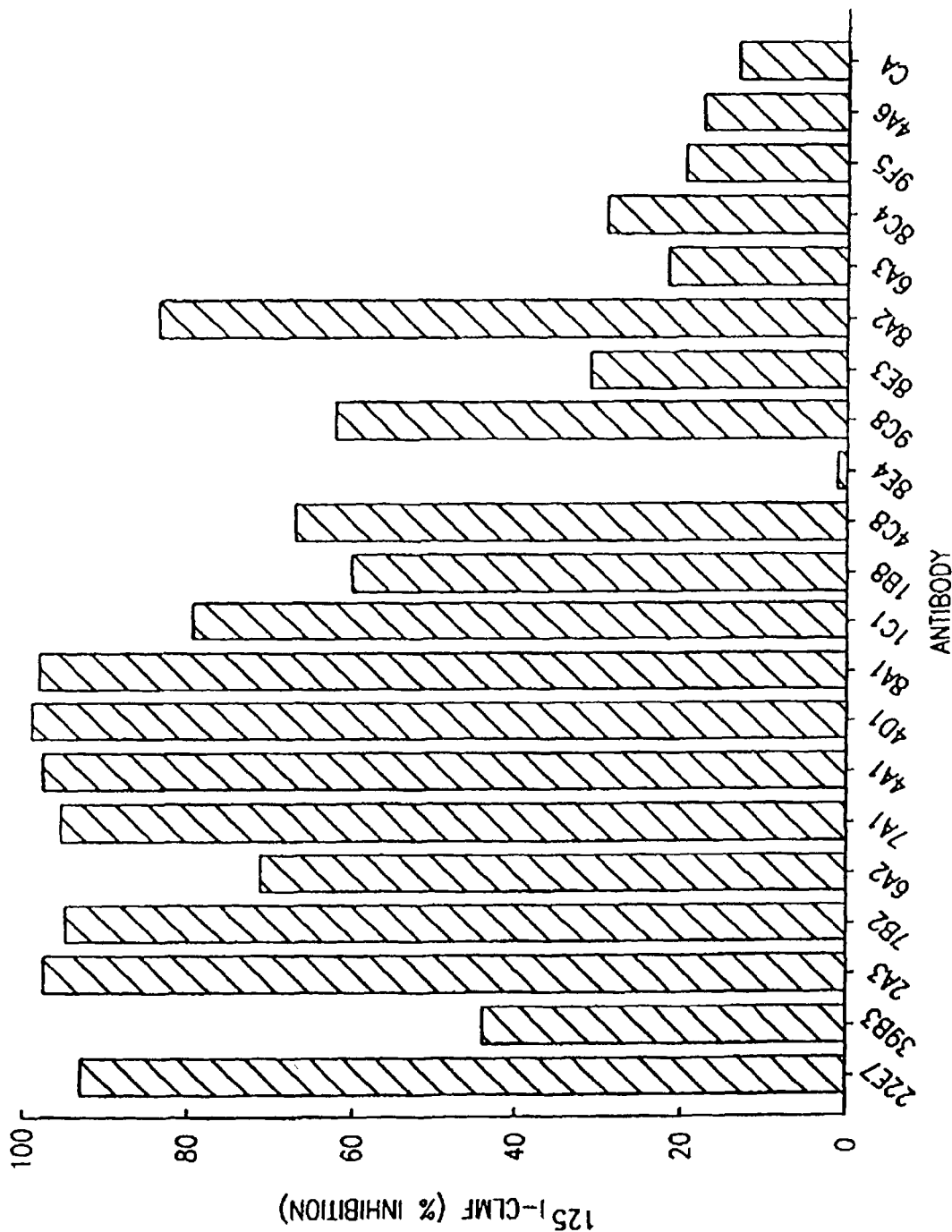
FIG. 35 shows the inhibition of $^{125}$I-CLMF binding to the PHA-activated PBL blast cells by monoclonal antibody supernatants. The data are expressed as % inhibition of $^{125}$I-CLMF binding to the cells in the presence of a 1:1 dilution of supernatant when compared to the total specific binding in the absence of antibody supernatant.

The degree of inhibition of $^{125}$I-CLMF binding to the lymphoblasts was determined at a 1/2 dilution of each hybridoma supernatant solution (FIG. 35). Twelve hybridoma supernatant solutions inhibited by greater than 60% $^{125}$I-CLMF binding to the lymphoblasts. The antibodies present in these supernatant solutions have been classified as inhibitory/neutralizing antibodies. Six hybridoma supernatant solutions inhibited $^{125}$I-labelled CLMF binding by less than 40% and were classified as non-inhibitory/non-neutralizing antibodies. Control antibody inhibited by approximately 10% the $^{125}$I-CLMF binding to the lymphoblasts.

Figure 36:
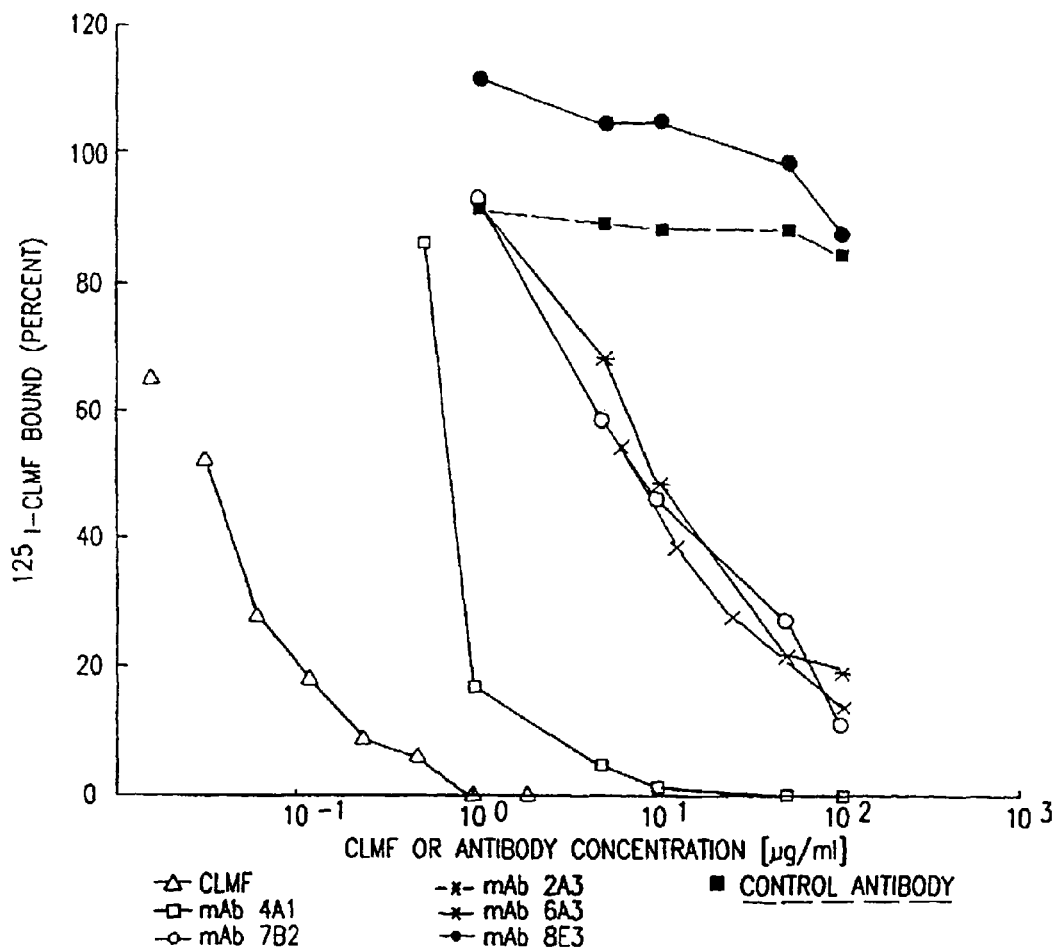
FIG. 36 shows the inhibition of $^{125}$I-CLMF binding to PHA-activated PBL blast cells by various concentrations of purified monoclonal antibodies. The data are expressed as the amount (% cpm bound) of $^{125}$I-CLMF binding to the cells in the presence of the indicated concentrations of antibody when compared to the total specific binding in the absence of antibody.

Three inhibitory antibodies, 7B2, 2A3 and 4A1, and two non-inhibitory antibodies, 6A3 and 8E3, were purified from ascites fluid by protein G affinity chromatography on GammaBind G (Genex, Gaithersburg, Md.) columns. Antibodies 4A1, 2A3 and 7B2 inhibit in a dose dependent manner $^{125}$I-CLMF binding to the lymphoblasts with IC$_{50}$ concentrations of 0.7 µg/ml, 7 µg/ml and 9.5 µg/ml, respectively (FIG. 36). Antibodies 6A3 and 8E3 do not block $^{125}$I-CLMF binding at concentrations of 100 µg/ml (FIG. 36). These data demonstrated that the original classification of each antibody as either inhibitory or non-inhibitory was correct.

Direct Neutralization of CLMF Bioactivity by Antibodies. To determine if the antibodies classified as inhibitory by the CLMF receptor binding assay would directly neutralize CLMF bioactivity, each inhibitory antibody was tested for neutralizing activity in the TGF assay (Table 15). Two inhibitory antibodies, 4A1 and 7B2, demonstrated a dose dependent neutralization of CLMF bioactivity (40 units/ml) from 0.03 to 100 µg/ml, with IC$_{50}$ concentrations of approximately 1 µg/ml and 80 µg/ml, respectively. These data confirmed that antibodies inhibiting $^{125}$I-CLMF binding to the CLMF receptor would also neutralize CLMF bioactivity.

TABLE 13

Immunization Schedule:

| Date | CLMF(10$^8$ units/mg) units | mg | Total Protein (µg) | Spec. Activity (U/mg) | Purity (%) |
|---|---|---|---|---|---|
| Mar. 28, 1989 | 1 × 10$^4$ | .1 µg | 15 | 6.7 × 10$^5$ | 6.7 |
| Apr. 10, 1989 | 1.2 × 10$^4$ | .1 µg | ? | 6 × 10$^5$ | .6 |
| May 3, 1989 | 1st bleed | | | | |
| May 18, 1989 | 2.2 × 10$^5$ | 2 µg | 75 | 2.9 × 10$^6$ | 2.9 |
| Jun. 7, 1989 | 2nd bleed | | | | |
| Jun. 29, 1989 | 6.3 × 10$^4$ | .63 µg | 83 | 7.5 × 10$^5$ | .75 |
| Jul. 21, 1989 | 1.2 × 10$^5$ | 1.2 µg | 24 | 5 × 10$^6$ | 5.0 |
| Aug. 2, 1989 | 3rd bleed | | | | |
| Oct. 19, 1989 | 2.1 × 10$^6$ (i.v.) | | | | |
| Oct. 20, 1989 | 2.1 × 10$^6$ (i.v.) | | | | |
| Oct. 23, 1989 | Fusion | | | | |

TABLE 14

Monoclonal Anti-CLMF Antibodies (40 kDa Subunit Specific)

| Antibody | Western Blot[1] Red. | N.R. | $^{125}$I-CLMF/Receptor Assay (% Inhibition)[2] | Neutralization of Bioactivity[3] |
|---|---|---|---|---|
| Inhibitory/Neutralizing | | | | |
| 7B2 | − | ++ | 95 | + |
| 2A3 | − | ++ | 99 | + |
| 1B8 | − | +/− | 60 | ND[4] |
| 1C1 | − | ++ | 81 | ND |
| 4A1 | − | + | 98 | + |
| 4C8 | ND | ND | 68 | ND |
| 4D1 | − | + | 100 | ND |
| 6A2 | − | +/− | 75 | ND |
| 7A1 | +/− | ++ | 94 | ND |
| 8A1 | − | + | 99 | ND |
| 8A2 | − | ++ | 83 | ND |
| 9C8 | − | + | 62 | ND |
| 22E7 | ++ | ++ | 91 | ND |
| Non-Inhibitory/Non-Neutralizing | | | | |
| 8E3 | + | ++ | 35 | − |
| 9F5 | + | ++ | 18 | ND |
| 4A6 | − | − | 17 | ND |
| 6A3 | − | + | 20 | − |
| 8C4 | − | ++ | 33 | ND |
| 8E4 | − | ++ | 1 | ND |

TABLE 14-continued

Monoclonal Anti-CLMF Antibodies (40 kDa Subunit Specific)

| Antibody | Western Blot[1] | | $^{125}$I-CLMF/Receptor Assay | Neutralization of Bioactivity[3] |
|---|---|---|---|---|
| | Red. | N.R. | (% Inhibition)[2] | |
| 39B3 | ND | ND | 46 | ND |
| Control | − | − | 12 | − |

[1]Western blots: N.R. is non-reduced and Red. is reduced SDS/PAGE For the western blots, a CLMF sample containing 5% 75 kDa heterodimer and 95% free 40 kDa subunit were separated on 10% SDS/PAGE and western blots prepared as described in methods. The blots were scored as strongly positive (++), positive (+), weakly positive (+/−) negative (−).
[2]CLMF receptor binding assay: An antibody was considered inhibitory if it would block more than 60% of radiolabelled CLMF binding to the PHA activated PBL blasts
[3]Neutralization of CLMF bioactivity as assessed by the TGF assay: An antibody was considered neutralizing if it would block more more than 50% proliferation at 20 μg/ml. The results are presented as positive (+) or negative (−).
[4]ND: Not Determined

TABLE 15

Monoclonal Anti-CLMF Antibodies (40 kDa Subunit Specific)

| Antibody | Western Blot | | $^{125}$I-CLMF/Receptor Assay | Neutralization of Bioactivity |
|---|---|---|---|---|
| | Red. | N.R. | (% Inhibition) | |
| Inhibitory/Neutralizing | | | | |
| 7B2 | − | ++ | 95 | + |
| 2A3 | − | ++ | 99 | + |
| 1B8 | − | +/− | 60 | ND |
| 1C1 | − | ++ | 81 | ND |
| 4A1 | − | + | 98 | + |
| 4C8 | ND | ND | 68 | ND |
| 4D1 | − | + | 100 | ND |
| 6A2 | − | +/− | 75 | ND |
| 7A1 | +/− | ++ | 94 | ND |
| 8A1 | − | + | 99 | ND |
| 8A2 | − | ++ | 83 | ND |
| 9C8 | − | + | 62 | ND |
| 22E7 | ++ | ++ | 91 | ND |
| Non-Inhibitory/Non-Neutralizing | | | | |
| 8E3 | + | ++ | 35 | − |
| 9F5 | + | ++ | 18 | ND |
| 4A6 | − | − | 17 | ND |
| 6A3 | − | + | 20 | − |
| 8C4 | − | ++ | 33 | ND |
| 8E4 | − | ++ | 1 | ND |
| 39B3 | ND | ND | 46 | ND |
| Control | − | − | 12 | − |

1: Western blots: N.R. is non-reduced and Red. is reduced SDS/PAGE For the western blots, a CLMF sample containing 5% 75 kDa heterodimer and 95% free 40 kDa subunit were separated on 10% SDS/PAGE and western blots prepared as described in methods. The blots were scored as strongly positive (++), positive (+), weakly positive (+/−) and negative (−).
2. CLMF receptor binding assay: An antibody was considered inhibitory if it would block more than 60% of radiolabelled CLMF binding to the PHA activated PBL blasts.
3. Neutralization of CLMF bioactivity as assessed by the TGF assay: An antibody was considered neutralizing if it would block more than 50% proliferation at 200 μg/ml. The results are presented as positive (+) or negative (−).
4: ND: Not Determined

EXAMPLE 14

Preparation of Antibodies Against a Synthetic Peptide Fragment of the 35,000 dalton Subunit of CLMF A peptide, comprising amino acids 3-13 of the NH$_2$-terminal sequence of the 35 kDa CLMF subunit and a COOH-terminal cysteine (L-P-V-A-T-P-D-P-G-M-F-C), was synthesized by solid-phase peptide methodology, purified by HPLC, and conjugated to keyhole limpet hemocyanin via the methylated bovine serum albumin procedure. Two rabbits were immunized intradermally with the conjugated peptide in Freund's complete adjuvant (300 μg peptide/rabbit). Six weeks after immunization, rabbits were boosted with free peptide (100 μg, intravenously) and KLH-conjugated peptide (150 μg, subcutaneously) dissolved in PBS. Serum samples were prepared from bleedings taken 7 days later. The boosting and bleeding schedule was repeated every 4-5 weeks.

Serum samples from the first and second bleedings from each rabbit were evaluated for reaction with the synthetic peptide in a direct ELISA assay. The synthetic, free peptide was coated on microtiter plates at 4 ng/ml and 20 ng/ml, and the plates were washed and blocked with bovine serum albumin. Serum samples were tested at various dilutions (Table 16), and antibody reactivity was detected with the use of a second antibody (HRP-conjugated goat anti-rabbit IgG) with o-phenylenediamine as substrate. Absorbance values were read at 490 nm after addition of $H_2SO_4$ to stop the reaction. The results indicate that antibody was produced in both rabbits against 35,000 dalton CLMF peptide (Table 16). In separate experiments, we verified that the antibody was specific for the peptide since (a) serum from non-immunized rabbits does not react with the peptide in ELISA, (b) sera from rabbits immunized with the synthetic peptide do not react with a peptide fragment from the 40,000 dalton subunit and (c) purified IgG from the serum samples also reacts with the synthetic peptide.

Figure 37:
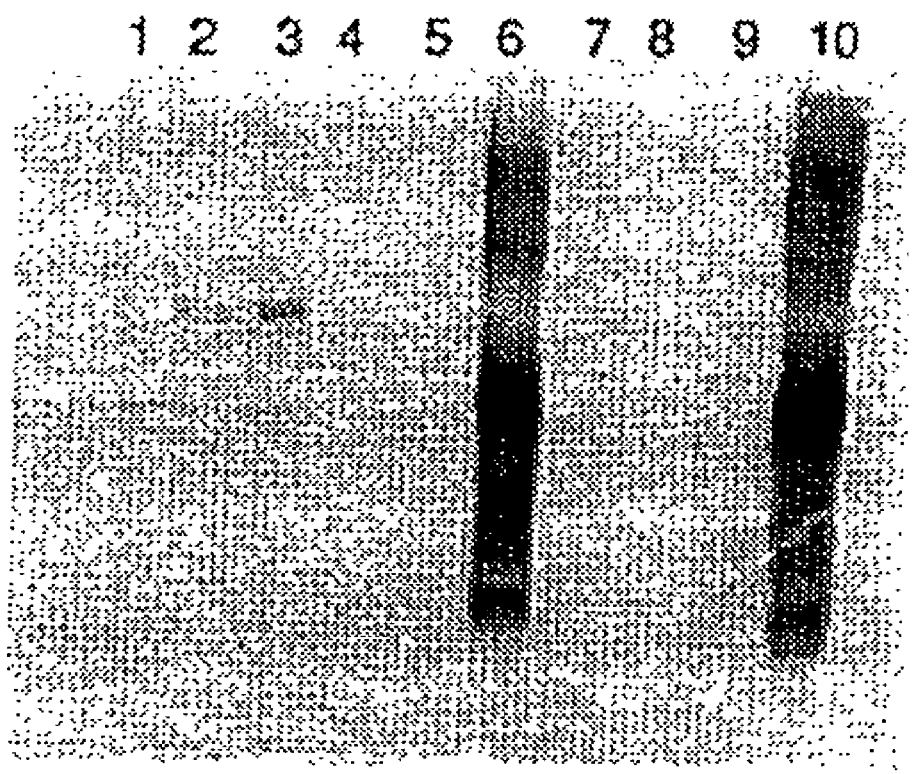
FIG. 37 shows Western blot analysis of the reactivity of a rabbit polyclonal anti-CLMF antibody with 75 kDa CLMF (nonreduced) and with 35 kDa CLMF subunit (reduced). The antibody was prepared against a synthetic peptide fragment of the 35 kDa CLMF subunit.

A serum sample from one of the rabbits (first bleed) was tested by Western blot analysis for reactivity with 75 kDa CLMF and with the 35 kDa CLMF subunit (FIG. 37). Partially purified CLMF (approximately 120 μg/ml) was run on SDS-PAGE, transferred to nitrocellulose, and treated with a 1:500 dilution of the rabbit anti-CLMF peptide antiserum. Antibody reactivity was detected by use of biotinylated goat anti-rabbit IgG and alkaline phosphatase-conjugated streptavidin. The anti-CLMF peptide antibody was found to react both with nonreduced 75 kDa CLMF protein and with the reduced 35 kDa CLMF subunit (FIG. 37).

Although the antibodies produced in this example were polyclonal, a similar approach could be used to prepare monoclonal antibodies to the 35 kDa subunit of CLMF. The synthetic peptide used in this example or other synthetic peptides based on the amino acid sequence of the 35 kDa CLMF subunit (FIG. 26) could be used to immunize rats. Fusions could be performed and hybridoma cultures screened for the production of monoclonal anti-CLMF antibodies as described above.

TABLE 16

Neutralization of CLMF Bioactivity by Monoclonal Anti-CLMF.
Assay Contents:

| CLMF[a] | Antibody[b] | | Total [3]H-Thymidine Incorporation | % Neutralization[c] |
|---|---|---|---|---|
| none | none | | 9923 ± 439 | |
| CLMF | none | | 25752 ± 592 | |
| CLMF | 4A1 | | | |
| | 100 | μg/ml | 12965 ± 938 | 81 |
| | 20 | | 12215 ± 663 | 86 |
| | 4 | | 12985 ± 269 | 81 |
| | .8 | | 19932 ± 1016 | 37 |
| | .16 | | 22379 ± 410 | 21 |
| | .03 | | 25405 ± 1093 | 2 |
| CLMF | 7B2 | | | |
| | 200 | μg/ml | 10763 ± 878 | 96 |
| | 100 | | 15083 ± 406 | 67 |
| | 20 | | 23690 ± 1228 | 13 |
| | 4 | | 25849 ± 1408 | 0 |

TABLE 16-continued

Neutralization of CLMF Bioactivity by Monoclonal Anti-CLMF.
Assay Contents:

| CLMF[a] | Antibody[b] | | Total $^3$H-Thymidine Incorporation | % Neutralization[c] |
|---|---|---|---|---|
| CLMF | Control | | | |
| | 200 | µg/ml | 27654 ± 1086 | 0 |
| | 100 | | 22221 ± 381 | 22 |
| | 20 | | 27335 ± 620 | 0 |

[a]Purified CLMF was used in the TGF assay at a concentration of 40 units/ml.
[b]Purified antibodies were added at the concentrations indicated in the table.
[c]Reduction of $^3$H-thymidine incorporation to the level seen in the absence of added cytokines was considered to be 100% neutralization.

EXAMPLE 15*

Synthesis of IgE is dependent upon the balance between the production of IL-4 and IFN-γ at the sites of T/B cell interactions (1-3). IL-4 may promote IgE synthesis not only via a direct effect on B cells, by directing the switching to IgE (4-5), but also by regulating the production of other molecules or cytokines involved in IgE regulation. For example, IL-4 markedly inhibits IFN-γ production by human lymphocytes stimulated by mitogen or allogeneic cells (6-7). Similarly, IFN-γ suppresses the in vivo synthesis of IgE not only by antagonizing the effect of IL-4 on the switching to IgE but also by inhibiting the proliferation of IL-4-producing TH22 lymphocytes (9-10) or by directing the differentiation of naive precursor T cells into T cells producing IFN-γ but not IL-4 (11). Lymphokines other than IL-4 and IFN-γ may also have an important role in the regulation of IgE synthesis. Interferon-α, a cytokine mainly produced by accessory cells, is a potent inhibitor of the in vitro and in vivo synthesis of mouse and human IgE (13), IFN-γ also counteracts the effect of IL-4 on the switching to IgE and most interestingly, like IFN-γ, it inhibits the in vivo production of IL4 and enhances that of IFN-γ(12). Interleukin-12 is a novel cytokine, which like IFN-γ and IFN-α, may be involved in protective immunity against infectious agents such as viruses. Also known as NKSF (Natural Killer Cell Stimulator Factor) or as CLMF (Cytotoxic Lymphocyte Maturation Factor) IL-12 is a 75 kDa heterodimeric glycoprotein displaying several in vitro activities including: (a) the enhancement, in synergy with IL-2, of the maturation of cytotoxic T cells and of LAK cells (lymphocyte activated killer cells); (b) the increase of the cytotoxic activity of NK cells (15); (c) the promotion of the proliferation of active T cells and NK cells (16) and; (d) the induction of IFN-γ production by resting or activated peripheral blood NK cells and T cells (17). IL-12 is a strong inhibitor of the T cell dependent synthesis of IgE by IL-4-stimulated peripheral blood mononuclear cells and the IgE inhibition may be observed in the absence of IFN-γ production.

* Provided by Dr, Guy Delespesse, University of Montreal.

Reagents

Human rIL-4 was obtained from CIBA-GEIGY, Basle, Switzerland (Dr. H. Hofstetter), anti-CD40mAb 89 (18) was received from (Schering Plough, Dardilly, France (Dr. J. Banchereau)); hydrocortisone was obtained from Sigma (St. Louis, Mo.); PWM was from Gibco Laboratories (Grand Island, N.Y.); anti-IFN-γ neutralizing mAb was purchased from Genzyme, (No. 1598-00 Boston, Mass.). In preliminary titration experiments, this antibody (25 µg/ml) completely neutralized the suppressive activity of 500 IU/ml of IFN-γ on the IL-4-stimulated synthesis of IgE by PBMC. IgE (ng/ml) in IL-4-stimulated cultures was 30±4 as compared to 9.8±2 in the presence of IFN-γ (500 IU/ml) and to 31.7±3.8 in the presence of both IFN-γ and anti-IFN-γ mAb. Anti-Lolp1 mAb is a mouse IgGI antibody directed against the pollen antigen Lolp1 (20).

Human rIL-12 and Antibodies to IL-12

Human rIL-12 was produced by cotransfection of COS cells with a 1:1 molar ratio of the two subunit cDNAs of IL-12 as described by Gubler et al. (13). Crude supernatant fluid from cultures of doubly transfected cells was used as the source of rIL-12 in these experiments. Supernatant fluid from cultures of mock transfected COS cells was used as a control. Monoclonal anti-IL-12 antibody was a 1:1 mixture of two rat monoclonal anti-human IL-12 antibodies, 4A1 and 20C2, which were isolated and purified as previously described (19). The 4A1 antibody is specific for the 40 kDa subunit of human L-12, and its isotype is IgG2b. The 20C2 antibody appears to react with the 35 kDa subunit of IL-12, and its isotype is IgG1. These two antibodies were previously found to synergize in blocking IL-12-stimulated proliferation of human PHA-activated lymphoblasts.

Cell Preparations and Culture Conditions

Cells were prepared and cultured as described (20,21): Briefly, peripheral blood mononuclear cells (PBMC) were isolated from heparinized venous blood of healthy individuals by centrifugation over Ficoll-Metrizoate. Umbilical cord blood was collected in heparin-containing tubes and was sedimented 45 min at 37° C. with dextran (10% V/V; mol. wt. 200.000, Baker Chemicals Co., Phillipsburg, N.J.); the leukocyte-rich plasma was then layered on Ficoll-Metrizoate. Cells were cultured in HB101 culture medium (Hana Biologics Inc., Alemeda, Calif.) supplemented with 5% fetal calf serum (Flow Labs, McLean, Va.) penicillin (100 U/ml), streptomycin (100 µg/ml, L glutamine (2 mM) (Gibco Laboratories), sodium pyruvate (10 mM) and Hepes (10 mM). Cells ($2 \times 10^5$ in 0.2 ml) were cultured in four replicates or more in round-bottomed 96-well tissue culture plates (Linbro) for 12 days in a humidified atmosphere of 5% $CO_2$ and 95% air. For the induction of IgE synthesis, cultures were supplemented with IL-4 at the final concentration of 10 ng/ml; this concentration was found to be optimal for the induction of IgE synthesis and the suppression of IFN-γ production in mixed-lymphocyte cultures.

RIAs

Immunoglobulins were measured in cell-free culture supernatants by means of solid-phase RIAs exactly as described (20,21); IFN-γ was measured by a commercially available RIA (Centoco Co., Malvern, Pa.) with a sensitivity of 1 IU/ml. The net synthesis of Igs and of IFN-γ was determined by subtracting the values measured in the culture supernatants of cycloheximide-treated cells (50 µg/ml) from those of untreated cells. In preliminary experiments, where the levels of IFN-γ in the supernatants of IL-12 stimulated cultures were determined at days 2, 4, 6 and 8, we found, in agreement with a previous report (17), that a plateau was obtained between day 4 to day 6. IFN-γ was therefore routinely measured at day 6; to this end, 50 µl of culture supernatants were collected and replaced by the same volume of fresh culture medium. All the culture supernatants were stored at −20° C. until the assay.

Northern Blot Analysis

Northern blot analysis was carried out exactly as described (6). Total RNA was extracted from cultured PBMC by the guanidium-thiocynate method with CsCl gradient modification and quantified by measurement of absorbance at 260 nm. The samples (20 µg per lane) were subjected to electrophoresis in formaldehyde-containing 1% agarose gel, and transferred to nylon membrane (Biotrans, ICN, Irvine, Calif.). The membrane was baked 2 h at 80° C. under vacuum, prehybridized in 50% formamide—5× Denhardt's—5×SSC—10 mM EDTA—50 mM sodium phosphate pH 6.8-0.1% SDS—250 µg/ml salmon sperm DNA and incubated overnight at 42° C. with $^{32}P$ labelled cDNA probe in the same buffer. The probes used for the detection of the germ-line and the mature form of Cε mRNA were described by Jaraba et al. (22). A 0.74 Kb Sma I fragment overlapping the germline exon was used to detect germ-line Cε transcript, and the 0.88, Kb Hinf I fragment encompassing most of the Cε1 exon and the totality of the Cε2 exon was used to detect both the productive and the germ-line Cε mRNAs.

IL-12 Suppresses IgE Synthesis

Figure 38:
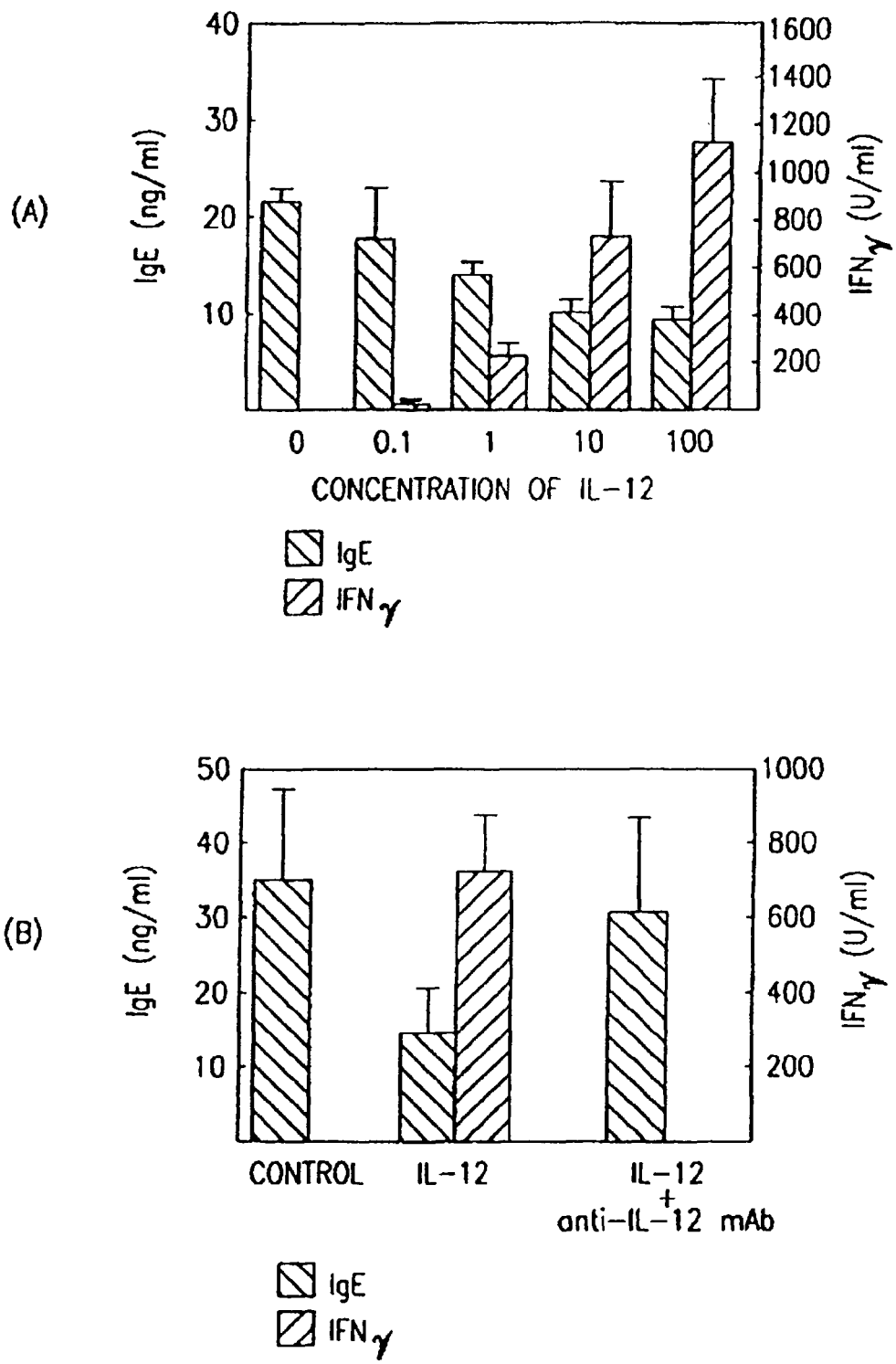
FIG. 38 shows the effect of IL-12 on IgE and-IFN-γ production by IL-4-stimulated PBMC.

As seen in table 17, IL-12 (60 pM) significantly suppresses the production of. IgE and increases the-synthesis of IFN-γ by PBMC cultured in the presence of a saturating concentration of IL4 (10 ng/ml). IL4 significantly but incompletely suppresses the IL-12-induced production of IFN-γ; and it totally abolishes the spontaneous production of IFN-γ. The effects of IL-12 on IgE and IFN-γ production are dose-dependent and they are completely abolished by neutralizing anti-IL-12 mAbs (FIG. 38). The production of IgG, IgA and IgM in IL-4-stimulated cultures is not significantly affected by IL-12. However, IL-4 does not induce the production of IgM, IgA or IgG (with the exception of IgG4) (4). The effect of Il-12 on pokeweed mitogen (PWM)-induced IgE synthesis was examined. In 3 consecutive experiments, IL-12 (60 pM) had no significant effect on the PWM-induced synthesis of IgG (1.6±0.1 versus 1.3±0.6 µg/ml; mean±1 SD), IgM (1.2±0.4 versus 1.1±0.6 µg/ml) and of IgA (1.9±0.6 versus 2.1±0.7 µg/ml).

As shown in FIG. 39, IL-12 strongly suppresses the expression of the mature but not of the germ-line Cε transcript. This indicates that IL-12 suppresses the synthesis of IgE and possibly inhibits the switching to IgE.

IL-12 appears to suppress IgE synthesis by a mechanism which is distinct from that of IFN-γ. The effect of IL-12 on the synthesis of IgE by umbilical cord blood mononuclear cells (CBMC) costimulated with IL-4 and hydrocortisone was tested. These cells were selected because of their impaired capacity to produce IFN-γ (23) and because exogenous IFN-γ was found to increase rather than to inhibit their synthesis of IgE following stimulation with IL-4 (6). Hydrocortisone (HC) was added to IL-4 stimulated CBMC for two reasons: (i) HC inhibits the production of IFN-γ, even that induced by IL-12; (ii) HC strongly increases the IL-4 stimulated synthesis of IgE, even in the absence of IFN-γ production (24). As seen (table 18), IL-12 markedly inhibits IgE synthesis by neonatal cells cultured in the presence of IL4 plus hydrocortisone and producing little or nor detectable IFN-γ. Moreover, the suppression is unchanged in the presence a large excess of neutralizing anti-IFN-γ mAb. Thus, it appears that IL-12 can inhibit IgE synthesis by a mechanism which is independent of IFN-γ.

As shown above, picomolar concentrations of IL-12 markedly inhibit the synthesis of IgE by IL-4-stimulated PBMC. The suppression of IgE is observed at the protein and the mRNA levels and it is completely overriden by neutralizing antibodies to IL-12. Given that the production of IgE by IL-4-stimulated lymphocytes involves the switching of precursor B cells to IgE rather than the selective expansion and differentiation of IgE committed B cells (4, 25), the results suggest that IL-12 inhibits the switching to IgE. Consistent with an isotype-specific activity of IL-12, no influence is found on the production of the other classes of Ig by IL4-stimulated or by PWM-stimulated PBMC. The data do not exclude an effect of IL-12 on the production of IgG4, the only human isotype other than IgE which is induced by IL-4 (4). Indeed, the measurement of IgG4, which is produced in very small quantities, requires the utilization of IgG4 specific antibodies that are not employed in the RIA for IgG determination.

IL-12 induces the production of significant amounts of IFN-γ even in the presence of a high concentration of IL-4, that was shown to completely suppress IFN-γ production and to induce IgE synthesis in mixed lymphocyte cultures (6,7). Knowing that IFN-γ directs the in vitro as well as the in vivo differentiation of naive T cells into TH1 type of cells, it is reasonable to assume that IL-12 may display the same activity even in the presence of IL, which may also be produced by non-T cells (26). According to this view, IL-12 might well pay a pivotal role in determining the outcome of certain immune responses to certain antigens or pathogens that are known to preferentially generate TH1 or TH2 helper cells. The cellular origin of IL-12 is consistent with a putative role of this lymphokine in the differentiation of naive T cells. Indeed, IL-12 may be produced not only by Epstein-Barr virus transformed B cells from which it was isolated but also by normal B cells that are known to be efficient antigen-presenting cells.

In preliminary experiments using neutralizing antibodies to IFN-γ the IL-12 mediated suppression of IgE synthesis by adult PBMC was not consistently overcome. These results may be easily explained by (i) the relatively high levels of IFN-γ in IL-12 containing cultures and (ii) the difficulty in blocking the biological activity of endogenously produced IFN-γ. IL-12 also suppresses IgE by another mechanism which is IFN-γ independent. The existence of such a mechanism is demonstrated by the ability of IL-12 to markedly inhibit IgE synthesis by IL-4 and hydrocortisone-costimulated neonatal lymphocytes which do not produce detectable amounts of IFN-γ. It is unlikely that such undetectable levels of IFN-γ (<1 IU) might nevertheless account for the suppression of IgE given that a very large excess of neutralizing anti-IFN-γ antibody failed to increase the IgE response. Whereas both IL-12 and IFN-γ markedly suppress the accumulation of productive Cε mRNA in IL-4-stimulated PBMC (>90% suppression), IFN-γ, but not IL-12, also suppress the expression of germ-like transcript (50-70% inhibition). (5) IL-12 inhibits IgE synthesis by PBMC costimulated with IL-4 and anti-CD40 mAb, a model where IFN-γ was reported to be inactive (27). In three such experiments where PBMC were cultured with IL-4 and anti-CD40 mAb 89 (0.5 µg/ml), the production of IgE dropped from 70±28 ng/ml (mean±1SD) to 20±8 ng/ml in the presence of IL-12 (60 pM) as compared to 79±35 ng/ml in the presence of IFN-γ (100 IU/ml). Taken collectively, the present results demonstrate that, like the interferons, IL-12 plays an important role not only in protective immunity but also in the regulation of isotype selection.

TABLE 17

| ADDITION | EXP. 1 | | EXP. 2 | |
|---|---|---|---|---|
| | IgE | IFN-γ | IgE | IFN-γ |
| — | <0.2 | 214 | <0.2 | 62 |
| IL-4 | 57 | <1 | 204 | <1 |
| IL-12 | <0.2 | 3364 | <0.2 | 2800 |
| IL-4 + IL-12 | 19 | 1348 | 58 | 810 |

PBMC were cultured for 12 days in the absence or in the presence of IL-4 (10 ng/ml), IL-12 (60 pM) or both. Shown are the mean values of IgE (ng/ml) and IFN-γ (IU/ml) measured in 4 replicate cultures; the variation between the replicates was below 20%. Supernatant fluids from cultures of mock transfected COS cells were inactive when used at the same dilutions as the IL-12 containing supernatant fluids (not shown).

TABLE 18

EFFECT OF IL-12 ON IgE SYNTHESIS BY NEONATAL LYMPHOCYTES STIMULATED WITH IL-4 AND HYDROCORTISONE

| ADDITION | EXP. 1 | | EXP. 2 | | EXP. 3 | | EXP. 4 | |
|---|---|---|---|---|---|---|---|---|
| | IgE | IFN-γ | IgE | IFN-γ | IgE | IFN-γ | IgE | IFN-γ |
|  | 373 | <1 | 44 | <1 | 20 | <1 | 302 | <1 |
| IL-12 | 6 | <1 | 8 | <1 | <0.2 | 17 | 20 | 33 |
| IL-12 + Anti-IFN-γ | 7 | <1 | 10 | <1 | <0.2 | <1 | 21 | <1 |
| IL-12 + Anti-Lolp1 | 6 | <1 | NT | NT | NT | NT | 18 | 128 |

Umbilical cord blood mononuclear cells were cultured for 12 days in the presence of IL-4 and 10 μM hydrocortisone. IL-12 (60 pM), anti-IFN-γ mAb (1000 neutralizing U/ml) or the isotype-matched control (anti-Lolp1) mAb (50 μg/ml) were added at the initiation of the culture. IgE (ng/ml) and IFN-γ (IU/ml) were measured at day 12 and day 6 respectively. Shown are the mean values of quadruplicate cultures; the variation between the replicates was below 20%.

EXAMPLE 16

Provided below are several exemplary formulations for parenteral use, injection, or aerosol administration.

The following formulations are parenteral solutions. These solutions may also be lyophilized to form powders.

3.0 mg/ml CLMF is dissolved in phosphate-buffered saline pH 7 (PBS pH 7) q.s. 1 ml. To this solution may be added one of the following: 0.2 mg/ml Polysorbate 80; or 5.0 mg human serum albumin; or 10.0 mg/ml benzyl alcohol. Alternatively, a formulation including 3.0 mg/ml CLMF; 25 mg/ml mannitol; and Tris buffer pH 7 q.s. 1 ml may be used.

A preferred formulation which is a lyophilized powder for injection includes 3.0 mg/ml CLMF, 3.0 mg/ml trehalose, and PBS pH 7 q.s. 1 ml.

All the above formulations are produced by mixing the indicated components in an appropriate vessel, filtering the resulting solution to sterility using an appropriate bacteria-retentive filter, and lyophilizing the resulting sterile solution in lyophilization vessels using an appropriate cycle. The lyophilization vessels should then be stoppered using the appropriate head pressure gas and stopper.

A suspension formulation for an inhalation aerosol may include the following components: 1.5% w/w CLMF; 5.0% w/w mannitol; 2.0% w/w sorbitan trioleate; 64.0% w/w Freon 12; 11.5% w/w Freon 11; and 16.0% w/w Freon 114. This formulation may be produced by conventional means. A preferred method of production is to prepare an aqueous solution of CLMF and mannitol and lyophilize this solution under suitable conditions. To the resulting dry product is added sorbitan trioleate and Freon 11, and the resulting mixture is homogenized. The resulting suspension is filled into an aerosol container, which is crimped to seal with an appropriate valve inserted. The container is then pressure-filled with an 80:20 mixture of Freon 12 and Freon 114.

REFERENCES

1. Finkelman, F. D., J. Holmes, I. M. Katona, J. F. Urban, Jr., J. P. Beckrmann, L. S. Park, K. A. Schooley, R. L. Coffman, T. R. Mosmann, and W. E. Paul. 1990. Lymphokine control of in vivo immunoglobulin isotype selection. Annu. Rev. Immunol. 8:303.

2. Snapper, C. M., and W. E. Paul. 1987. Interferon-γ and B cell stimulatory factor-1 reciprocally regulate Ig isotype production. Science (Washington, D.C.) 236:944.

3. Pene, J., F. Rousset, F. Briere, 1. Chretiern, I. Y. Bonnefoy, H. Spits, T. Yokota, K. Arai, J. Banchereau, and J. de Vries. 1988. IgE production by normal human lymphocytes is induced by interleukin-4 and suppressed by interferons γ and α and prostaglandin E2. Proc. Natl. Acad. Sci. USA 85:6880.

4. Gascan, H., J. F. Gauchat, M. G. Roncarolo, H. Yssel, H. Spits, and J. E. deVries. 1991. Human B cell clones can be induced to proliferate and to switch to IgE and IgG4 synthesis by interleukin 4 and a signal provided by activated CD4+ T cell clones. J. Exp. Med. 173:747-750

5. Gaucks4 J. F., D. A. Lebman, R. L. Coffman, H. Gascan, and J. E. deVries, 1990 Structure and expression of germlike ε transcripts in human B cells-induced by interleukin 4 to switch to IgE production J. Exp. Med. 172:463-473.

6. Peleman R., J. Wu, C. Fargeas, and G. Delespesse. 1989. Recombinant interleukin-4 suppresses the production of interferon γ by human mononuclear cells. J. Exp. Med. 170: 1751-1756.

7. Vercelli, D, H. H. Jabara, R. P. Lauener, and R. S. Geha. 1990. Interleukin-4 inhibits the synthesis of interferon-γ and induces the synthesis of IgE in mixed lymphocyte cultures. J. Immunol. 144:570.

8. Coffman, R. L, K. Varkila, P. Scott, and R. Chatelain. 1991. Role of cytokines in the differentiation of CD4+ T-cell subsets in vivo. Immunol. Reviews 123:189-207.

9. Gajewski, T. F., and F. W. Fitch. 1988. Anti-proliferative effect of IFN-γ in immune regulation. 1. IFN-γ inhibits the proliferation of TH2 but not TH1 murine helper T cell clones. J. Immunol. 140:4245.

10. Fernandez-Botran, R., V. M. Sanders, T. R. Mosmann, I. W. Uhr, and E. S. Viletta. 1988. Lymphokine-mediated regulation of the proliferative response of clones of TH1 and TH2 cells. J. Exp. Med. 168:543-548.

11. Scott, P. 1991. IFN-γ modulates the early development of TH1 and TH2 responses in a murine model of cutaneous leishmaniasis. J. Immunol. 147:3149-3155.

12. Finkelman, F. D., A. Svetic, 1. Gresser, C. Snapper, J. Holmes, P. P. Trotta, I. M. Katona, and W. C. Gause. 1991. Regulation by interferon-α of immunoglobulin isotype selection and lymphokine production in mice. J. Exp. Med. 174: 1179-1188.

13. Gubkr, U., A. O. Chua, D. S. Schoenhaut, C. M. Dwyer, W. McComas, R. Motyka, N. Nabavi, A. G. Wolitzky, P. M. Quinn, P. C. Familletti and M. K. Gately. 1991. Co-expression of two distinct genes is required to generate secreted bioactive cytotoxic lymphocyte maturation factor. Proc. Natl. Acad. Sci. USA 88:4143.

14. Wolf, S. F., P. A. Temple, M. Kobayashi, D. Young, M. Dicig, L. Lowe, R. Dzialo, L. Fitz, C. Ferenz, R. M. Hewick, K. Kelleher, S. H. Herrmann, S. C. Clark, L. Azzoni, S. H. Chan, G. Trinchieri, and B. Perussia. 1991. Cloning of cDNA for natural killer cell stimulatory factor, a heterodimeric cytokine with multiple biologic effects on T and natural killer cells. J. Immunol. 146:3074-3081.

15. Kobayashi, M., L. Fitz, M. Ryan, R. M. Hewick, S. C. Clark, S. Chan, R. Loudon, F. Sherman, B. Perussia, and G. Trinchieri. 1989. Identification and purification of natural killer cell stimulatory factor (NKSF), a cytokine with multiple biologic effects on human lymphocytes. J. Exp. Med. 170:827-845.

16. Gately, M. K., B. B. Desai, A. G. Wolitzky, P. M. Quinn, C. M. Dwyer, F. J. Podlaski, P. C. Familletti, F. Sinigaglia, R. Chizonnite, U. Gubler, and A. S. Stern. 1991. Regulation of human lymphocyte proliferation by a heterodimeric cytokine, IL12 (cytotoxic lymphocyte maturation factor). J. Immunol. 147:874-882.

17. Chan, S. H., B. Perussia, I. W. Gupta, M. Kobayashi, M. Pospisil, H. A. Young, S. F. Wolf, D. Young, S. C. Clark, and G. Trinchieri 1991. Induction of interferon γ production by 17. Rousset, F., E. Garcia, and J. Banchereau, 1991. Cytokine-induced proliferation and immunoglobulin production of human B lymphocytes triggered through their CD40 antigen, J. Exp. Med. 173:705-710.

natural killer cell stimulatory factor: characterization of the responder cells and synergy with other inducers; J. Exp. Med. 173:869-879.

18. Rousset, F., E. Garcia, and J. Banchereau, 1991. Cytokine-induced proliferation and immunoglobulin production of human B lymphocytes triggered through their CD40 antigen, J. Exp. Med. 173:705-710.

19. Chizzonite, R., T. Truitt, F. Podlaski, A. G. Wolitzky, P. M. Quinn, P. Nunes, A. S. Stern, and M. K. Gately 1991. IL-12: Monoclonal antibodies specific for the 40 kDa subunit block receptor binding and biologic activity on activated human lymphoblasts. J. Immunol. 147:-1548-1556.

20. Sarfati, M., and G. Delespesse. 1988. Possible role of human lymphocyte receptor for IgE (CD23) or its soluble fragments in the in vitro synthesis of human IgE. 1. Immunol. 141:2195.

21. Peleman, R., and G. Delespesse. 1990. In vitro synthesis of human IgE by neonatal lymphocytes: enhancing effect of interferon-γ. Cell. Immunol. 129:299-309.

22. Jabara, H. H., L. C. Schneider, S. K. Shapira, C. Alfieri, C. T. Moody, E. Kieff, R. Geha and D. Vercelli. 1990. Induction of germ-line and mature Cε transcripts in human B cells stimulated with rIL-4 and EBV. J. Immunol. 145:3468.

23. Kibler, R., M. J. Hicks, A. L. Wright, and L. M. Taussig. 1986. A comparative analysis of cord blood and adult lymphocytes: interleukin-2 and interferon production, natural killer cell activity, and lymphocyte populations. Diagn. Immunol. 4:201-208.

24. Wu, C. Y.; M. Sarfati, C. Heusser, S. Fournier, M. Rubio-Trujillo, R. Peleman, and G. Delespesse. 1991. Glucocorticoids increase the synthesis of immunoglobulin E by interleukin 4-stimulated human lymphocytes. J. Clin. Invest. 87:870-877.

25. Vercelli, D. and R. S. Geha., 1991. Regulation of IgE synthesis in humans: A tale of two signals. J. Aller. Clin. Immunol. 88:285-295.

26. Plant, M, J. H. Pierce, C. J. Watson, J. Hanley-Hyde, R. P. Nordan, W. E. Paul. 1989. Mast cell lines produce lymphokines in response to cross-linkage of FcεRI or calcium ionophores. Nature 339:64.

27 Zhang, K, E. A. Clark, and A. Saxon. 1991. CD40 stimulation provides an IFN-γ-independent and IL-4-dependent differentiation signal directly to human B cells for IgE production. J. Immunol. 146:1836-1842.

The invention claimed is:

1. An isolated monoclonal antibody which binds a 40 kD subunit of cytotoxic lymphocyte maturation factor (CLMF), wherein said monoclonal antibody is capable of blocking CLMF induced proliferation of lymphoblasts in a CLMF dependent T cell growth factor assay.

2. The monoclonal antibody according to claim 1, wherein said monoclonal antibody is capable of blocking CLMF induced proliferation of lymphoblasts in a T cell growth factor assay by more than 50%.

3. The monoclonal antibody according to claim 1, wherein said 40 kD subunit has the amino acid sequence of amino acids 23-328 of the amino acid sequence shown in FIG. 25A-FIG. 25D (SEQ ID NO:3), and wherein when said 40 kD subunit is combined with a 35 kD subunit of CLMF that has the amino acid sequence of amino acids 23-219 of the amino acid sequence shown in FIGS. 26A-26C (SEQ ID NO:5), the combined subunits form a CLMF protein that has a specific activity of at least $5.2 \times 10^7$ Units/mg when determined in a T cell growth factor assay.

4. The isolated monoclonal antibody according to claim 3 wherein said combined subunits form a CLMF protein that has a specific activity of $8.5 \times 10^7$ Units/mg when determined by said T cell growth factor assay.

5. An isolated monoclonal antibody which binds a 40 kD subunit of cytotoxic lymphocyte maturation factor (CLMF), wherein said 40 kD subunit comprises the amino acid sequence of amino acids 23-328 of the amino acid sequence shown in FIG. 25A-FIG. 25D (SEQ ID NO:3), wherein when said 40 kD subunit is combined with a 35 kD subunit of CLMF that comprises the amino acid sequence of amino acids 23-219 of the amino acid sequence shown in FIGS. 26A-26C (SEQ ID NO:5), the combined subunits form a CLMF protein that has a specific activity of at least $5.2 \times 10^7$ Units/mg when determined in a T cell growth factor assay, and wherein said isolated monoclonal antibody is capable of blocking CLMF induced proliferation of lymphoblasts in a CLMF dependent T cell growth factor assay by more than 50%.

* * * * *